US009469643B2

(12) United States Patent
Carra et al.

(10) Patent No.: US 9,469,643 B2
(45) Date of Patent: Oct. 18, 2016

(54) POLYMORPHIC FORMS OF (S)-2-(1-(9H-PURIN-6-YLAMINO)PROPYL)-5-FLUORO-3-PHENYLQUINAZOLIN-4(3H)-ONE

(71) Applicant: GILEAD CALISTOGA LLC, Foster City, CA (US)

(72) Inventors: Ernest Carra, Foster City, CA (US); Michael Gerber, Oakland, CA (US); Bing Shi, Redwood City, CA (US); Keiko Sujino, Edmonton (CA); Duong Tran, Edmonton (CA); Fang Wang, Foster City, CA (US); Jerry B. Evarts, Seattle, WA (US)

(73) Assignee: Gilead Calistoga, LLC., Foster City, CA (US)

( * ) Notice: Subject to any disclaimer, the term of this patent is extended or adjusted under 35 U.S.C. 154(b) by 181 days.

(21) Appl. No.: 14/493,261

(22) Filed: Sep. 22, 2014

(65) Prior Publication Data
US 2015/0080572 A1    Mar. 19, 2015

Related U.S. Application Data

(62) Division of application No. 13/786,222, filed on Mar. 5, 2013, now Pat. No. 8,865,730.

(60) Provisional application No. 61/606,870, filed on Mar. 5, 2012.

(51) Int. Cl.
C07D 473/34    (2006.01)

(52) U.S. Cl.
CPC .................... C07D 473/34 (2013.01)

(58) Field of Classification Search
CPC .................................................... C07D 473/34
See application file for complete search history.

(56) References Cited

U.S. PATENT DOCUMENTS

| | | | |
|---|---|---|---|
| 3,322,756 A | 5/1967 | Ruschig et al. |
| 3,691,016 A | 9/1972 | Patel |
| 3,897,432 A | 7/1975 | Shen et al. |
| 3,969,287 A | 7/1976 | Jaworek et al. |
| 3,984,555 A | 10/1976 | Amschler et al. |
| 4,179,337 A | 12/1979 | Davis et al. |
| 4,183,931 A | 1/1980 | Wolfe et al. |
| 4,195,128 A | 3/1980 | Hildebrand et al. |
| 4,225,489 A | 9/1980 | Rolf et al. |
| 4,229,537 A | 10/1980 | Hodgins et al. |
| 4,247,642 A | 1/1981 | Hirohara et al. |
| 4,289,872 A | 9/1981 | Denkewalter et al. |
| 4,301,144 A | 11/1981 | Iwashita et al. |
| 4,330,440 A | 5/1982 | Ayers et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,925,673 A | 5/1990 | Steiner et al. |
| 5,013,556 A | 5/1991 | Woodle et al. |
| 5,225,347 A | 7/1993 | Goldberg et al. |
| 5,229,490 A | 7/1993 | Tam |
| 5,378,725 A | 1/1995 | Bonjouklian et al. |
| 5,480,906 A | 1/1996 | Creemer et al. |
| RE35,862 E | 7/1998 | Steiner et al. |
| 5,858,753 A | 1/1999 | Chantry et al. |
| 5,882,910 A | 3/1999 | Chantry et al. |
| 5,948,664 A | 9/1999 | Williams et al. |
| 5,985,589 A | 11/1999 | Chantry et al. |
| 6,046,049 A | 4/2000 | Monia et al. |
| 6,048,970 A | 4/2000 | Lal et al. |
| 6,277,981 B1 | 8/2001 | Tu et al. |
| 6,291,220 B1 | 9/2001 | Williams et al. |
| 6,369,038 B1 | 4/2002 | Blumenfeld et al. |
| 6,410,224 B1 | 6/2002 | Stinchcomb et al. |
| 6,426,337 B1 | 7/2002 | Cox et al. |
| 6,482,623 B1 | 11/2002 | Vanhaesebroeck et al. |
| 6,518,277 B1 | 2/2003 | Sadhu et al. |
| 6,667,300 B2 | 12/2003 | Sadhu et al. |
| 6,696,250 B1 | 2/2004 | Cech et al. |
| 6,800,620 B2 | 10/2004 | Sadhu et al. |
| 6,949,535 B2 | 9/2005 | Sadhu et al. |
| 7,932,260 B2 | 4/2011 | Fowler et al. |
| 8,138,195 B2 | 3/2012 | Sadhu et al. |
| 8,207,153 B2 | 6/2012 | Fowler et al. |
| 8,492,389 B2 | 7/2013 | Sadhu et al. |
| RE44,599 E | 11/2013 | Fowler et al. |
| 8,586,597 B2 | 11/2013 | Fowler et al. |
| RE44,638 E | 12/2013 | Fowler et al. |
| 8,623,881 B2 | 1/2014 | Sadhu et al. |
| 8,637,533 B2 | 1/2014 | Sadhu et al. |
| 8,653,077 B2 | 2/2014 | Sadhu et al. |
| 8,779,131 B2 | 7/2014 | Kesicki et al. |

(Continued)

FOREIGN PATENT DOCUMENTS

CN    101031569 A    9/2007
EP    0 525 960 A1    2/1993

(Continued)

OTHER PUBLICATIONS

"Acute Congestive Heart Failure", Thomas N. Levin, Postgraduate Medicine, vol. 101, No. 1, 1997.
Sutton, A. (Jun. 9, 2006). "Baylor, St. Luke's study uses gene therapy as pancreatic cancer", located at <http: //www.bcm.edu/news/item.cfm?newsiD=640>, last visited on Sep. 2, 2006, 2 pages.
Anonymous (2006). "Cardiovascular Disease: Treatment for Stroke", Stanford Hospital & Clinics, located at <http://www.stanfordhospital.com/healthLib/atoz/cardiac/stktreat.html>, last visited on Sep. 19, 2006, 2 pages.
Marchione et al. (2006). "Drugs hold promise in kidney cancer fight", located at <http://www.ledger-enquirer.com/mid/ledger-enquirer/living/health/14744763. htm>, last visited on Sep. 2, 2006, 3 pages.
Anonymous (2006). "Heart Disease", WebMD, located at <http://www.webmd.com/content/pages/911675 57842. htm> as retrieved on Sep. 14, 2006, 1 page.
Anonymous, (2010). "Multiple Sclerosis", located at <http://www.health.nytimes.com/health/guides/disease/multiple-sclerosis/overview.html>, last visited Aug. 1, 2010, 4 pages.

(Continued)

Primary Examiner — Kendra D Carter
(74) Attorney, Agent, or Firm — Yu-Ming Dammann

(57) ABSTRACT

Polymorphs of (S)-2-(1-(9H-purin-6-ylamino)propyl)-5-fluoro-3-phenylquinazolin-4(3H)-one, compositions thereof, methods for their preparation, and methods for their use are disclosed.

6 Claims, 17 Drawing Sheets

(56) References Cited

U.S. PATENT DOCUMENTS

| | | | |
|---|---|---|---|
| 8,865,730 B2 | 10/2014 | Carra et al. | |
| 2004/0023390 A1 | 2/2004 | Davidson et al. | |
| 2004/0092561 A1 | 5/2004 | Ruckle et al. | |
| 2004/0121996 A1 | 6/2004 | Barvian et al. | |
| 2004/0138199 A1 | 7/2004 | Gogliotti et al. | |
| 2004/0242631 A1 | 12/2004 | Garlich et al. | |
| 2004/0248953 A1 | 12/2004 | Gogliotti et al. | |
| 2004/0248954 A1 | 12/2004 | Gogliotti et al. | |
| 2004/0259926 A1 | 12/2004 | Bruendl et al. | |
| 2005/0004195 A1 | 1/2005 | Para et al. | |
| 2005/0020630 A1 | 1/2005 | Connolly et al. | |
| 2005/0020631 A1 | 1/2005 | Gogliotti et al. | |
| 2005/0043239 A1 | 2/2005 | Douangpanya et al. | |
| 2005/0054614 A1 | 3/2005 | Diacovo et al. | |
| 2005/0239809 A1 | 10/2005 | Watts et al. | |
| 2006/0079538 A1 | 4/2006 | Hallahan et al. | |
| 2006/0106038 A1 | 5/2006 | Bouscary et al. | |
| 2008/0287469 A1 | 11/2008 | Diacovo et al. | |
| 2010/0029693 A1 | 2/2010 | Douangpanya et al. | |
| 2010/0202963 A1 | 8/2010 | Gallatin et al. | |
| 2010/0249155 A1 | 9/2010 | Evarts et al. | |
| 2010/0256167 A1 | 10/2010 | Fowler et al. | |
| 2011/0044942 A1 | 2/2011 | Puri et al. | |
| 2011/0230465 A1 | 9/2011 | Stammers et al. | |
| 2012/0015964 A1 | 1/2012 | Fowler et al. | |
| 2012/0040980 A1 | 2/2012 | Huggins et al. | |
| 2014/0121223 A1 | 5/2014 | Fowler et al. | |
| 2014/0121224 A1 | 5/2014 | Fowler et al. | |
| 2014/0154772 A1 | 6/2014 | Sadhu et al. | |
| 2014/0378479 A1 | 12/2014 | Kesicki et al. | |

FOREIGN PATENT DOCUMENTS

| | | | |
|---|---|---|---|
| EP | 0 525 960 B1 | 2/1993 | |
| EP | 0 675 124 A2 | 10/1995 | |
| EP | 0 675 124 A3 | 10/1995 | |
| EP | 0 716 857 A1 | 6/1996 | |
| EP | 0 716 857 B1 | 6/1996 | |
| EP | 0 884 310 A1 | 12/1998 | |
| EP | 0 884 310 B1 | 12/1998 | |
| EP | 0 900 568 A2 | 3/1999 | |
| EP | 0 900 568 A3 | 3/1999 | |
| GB | 1356763 A | 6/1974 | |
| GB | 2 017 097 A | 10/1979 | |
| JP | 55 118917 A2 | 9/1980 | |
| JP | 55 118918 A2 | 1/1981 | |
| JP | 56 002322 A2 | 1/1981 | |
| JP | 2003-519698 A | 6/2003 | |
| JP | 2007-537291 A | 12/2007 | |
| WO | WO-93/21259 A1 | 10/1993 | |
| WO | WO-94/17090 A1 | 8/1994 | |
| WO | WO-95/24379 A1 | 9/1995 | |
| WO | WO-96/04923 A1 | 2/1996 | |
| WO | WO-96/25488 A1 | 8/1996 | |
| WO | WO-96/32478 A1 | 10/1996 | |
| WO | WO-97/34631 A1 | 9/1997 | |
| WO | WO-97/41097 A2 | 11/1997 | |
| WO | WO-97/43276 A1 | 11/1997 | |
| WO | WO-97/46688 A1 | 12/1997 | |
| WO | WO-98/33802 A1 | 8/1998 | |
| WO | WO-98/38173 A1 | 9/1998 | |
| WO | WO-99/08501 A2 | 2/1999 | |
| WO | WO-99/08501 A3 | 2/1999 | |
| WO | WO-99/34804 A1 | 7/1999 | |
| WO | WO-01/00881 A1 | 1/2001 | |
| WO | WO-01/30768 A1 | 5/2001 | |
| WO | WO-01/30768 C2 | 5/2001 | |
| WO | WO-01/051919 A3 | 7/2001 | |
| WO | WO-01/53266 A1 | 7/2001 | |
| WO | WO-01/57034 A1 | 8/2001 | |
| WO | WO-01/81346 A2 | 11/2001 | |
| WO | WO-01/81346 A3 | 11/2001 | |
| WO | WO-03/035075 A1 | 5/2003 | |
| WO | WO-03/106622 A2 | 12/2003 | |
| WO | WO-03/106622 A3 | 12/2003 | |
| WO | WO-2004/007491 A1 | 1/2004 | |
| WO | WO-2004/012768 A1 | 2/2004 | |
| WO | WO-2004/026285 A2 | 4/2004 | |
| WO | WO-2004/026285 A3 | 4/2004 | |
| WO | WO-2004/029055 A1 | 4/2004 | |
| WO | WO-2004/052373 A1 | 6/2004 | |
| WO | WO-2004/056820 A1 | 7/2004 | |
| WO | WO-2004/089925 A1 | 10/2004 | |
| WO | WO-2004/108708 A1 | 12/2004 | |
| WO | WO-2004/108709 A1 | 12/2004 | |
| WO | WO-2004/108713 A1 | 12/2004 | |
| WO | WO-2004/108713 C1 | 12/2004 | |
| WO | WO-2004/108715 A1 | 12/2004 | |
| WO | WO-2004/108715 C1 | 12/2004 | |
| WO | WO-2005/016348 A1 | 2/2005 | |
| WO | WO-2005/016349 A1 | 2/2005 | |
| WO | WO-2005/067901 A2 | 7/2005 | |
| WO | WO-2005/067901 A3 | 7/2005 | |
| WO | WO-2005/113556 A1 | 12/2005 | |
| WO | WO-2005/120511 A1 | 12/2005 | |
| WO | WO-2009/058361 A1 | 5/2009 | |
| WO | WO-2010/057048 A1 | 5/2010 | |
| WO | WO-2010/065923 A2 | 6/2010 | |
| WO | WO-2010/065923 A3 | 6/2010 | |
| WO | WO-2010/123931 A1 | 10/2010 | |
| WO | WO-2011/156759 A1 | 12/2011 | |
| WO | WO-2013/134288 A1 | 9/2013 | |

OTHER PUBLICATIONS

Anonymous, (2004). "NIH Heart Disease & Stroke Research: Fact Sheet", American Heart Association, located at <http://www.americanheart.org/presenter.jhtml?identifier=3010188>, last visited Feb. 17, 2004, 1 page.
Anonymous (2010). "Spinal Cord Injury", located at <http://www.medicinenet.com/spinal cord iniury/page.htm>, last visited on Aug. 1, 2010, 3 pages.
Anonymous (2010) "Systemic Lupus Erythematosus", located at <http://www.nlm.nih.gov/medlineplus/ency/article/000435.htm>, last visited Aug. 1, 2010, 4 pages.
"Chemia Lekow", ed. E. Pawelczyk, PZWL, Warszawa 1986, see, part 1.2.2.
"Preparatyka Organiczna", ed. A.I. Vogel, WNT, Warszawa 1984, page, e.g. 83.
Abu-Duhier et al., Br. J. Haematol. (2001) 113:983-988.
Adamkiewicz, "Tumor Angiogenesis: Mechanisms" IMT Marburg—Research Group, retrieved from the internet on Apr. 13, 2004, located at: <http://www.imt.uni-marburg.de/~adamkiew/mechanism.html>. 2 pages.
Advisory Action from U.S. Appl. No. 11/596,092, mailed on Jul. 27, 2010.
Ager et al., J. Med. Chem. (1977) 20:379-386.
Ali et al., Nature (2004) 431:1007-1011.
Alon et al., "The molecular basis of leukocyte adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, located at <http://www.weizmann.ac.il/Biology/open day 2002/book/ronen alon.pdf>, 2 pages.
Amendment from U.S. Appl. No. 09/841,341, filed Aug. 21, 2002.
Amendment from U.S. Appl. No. 10/027,591, filed on Jun. 3, 2003.
Amendment in Response to Final Office Action from U.S. Appl. No. 11/596,092, filed on Jul. 19, 2010.
Amendment in Response to Non-Final Office Action / Restriction Requirement from U.S. Appl. No. 11/884,566, filed Jun. 7, 2010.
Amendment in Response to Non-Final Office Action from U.S. Appl. No. 10/918,803, filed on Oct. 1, 2008.
Amendment in Response to Non-Final Office Action from U.S. Appl. No. 10/918,803, filed on Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Sep. 4, 2009.

(56) References Cited

OTHER PUBLICATIONS

Amendment in Response to Non-Final Office Action from U.S. Appl. No. 11/110,204, filed Jun. 4, 2010.
Amendment in Response to Non-Final Office Action from U.S. Appl. No. 11/596,092, filed on Nov. 10, 2009.
Amendment in Response to Non-Final Office Action from U.S. Appl. No. 11/596,092, filed Mar. 24, 2010.
Amendment Under 37 C.F.R. § 1.111 from U.S. Appl. No. 11/129,006, filed on Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed on Sep. 1, 2010.
Amin et al., Circ Res (2003) 93(4):321-329.
Amine, M.S. et al. (Nov. 1998). "Uses of Quinazolin-2-[(β-Propionoyl) Isothiocyanate]-4-One as a Building Block in Synthesis of Some Heterocyclic Compounds of Expected Biological Activity," *Indian Journal of Chemistry* 37B(11):1153-1156.
Angel, Activities of Phosphoinositide Kinase-3 (PI3K) (1999) retrieved from the internet on May 22, 2003, URL: http://www.chem.csustan.edu/chem4400/SJBR/ange199.htm.
Angio World, "How Angiogenesis Complicates Psoriasis" (2001) retrieved from the internet on Apr. 13, 2004, located at <http://www.angioworld.com/psoriasis.htm>,1 page.
Annabi et al., J. Cell. Biochem. (2004) 91:1146-1158.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Azenabor, A.A. et al. (2006). "Macrophage Antioxidant Enyzmes Regulate *Chlamydia Pneumoniae*chronicity: Evidence of the Effect of Redox Balance on Host-Pathogen Relationship," *Immunobiology* 211(5):325-339.
Bader, A.G. et al. (2005). "Oncogenic PI3K Deregulates Transcription and Translation," *Nature Reviews Cancer* 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," *Az. J. Pharm. Sci.* 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Bergers et al., Science (1999) 284:808-812.
Bharadwaj et al., J. Immunol. (2001) 166:6735-6741.
Binetruy-Tournaire et al., EMBO J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.
Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44th Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," *Haematologica* 95(s2):466, Abstract No. 1130.
Brunn et al., EMBO J. (1996) 15:5256-5267.
Burgering et al., Nature (1995) 376:599-602.
Butcher et al., Science (1996) 272:60-66.

Cadwallader et al., J. Immunol. (2002) 169:3336-3344.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
Cas Abstract, Accession No. DN 86:83505 [1977] pp. 112-118.
Cebon et al., Cancer Immun. (2003) 3:7-25.
Chang et al., Exp. Opin. Ther. Patents (2001) 11:45-59.
Chang, BioMed. Eng. Online (2003) 2:12.
Chantry, D. et al. (1997). "p110δ, a Novel Phosphatidylinositol 3-Kinase Catalytic Subunit That Associates with p85 and Is Expressed Predominantly in Leukocytes," *J. Biol. Chem.* 272(31):19236-19241.
Chapman-Kirkland, E.S. et al. (1991). "Superoxide Anion Production From Human Neutrophils Measured with an Improved Kinetic and Endpoint Microassay," *J Immunol Meth* 142(1):95-104.
Chen et al., Blood (2000) 96:3181-3187.
Chern et al., Chem. Pharm. Bull. (1998) 46(6):928-933.
Chern et al., Chemical Abstracts (1998) 129(16):676.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.
Cleary, J.M. et al. (2010). "Development of Phosphoinositide-3 Kinase Pathway Inhibitors for Advanced Cancer," *Curr. Oncol. Rep.* 12:87-94.
Coligan et al., Current Protocols in Protein Science (2002) 3:15-20.
Computer Search Cart Navigator, retrieved from the internet on Mar. 22, 2001, URL: http://www.chemnavigator.com/members/CartNavigator.asp#sample1, 8 pages.
Constantin et al., Immunity (2000) 13:759-769.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dania et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351:95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.
Doggett et al., Biophys. J. (2002) 83:194-205.
Domanig, R. (1981). "Chinazolinone, 2. Mitt: Synthese Und Einige Reaktionen Von 2-Azidomethyl-3-Aryl-4-Chinazolinonen," *Monatshefte für Chemie* 112(10):1195-1202. (English translation of abstract only).
Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
El-Fattah et al., Indian J Hetercyclic Chemistry (1995) 4:199-202.
El-Feky, S.A. et al. (1985). "Synthesis of Certain New Sulfur-Containing Quinazolinone Derivatives Likely to Possess CNS Depressant Action," *Egyptian Journal of Pharmaceutical Sciences* 24(1-4):39-47.
El-Feky et al., Chemical Abstracts (1987) 106(13):650.
El-Feky et al., Chemical Abstracts (1999) 131(23):497.
El-Feky, S.A. (Aug. 1998). "Novel Quinazolinones From 2-Cyanomethyl-3-Phenyl-4(3H) Quinazolinone," *Bollettino Chimico Farmaceutico* 137(7):286-289.
Engelman et al., Nature Reviews (2006) 7:606-619.

(56) References Cited

OTHER PUBLICATIONS

Environmental Protection Agency, EPA-Radiation Information (EPA's Radiation Protection Program:lnformation) "Ionizing Radiation Fact Sheet Series No. 1" (May 1998) Retrieved on Apr. 21, 2004: http://www.epa.gov/radiation/docs/ionize/ionize.htm.
Erbagci et al., Clin. Biochem. (2001) 34:645-650.
Estey, Cancer (2001) 92:1059-1073.
Etzioni, Pediatr. Res. (1996) 39:191-198.
European Search Report mailed Mar. 29, 2011, for EP Patent Application No. 10163434.3, filed on Apr. 24, 2001, 9 pages.
European Search Report dated Jun. 6, 2013 for EP Patent Application No. 13150110.8, filed May 12, 2005, 6 pages.
Extended European Search Report mailed Dec. 10, 2013, for EP Patent Application No. 13150110.8, filed May 12, 2005, 10 pages.
Evarts, J.B. et al. (2010). "Discovery and Synthesis of CAL-101, a Potent and Selective Inhibitor of the Phosphatidylinositol 3-Kinase P110δ Isoform," Calistoga Pharmaceuticals Poster, PacifiChem International Chemistry Conference, Dec. 15-20, 2010, 1 page.
Faffe et al., Eur. Respir. J. (2000) 15:85-91.
Fantl et al., Ann. Rev. Biochem. (1993) 62:453-481.
Faust et al., Blood (2000) 96:719-726.
Final Office Action from U.S. Appl. No. 10/918,803, mailed on Jan. 8, 2009.
Final Office Action from U.S. Appl. No. 11/129,006, mailed on Oct. 5, 2010.
Final Office Action from U.S. Appl. No. 11/596,092, mailed on May 18, 2010.
Final Office Action mailed on Oct. 24, 2011, for U.S. Appl. No. 12/732,128, filed on Mar. 25, 2010, 8 pges.
Final Office Action mailed on Feb. 15, 2012, for U.S. Appl. No. 12/732,124, filed on Mar. 25, 2010, 12 pages.
Final Office Action mailed on Jun. 7, 2012, for U.S. Appl. No. 11/129,006, filed on May 12, 2005, 14 pages.
Final Office Action mailed on Jul. 9, 2013, for U.S. Appl. No. 13/399,828, filed on Feb. 17, 2012, 6 pages.
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p110δ Isoform of Phosphatidylinositol 3-Kinase (P13K), in Patients with Select Hematologic Malignancies," Journal of Clinical Oncology 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," Blood 114(22):380, Abstract 922.
Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," Haematologica 94(s2):303, Abstract 0744.
Folkman, Curr. Mol. Med. (2003) 3:643-651.
Folkman, Nat. Med. (1995) 1:27-31.
Fraser et al., Science (1991) 251:313-316.
Frey et al., Lancet (2008) 372(9643):1088-1099 (abstract).
Freyssinier et al., Br. J. Haematol. (1999) 106:912-922.
Fruman et al., Ann. Rev. Biochem. (1998) 67:481-507.
Fruman et al., Semin. Immunol. (2002) 14:7-18.
Furman, R.R. (Jul. 2010). "New Agents in Early Clinical Trials for CLL Therapy," Clinical Advances in Hematology & Oncology 8(7):475-476.
Garcia-Barros et al., Science (2003) 300:1155-1159.
Genbank Accession No. AK040867, last updated Sep. 19, 2008, located at <http://www.ncbi.nlm.nih.gov.nuccore/26334014>, last visited on Apr. 16, 2010, 6 pages.
GenBank Accession No. AR255866, last updated Dec. 20, 2002, located at <http://www.ncbi.nlm.nih.gov.nuccore/27305059>, last visited on Apr. 16, 2010, 2 pages.
GenBank Accession No. BC035203, last updated Aug. 11, 2006, located at <http://www.ncbi.nlm.nih.gov/nuccore/23270986>, last visited on Apr. 16, 2010, 5 pages.
GenBank Accession No. NM_005026, last updated Apr. 11, 2010, located at <http://www.ncbi.nlm.nih.gov/nuccore/15654404>, last visited Apr. 16, 2010, 7 pages.
GenBank Accession No. NM_008840, last updated on Mar. 5, 2010, located at <http://www.ncbi.nlm.nih.gov/nuccore/255708435>, last visited on Apr. 16, 2010, 5 pages.
GenBank Accession No. U57843, last updated on May 9, 1997, located at <http://www.ncbi.nlm.nih.gov/nuccore/U57843>, last visited on Aug. 9, 2011, 2 pages.
GenBank Accession No. U86453, last updated on Jul. 7, 1998, located at <http://www.ncbi.nlm.nih.gov/nuccore/2317893>, last visited on Apr. 16, 2010, 3 pages.
GenBank Accession No. U86587, last updated Jul. 7, 1998, located at <http://www.ncbi.nlm.nih.gov/nuccore/2331237>, last visited on Apr. 16, 2010, 3 pages.
GenBank Accession No. XM_345606, last updated Jun. 22, 2006, located at <http://www.ncbi.n1m.nih.gov/nuccore/109475856?report=genbank>, last visited on Apr. 16, 2010, 3 pages.
GenBank Accession No. Y10055, last updated Oct. 7, 2008, located at <http://www.ncbi.nlm.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Green, S.J. et al. (1994). "Oxidative Metabolism of Murine Macrophages," Chapter 14, Unit 14.5 in Current Protocols in Immunology, vol. 3, John Wiley & Sons, Inc., pp. 14.5.1-14.5.11.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) 9th ed., pp. 11-16.
Harlan, Haematology 96, the Education Program Book of the 26th Congress of the International Society of Haematology. Singapore, 1996.
Harning et al., Transplantation (1991) 52:842-845.
Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
Hattori, H. et al. (May/Jun. 2010). "Reactive Oxygen Species as Signaling Molecules in Neutrophil Chemotaxis," Communicative and Integrative Biology 3(3):278-281.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.
Heit et al., J. Cell Biol. (2002) 159:91-102.
Hellman, Cancer: Principles and Practice of Oncology (1993) 4th ed., vol. 1:248-275.

(56) References Cited

OTHER PUBLICATIONS

Herman, S.E.M. et al. (Sep. 23, 2010). "Phosphatidylinositol 3-Kinase-δ Inhibitor CAL-101 Shows Promising Preclinical Activity in Chronic Lymphocytic Leukemia by Antagonizing Intrinsic and Extrinsic Cellular Survival Signals," Blood 116(12):2078-2088.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Horgan et al., Am. J. Physiol. (1991) 261:H1578-H1584.
Hsieh, S.N. (2003). "Identification of PI3Kγ in Endothelial Cells and Its Involvement in Sphingosine 1-Phosphate Mediated Endothelial Cell Migration," Dissertation, Friedrick Schiller University, Jena, Germany, 104 pages.
Hu et al., Mol. Cell. Biol. (1993) 13:7677-7688.
Hu et al., Science (1995) 268:100-102.
Hunter, Cell (1995) 83:1-4.
Hussong et al., Blood (2000) 95:309-313.
Ikeda, H. et al. (Feb. 2009). "CAL-101: A Selective Inhibitor of P13K p110δ for the Treatment of Multiple Myeloma," *Clinical Lymphoma and Myeloma* 9(Supp. 1):S98-S99.
Ikeda, H. et al. (Nov. 16, 2008). "CAL-101, a Specific Inhibitor of the p110δ Isoform of Phosphatidylinositide 3-Kinase Induces Cytotoxicity in Multiple Myeloma (MM)," *Blood* 112(11):950, Abstract No. 2753.
Ikeda, H. et al. (Sep. 2, 2010). "PI3K/p110δ is a Novel Therapeutic Target in Multiple Myeloma," *Blood* 116(9):1460-1468.
International Preliminary Report on Patentability for PCT/US2006/005621, issued on Aug. 21, 2007, 8 pages.
International Search Report for International (PCT) Patent Application Serial No. PCT/US2004/026436, dated Dec. 2, 2004.
International Search Report for International (PCT) Patent Application Serial No. PCT/US2004/029561, dated May 25, 2005.
International Search Report for International (PCT) Patent Application Serial No. PCT/US2004/026834, dated Nov. 29, 2004.
International Search Report for International (PCT) Patent Application Serial No. PCT/US2004/037860, dated May 6, 2005.
International Search Report mailed on Aug. 29, 2005, for PCT Application No. PCT/US2005/016778, filed on May 12, 2005, 4 pages.
International Search Report mailed on Sep. 15, 2006, for PCT Application No. PCT/US2006/005621, filed on Feb. 16, 2006, 4 pages.
International Search Report mailed on Jun. 27, 2013, for PCT Patent Application No. PCT/US2013/029157, filed on Mar. 5, 2013, 4 pages.
Interview Summary from U.S. Appl. No. 10/918,825, mailed on Jun. 14, 2006.
Ishida-Okawara, A. et al. (Dec. 12, 1996). "Modulation of Degranulation and Superoxide Generation in Human Neutrophils by Unsaturated Fatty Acids of Odd Carbon Numbers," *BioChimica et Biophysica Acta* 1314(3):239-246.
Ismail and Sayed, Indian Journal of Chemistry (1982) 21B(5):461-462.
Ismail et al., Chemical Abstracts (1983) vol. 98, No. 1, p. 406.
Isobe et al., Science (1992) 255:1125-1127.
Johnson et al., Intl. J. Rad. One. Biol. Phys. (1976) 1:659-670.
Johnson et al., J. Endourol. (2003) 17:557-562.
Jordan, Nature Reviews: Drug Discovery (2003) 2:205.
Jou et al., Mol. Cell. Biol. (2002) 22:8580-8591.
Kahl, B.S. (May 2010). "Novel Agents for Non-Hodgkin Lymphoma," *Clinical Advances in Hematology & Oncology* 8(5)(Suppl. 10):10-15.
Kakimoto et al., Cell. Immunol. (1992) 142:326-337.
Kallman et al., Canc. Res. (1972) 32:483-490.
Kandel et al., Exp. Cell Res. (1999) 253:210-229.
Kawasaki et al., J. Immunol. (1993) 150:1074-1083.
Kim et al., Endocrin. (2000) 141:1846-1853.
Kim, Retrieved from the Internet on Apr. 13, 2004: URL: http://www.math.umn.edu/~yjkim/biopaper/timy,html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Lannutti, B.J. et al. (Apr. 2009). "CAL-101, a Specific PI3K p110δ Inhibitor for the Treatment of Hematological Maglignancies," *Proceedings of the American Association for Cancer Research* 50:1400, Abstract No. #SY32-2.
Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," *Blood* 112(11):12, Abstract No. 16.
Lannutti, B.J. et al. (Nov. 20, 2009). "CAL-101, an Oral P110δ Selective Phosphatidylinositol-3-Kinase (PI3K) Inhibitor for the Treatment of B Cell Malignancies Inhibits PI3K Signaling, Cellular Viability and Protective Signals of the Microenvironment," *Blood* 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," *Haematologica* 95(52):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," *Haematologica* 94(52):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172 :7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.
Marley et al., Br. J. Haematol. (May 2004) 125:500-511.
May, S.E. et al. (Nov. 16, 2008). "CAL-101, a Selective Inhibitor of the p110δ Isoform of Phosphatidylinositol 3-Kinase, Effectively Induces Apoptosis in Primary Chronic Lumphocytic Leukemia Cells Providing a Novel Therapeutic Strategy for the Treatment of this Disease," *Blood* 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.

(56) References Cited

OTHER PUBLICATIONS

Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
Ninomiya et al., J. Biol. Chem. (1994) 269:22732-22737.
Non Final Office Action from U.S. Appl. No. 11/596,092, mailed on Dec. 24, 2009.
Non-Final Office Action from U.S. Appl. No. 09/841,341, mailed on Apr. 25, 2002.
Non-Final Office Action from U.S. Appl. No. 10/027,591, mailed on Feb. 26, 2003.
Non-Final Office Action from U.S. Appl. No. 10/918,803, mailed on Apr. 1, 2008.
Non-Final Office Action from U.S. Appl. No. 10/918,803, mailed on Mar. 16, 2010.
Non-Final Office Action from U.S. Appl. No. 10/918,825, mailed on Nov. 7, 2005.
Non-Final Office Action from U.S. Appl. No. 11/110,204, mailed on Aug. 5, 2008.
Non-Final Office Action from U.S. Appl. No. 11/110,204, mailed on Feb. 4, 2010.
Non-Final Office Action from U.S. Appl. No. 11/110,204, mailed on Jun. 17, 2009.
Non-Final Office Action from U.S. Appl. No. 11/129,006, mailed on Dec. 15, 2009.
Non-Final Office Action mailed on Jan. 20, 2012, for U.S. Appl. No. 13/163,597, filed Jun. 17, 2011, 14 pages.
Non-Final Office Action mailed on Oct. 17, 2011, for U.S. Appl. No. 12/732,124, filed Mar. 25, 2010, 8 pages.
Non-Final Office Action from U.S. Appl. No. 11/596,092, mailed on Jun. 10, 2009.
Non-Final Office Action from U.S. Appl. No. 11/884,566, mailed on Aug. 3, 2010.
Non-Final Office Action mailed on Jun. 28, 2011, for U.S. Appl. No. 12/732,124, filed on Mar. 25, 2010, 11 pages.
Non-Final Office Action mailed on Aug. 2, 2012, for U.S. Appl. No. 12/575,277, filed Oct. 7, 2009, 8 pages.
Non-Final Office Action mailed on Aug. 7, 2012, for U.S. Appl. No. 12/575,367, filed Oct. 7, 2009, 9 pages.
Non-Final Office Action mailed on Feb. 13, 2013, for U.S. Appl. No. 13/247,962, filed Sep. 28, 2011, 21 pages.
Non-Final Office Action mailed on Mar. 1, 2013, for U.S. Appl. No. 13/399,828, filed Feb. 17, 2012, 6 pages.
Non-Final Office Action mailed on Mar. 25, 2013, for U.S. Appl. No. 13/728,807, filed Dec. 27, 2012, 13 pages.
Non-Final Office Action mailed on Jun. 26, 2013, for U.S. Appl. No. 13/765,610, filed Feb. 12, 2013, 9 pages.
Non-Final Office Action mailed on Jun. 25, 2014, for U.S. Appl. No. 14/049,154, filed Oct. 8, 2013, 15 pages.
Non-Final Office Action mailed on Jun. 25, 2014, for U.S. Appl. No. 14/049,163, filed Oct. 8, 2013, 15 pages.
Notice of Allowance from U.S. Appl. No. 09/841,341, mailed on Oct. 7, 2002.
Notice of Allowance from U.S. Appl. No. 10/027,591, mailed on Jul. 29, 2003.
Notice of Allowance from U.S. Appl. No. 10/337,192, mailed on Mar. 11, 2004.
Notice of Allowance from U.S. Appl. No. 10/697,912, mailed on Dec. 30, 2004.
Notice of Allowance mailed on Nov. 8, 2010, for U.S. Appl. No. 11/110,204, filed on Apr. 20, 2005, 6 pages.
Notice of Allowance mailed on Jun. 26, 2012, for U.S. Appl. No. 12/732,124, filed Mar. 25, 2010, 11 pages.
Notice of Allowance mailed on Nov. 13, 2012, for U.S. Appl. No. 12/732,124, filed Mar. 25, 2010, 11 pages.
Notice of Allowance mailed on Feb. 21, 2013, for U.S. Appl. No. 12/575,367, filed Oct. 7, 2009, 5 pages.
Notice of Allowance mailed on May 20, 2013, for U.S. Appl. No. 13/730,276, filed Dec. 28, 2012, 7 pages.
Notice of Allowance mailed on Jul. 8, 2013, for U.S. Appl. No. 13/728,807, filed on Dec. 27, 2012, 9 pages.
Notice of Allowance mailed on Jul. 8, 2013, for U.S. Appl. No. 13/730,256, filed Dec. 28, 2012, 9 pages.
Notice of Allowance mailed on Aug. 28, 2013, for U.S. Appl. No. 12/575,277, filed Oct. 7, 2009, 6 pages.
Notice of Allowance mailed on Sep. 19, 2013, for U.S. Appl. No. 13/399,828, filed Feb. 17, 2012, 6 pages.
Notice of Allowance mailed on Oct. 3, 2013, for U.S. Appl. No. 13/247,962, filed Sep. 28, 2011, 9 pages.
Notice of Allowance mailed on Oct. 18, 2013, for U.S. Appl. No. 13/765,610, filed Feb. 12, 2013, 10 pages.
Notice of Allowance mailed on Feb. 21, 2014, for U.S. Appl. No. 13/765,610, filed Feb. 12, 2013, 9 pages.
Notice of Allowance mailed on Jun. 16, 2014, for U.S. Appl. No. 13/786,222, filed Mar. 5, 2013, 12 pages.
Notice of Allowance mailed on Oct. 9, 2014, for U.S. Appl. No. 14/049,154, filed Oct. 8, 2013, 8 pages.
Notice of Allowance mailed on Oct. 10, 2014, for U.S. Appl. No. 14/049,163, filed Oct. 8, 2013, 8 pages.
Notice of Reexamination for Chinese Patent Application No. 0811654.X, mailed Nov. 5, 2009; 7 pages.
Notice Regarding Non-Compliant Amendment from U.S. Appl. No. 10/918,803, mailed on Nov. 19, 2009.
Notification of Reasons for Rejection for Japanese Patent Application No. 2003-537642, mailed on May 26, 2009, 4 pages.
Office Action for European Patent Application No. 04 816 855.3, mailed on Oct. 21, 2008, 4 pages.
Office Action for European Patent Application No. 01 928 855.4, mailed on Feb. 26, 2009, 3 pages.
Office Action for European Patent Application No. 01 928 855.4, mailed on Nov. 15, 2007, 4 pages.
Office Action for European Patent Application No. 01 928 855.4, mailed on Mar. 29, 2006, 6 pages.
Office Action for European Patent Application No. 01 928 855.4, mailed on Jul. 13, 2004, 5 pages.
Office Action for European Patent Application No. 02 757 407.8, mailed on Oct. 6, 2009, 3 pages.
Office Action for European Patent Application No. 02 757 407.8, mailed on Jul. 1, 2009, 2 pages.
Office Action for European Patent Application No. 02 757 407.8, mailed on Oct. 21, 2008, 3 pages.
Office Action for European Patent Application No. 02 757 407.8, mailed on Jun. 6, 2007, 2 pages.
Office Action for European Patent Application No. 02 757 407.8, mailed on Jan. 24, 2006, 3 pages.
Office Action for European Patent Application No. 04 816 855.3, mailed on Feb. 2, 2011, 4 pages.
Office Action for European Patent Application No. 05 752 122.1, mailed on Dec. 28, 2010, 4 pages.
Office Action for European Patent Application No. 05 752 122.1, mailed on Mar. 25, 2013, 4 pages.
Office Action for European Patent Application No. 04 810 878.1, mailed on Sep. 10, 2010, 4 pages.
Ohno-Matsui et al., Invest. Ophthalmol. Vis: Sci. (2003) 44:5370-5375.
Okkenhaug et al., Science (2002) 297:1031-1034.
Oppenheimer-Marks et al., J. Clin. Invest. (1998) 101:1261-1272.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Parasharya et al., Chemical Abstracts (1994) vol. 121, No. 9, p. 1065.
Park, S. et al. (2010). "Role of the PI3K/AKT and mTOR Signaling Pathways in Acute Myeloid Leukemia," *Haematologica* 95(5):819-829.

(56) References Cited

OTHER PUBLICATIONS

Parker, Current Biology (1995) 5:577-579.
Passegue et al., Proc. Natl. Acad. Sci., (USA) (2003) 100 Supp. 1:11842-11849.
Patani, G.A. et al. (1996), "Bioisosterism: A Rational Approach in Drug Design," *Chem Rev.* 96(8):3147-3176.
Pierce et al., J. Biol. Chem. (1997) 272:21096-21103.
Plows et al., J. Immunol. (1999) 162(2):1018-1023.
Podsypanina et al., Proc. Natl. Acad. Sci. (USA) (2001) 98:10320-10325.
Psychoyos et al., J. Immunol. Methods (1991) 137:37-46.
Puri et al., Blood (2005) 106(1):150-157, 144.
Puri et al., Blood (May 2004) 103:3448-3456.
Puri, K. et al. (Jul. 18-23, 2004). "A Role for Phosphoinositide 3-Kinase δ in Neutrophil Trafficking," Immunology 2004: Cytokine Network, Regulatory Cells, Signaling, and Apoptosis: Collection of Free Papers Presented at the 12th International Congress of Immunology and 4th Annual Conference of FOCIS Medimond International Proceedings in Montreal, Canada on Jul. 18, 23, 2004, pp. 303-307.
Quirici et al., Br. J. Haematol. (2001) 115:186-194.
Rada, B.K. et al. (Nov. 1, 2004, e-published Jul. 13, 2004). "Dual Role of Phagocytic NADPH Oxidase in Bacterial Killing," *Blood* 104(9):2947-2953.
Rameh et al., Cell (1995) 83:821-830.
Rameh et al., J. Biol. Chem. (1999) 274:8347-8350.
Rathman et al., J. Org. Chem. (1980) 45:2169-2176.
Remington'S Pharmaceutical Sciences (1990) 18th Ed., Chapter 89, pp. 1435-1712 Table of Contents Only.
Ren et al., Curr. Drug Targets Inflamm. Allergy (2003) 2(3):242-256.
Request for Continued Examination and Amendment Under 37 C.F.R. § 1.116 from U.S. Appl. No. 10/918,803, filed on May 7, 2009.
Response to Election of Species Requirement from U.S. Appl. No. 10/918,803, filed Jun. 27, 2007.
Response to Non-Final Office Action from U.S. Appl. No. 10/918,803, filed Dec. 18, 2009.
Response to Non-Final Office Action filed on Sep. 16, 2010, for U.S. Appl. No. 10/918,803, filed on Aug. 13, 2004, 25 pages.
Response to Restriction Requirement from U.S. Appl. No. 10/918,803, filed Jan. 4, 2008.
Response to Restriction Requirement from U.S. Appl. No. 11/129,006, filed on May 12, 2009.
Response to Restriction Requirement from U.S. Appl. No. 11/137,901, filed on Feb. 6, 2008.
Response to Restriction Requirement from U.S. Appl. No. 11/596,092, filed on May 27, 2009.
Response to Rule 312 Communication mailed on Oct. 4, 2012, for U.S. Appl. No. 12/732,124, filed on Mar. 25, 2010, 7 pages.
Restriction Requirement from U.S. Appl. No. 10/918,803, mailed on Jun. 12, 2009.
Restriction Requirement from U.S. Appl. No. 10/918,803, mailed on Mar. 13, 2007.
Restriction Requirement from U.S. Appl. No. 10/918,803, mailed on Sep. 7, 2007.
Restriction Requirement from U.S. Appl. No. 11/110,204, mailed on Mar. 10, 2008.
Restriction Requirement from U.S. Appl. No. 11/129,006, mailed on Nov. 12, 2008.
Restriction Requirement from U.S. Appl. No. 11/137,901, mailed on Aug. 6, 2007.
Restriction Requirement from U.S. Appl. No. 11/137,901, mailed on May 23, 2008.
Restriction Requirement from U.S. Appl. No. 11/596,092, mailed on Jan. 28, 2009.
Restriction Requirement from U.S. Appl. No. 11/884,566, mailed on Apr. 5, 2010.
Restriction Requirement mailed on Oct. 14, 2010, for U.S. Appl. No. 12/732,124, filed on Mar. 25, 2010, 9 pages.
Restriction Requirement mailed on Dec. 1, 2011, for U.S. Appl. No. 13/163,597, filed on Jun. 17, 2011, 7 pages.
Restriction Requirement mailed on Jun. 7, 2012, for U.S. Appl. No. 13/399,828, filed on Feb. 17, 2012, 5 pages.
Restriction Requirement mailed on Jul. 17, 2012, for U.S. Appl. No. 13/247,962, filed on Sep. 28, 2011, 27 pages.
Restriction Requirement mailed on Sep. 11, 2012, for U.S. Appl. No. 13/399,828, filed on Feb. 17, 2012, 7 pages.
Restriction Requirement mailed on Feb. 3, 2014, for U.S. Appl. No. 13/786,222, filed on Mar. 5, 2013, 17 pages.
Reyes et al., J. Clin. Invest. (2002) 109:337-346.
Rickert et al., Trends Cell Biol. (2000) 10:466-473.
Riesterer, Intl J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., EMBO J. (1996) 15:2442-2451.
Roth et al., J. Immunol. Methods (1995) 188:97-116.
Rudd, Immunity (1996) 4:527-534.
Rupnick et al., Proc. Nat'l. Acad. Sci. (USA) (2002) 99:10730-35.
Sadhu et al., J. Immunol. (2003) 170:2647-2654.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schimmer et al., J. Immunol. (1998) 160:1466-1471.
Schuch et al., Blood (2002) 100:4622-4628.
Schueneman et al., Canc. Res. (2003) 63:4009-4016.
Second Preliminary Amendment and Response to Notice to File Missing Parts of Nonprovisional Application from U.S. Appl. No. 12/575,277, filed on Jan. 20, 2010.
Second Preliminary Amendment and Response to Notice to File Missing Parts of Nonprovisional Application from U.S. Appl. No. 12/575,367, filed on Jan. 20, 2010.
Second Preliminary Amendment from U.S. Appl. No. 11/110,204, filed on Aug. 24, 2007.
Second Preliminary Amendment from U.S. Appl. No. 11/884,566, filed on May 13, 2008.
Sengupta et al., Circulation (2003) 107:2955-2961.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Song et al., Canc. Res. (1974) 34:2344-2350.
Springer, Cell (1994) 76:301-314.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed on Oct. 27, 2009.
Supplemental Notice of Allowance from U.S. Appl. No. 10/337,192, mailed on Jun. 29, 2004.
Tager et al., J. Exp. Med. (2000) 192:439-446.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000), 238:59-68.
Tan, J. et al. (Sep. 1, 2004). "A Specific Antagonist of the p110-Delta Catalytic Component of PI3 Kinase, IC486068, Enhances Radiation-Induced Tumor Vascular Destruction," *International Journal of Radiation: Oncology Biology Physics* 60(1):S195.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).

(56) References Cited

OTHER PUBLICATIONS

The Merck Manual, 17th ed, (1999) p. 1001.
Thelan et al., Proc. Natl. Acad. Sci. (USA) (1994) 91:4960-4964.
Ting et al., Int. J. Rad. Biol. (1991) 60:335-339.
Vacca et al., Blood (1999) 9:3064-3073.
Van Dijk et al., Blood (2000) 96:3406-3413.
Van Eeden, S.F. et al. (Dec. 17, 1999). "The Use of Flow Cytometry to Measure Neutrophil Function," *Journal Immunol Meth* 232:23-43.
Vanhaesebroeck et al., FASEB J. (1996) 10:A1395, Abst. No. 2280.
Vanhaesebroeck et al., Proc. Natl. Acad. Sci., (USA) (1997) 94:4330-4335.
Vanhaesebroeck et al., TIBS (1997) 22:267-272.
Vermes et al., J. Immunol. Meth. (1995) 184:39-51.
Vippagunta, S.R. et al. (2001). "Crystalline Solids," *Advanced Drug Delivery* 48:3-26.
Vivanco et al., Nat. Rev. Cancer (2002) 2:489-501.
Vlahos et al., J. Immunol. (1995) 154:2413-2422.
Volinia et al., EMBO J. (1995) 14:3339-3348.
Volinia et al., Genomics (1994) 24:472-477.
Volinia et al., Oncogene (1992) 7:789-793.
Webb, H.K. et al. (Apr. 2009). "CAL-101, a Potent and Selective Inhibitor of the Class 1 Phosphatidylinositol 3 Kinase (PI3K) p110δ: Preclinical Summary," *Proceedings of the American Association for Cancer Research* 50:894-895, Abstract No. #3703.
Wegner et al., Lung (1992) 170:267-279.
Wegner et al., Science (1990) 247:456-459.
Weiner et al., Nat. Cell Biol. (1999) 1:75-81.
Weyand et al., Arthritis & Rheumatism (2000) 43:1041-1048.
Williams, D.A. et al. (2002). *Foye's Principles of Medicinal Chemistry*, Lippincott, Williams & Wilkins, Baltimore MD, Fifth Edition, pp. 50 and 59-61.
Williams, Methods Mol. Med. (2004) 98:207-216.
Williams et al., Chem. Biol. (2010) 17:123-134.
Wolff, ed., Burger's Medicinal Chemistry and Drug Discovery, 5th edition (1996) vol. 1, New York: John Wiley & Sons, pp. 975-977.
Written Opinion mailed on Jun. 27, 2013 for PCT Patent Application No. PCT/US2013/029157, filed on Mar. 5, 2013, 6 pages.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.
Zu, Y-L et al. (1998). "p38 Mitogen-Activated Protein Kinase Activation is Required for Human Neutrophil Function Triggered by TNF-α or FMLP Stimulation", *J Immunol* 160:1982-1989.
U.S. Appl. No. 14/284,331, filed on May 21, 2014, by Kesicki et al. (copy not attached).
Brittain, H.G. (2009) "The Theory and Principles of Polymorphic Systems" *Polymorphism in Pharmaceutical Solids*, Second Edition Informs Healthcare, NY., pp. 1-4, 15-19, 318-430.

Byrn, S. et al. (1995) "Pharmaceutical Solids: A Strategic Approach to Regulatory Considerations" *Pharmaceutical Research* 12(7)945-954.
Caira, M.R. (Jan. 1, 1998). "Crystalline Polymorphism of Organic Compounds", *Topics in Current Chemistry* 198:163-208.
Extended European Search Report and European Search Opinion dated Oct. 8, 2015, for EP Patent Application No. 13757230.1, filed on Mar. 5, 2013, 6 pages.
First Office Action mailed Jul. 2, 2015, for Chinese Patent Application No. 201380011784.1, internationally filed on May 3, 2015, 16 pages.
First Office Action mailed Sep. 17, 2015, for Eurasian Patent Application No. 201491473/28, filed on Mar. 5, 2013, 2 pages, 2 pages English translation, (4 pages total).
First Examination Report mailed Jun. 4, 2015, for New Zealand Patent Application No. 695440, Internationally filed on Mar. 5, 2013, 2 pages.
Hatsu, I.S. (May 1, 2001) No. 568, 45 pages, English translation 1 page, 46 pages total.
Notice of Allowance mailed on Mar. 16, 2016, for Australian Patent Application No. 2015252058, Internationally filed on Mar. 5, 2013, 2 pages.
Notice Prior to Exam mailed on Sep. 7, 2015, for Israeli Patent Application No. 237644, Internationally filed on Mar. 5, 2013, 3 pages.
Office Action dated Jan. 27, 2015, for Vietnam Patent Application No. Jan. 2014-02846, Internationally filed on Mar. 5, 2013, 1 page.
Office Action mailed Nov. 26, 2015, for Eurasian Patent Application No. 201491473/28, Internationally filed on Mar. 5, 2013, 1 page.
Office Action mailed Mar. 9, 2016, for Chinese Patent Application No. 201380011784.1, Internationally filed on Mar. 5, 2013, 12 pages.
Office Action mailed Apr. 12, 2016, for Japanese Patent Application No. 2014-561048, Internationally filed on Mar. 5, 2013, 7 pages.
Oshima, H. (2007) "Crystallization of Polymorphs and Pseudo-Polymorphs and Its Control," *Pharm Stage* 6(10)48-53, English translation of the introduction with certification.
Search Report dated Apr. 24, 2015, for Singapore Patent Application No. 11201405446P, filed on Mar. 5, 2013, 2 pages.
Supplementary European Search Report dated Oct. 27, 2015, for European Patent Application No. 13757230.1, Internationally filed on Mar. 5, 2013, 1 page.
Takata, N. (2007) "API Form Screening and Selection in Drug Discovery Stage," *Pharm Stage* 6(10)20-25, English translation of the introduction with certification.
Written Opinion dated May 27, 2015, for Singapore Patent Application No. 11201405446P, internationally filed on Mar. 5, 2013, 6 pages.
Written Opinion dated Aug. 12, 2015, for Singapore Patent Application No. 11201405446P, internationally filed on Mar. 5, 2013, 6 pages.
Yamano, M. (2007) "Approach to Crystal Polymorph in Process Research of New Drug," Journal of the Society of Synthetic Organic Chemistry 65(9)907-944, English translation of the introduction with certification.
Written Opinion dated Jun. 21, 2016 for Singapore Patent Application No. 11201405446P.
Office Action dated Jul. 14, 2016 for Ukraine Patent Application No. 201409188.
Office Action dated Jun. 1, 2016 for Thailand Patent Application No. 1401004922.

POLYMORPHIC FORMS OF (S)-2-(1-(9H-PURIN-6-YLAMINO)PROPYL)-5-FLUORO-3-PHENYLQUINAZOLIN-4(3H)-ONE

CROSS REFERENCE TO RELATED APPLICATIONS

This application is a divisional of U.S. patent application Ser. No. 13/786,222, filed Mar. 5, 2013, which claims the benefit of U.S. provisional patent application Ser. No. 61/606,870, filed Mar. 5, 2012, the disclosures of which are hereby incorporated herein by reference in their entireties.

FIELD

Provided are polymorphs of (S)-2-(1-(9H-purin-6-ylamino)propyl)-5-fluoro-3-phenylquinazolin-4(3H)-one, compositions thereof, methods for their preparation, and methods for their use.

BACKGROUND

Cell signaling via 3'-phosphorylated phosphoinositides has been implicated in a variety of cellular processes, e.g., malignant transformation, growth factor signaling, inflammation, and immunity. See Rameh et al., J. Biol. Chem., 274:8347-8350 (1999) for a review. The enzyme responsible for generating these phosphorylated signaling products is phosphatidylinositol 3-kinase (PI 3-kinase; PI3K). PI3K originally was identified as an activity associated with viral oncoproteins and growth factor receptor tyrosine kinases that phosphorylates phosphatidylinositol (PI) and its phosphorylated derivatives at the 3'-hydroxyl of the inositol ring. See Panayotou et al., Trends Cell Biol. 2:358-60 (1992).

PI 3-kinase activation is believed to be involved in a range of cellular responses including cell growth, differentiation, and apoptosis. See Parker et al., Curr. Biol., 5:577-99 (1995); Yao et al., Science, 267:2003-05 (1995). PI 3-kinase also appears to be involved in a number of aspects of leukocyte activation. See e.g., Pages et al., Nature, 369:327-29 (1994); Rudd, Immunity, 4:527-34 (1996); Fraser et al., Science, 251:313-16 (1991).

Several compounds have been identified as PI 3-kinase inhibitors. For example, compounds capable of inhibiting the biological activity of human PI3K, including (S)-2-(1-(9H-purin-6-ylamino)propyl)-5-fluoro-3-phenylquinazolin-4(3H)-one, and their uses are disclosed in U.S. Pat. No. 6,518,277, U.S. Pat. No. 6,667,300, and U.S. Pat. No. 7,932,260. Each of these references is hereby incorporated herein by reference in its entirety.

BRIEF SUMMARY (S)-2-(1-(9H-purin-6-ylamino)propyl)-5-fluoro-3-phenylquinazolin-4(3H)-one, has been chosen for further development. Consequently, it is desired to produce this compound in a form that is bioavailable and stable. In one aspect, provided herein are polymorphs of (S)-2-(1-(9H-purin-6-ylamino)propyl)-5-fluoro-3-phenylquinazolin-4(3H)-one, a compound having the molecular structure:

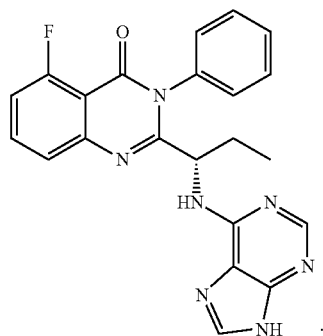 [SMILES: CC[C@H](Nc1ncnc2[nH]cnc12)c1nc2cccc(F)c2c(=O)n1-c1ccccc1]

Specifically, polymorphic Forms I, II, III, IV, V, VI and VII of (S)-2-(1-(9H-purin-6-ylamino)propyl)-5-fluoro-3-phenylquinazolin-4(3H)-one, and methods of making and using these polymorphic forms are provided. Also provided are polymorphic products obtained by the processes (e.g. methods of making). Pharmaceutical compositions comprising one or more polymorphic forms of (S)-2-(1-(9H-purin-6-ylamino)propyl)-5-fluoro-3-phenylquinazolin-4(3H)-one (any one or more of polymorphic Forms I, II, III, IV, V, VI and VII) and a pharmaceutically acceptable carrier are provided. Articles of manufacture and unit dosage forms comprising any one of more of the polymorphic forms of (S)-2-(1-(9H-purin-6-ylamino)propyl)-5-fluoro-3-phenylquinazolin-4(3H)-one (e.g., any one of more of polymorphic Forms I, II, III, IV, V, VI and VII) are provided. Kits comprising any one of more of the polymorphic forms (e.g., polymorphic Forms I, II, III, IV, V, VI and VII of (S)-2-(1-(9H-purin-6-ylamino)propyl)-5-fluoro-3-phenylquinazolin-4(3H)-one), and instructions for use (e.g., instructions for use in PI3K-mediated disorder, such as cancer) are also provided.

These polymorphs are characterized by a variety of solid state analytical data, including for example X-ray powder diffraction pattern (XRPD) and differential scanning calorimetry (DSC).

Provided is a polymorph of (S)-2-(1-(9H-purin-6-ylamino)propyl)-5-fluoro-3-phenylquinazolin-4(3H)-one, wherein the polymorph is Form I having an X-ray powder diffraction pattern substantially as shown in FIG. 1A.

Provided is also a polymorph of (S)-2-(1-(9H-purin-6-ylamino)propyl)-5-fluoro-3-phenylquinazolin-4(3H)-one, wherein the polymorph is Form I having an X-ray powder diffraction pattern that includes characteristic peaks at about 17.7 degrees 2θ and about 24.9 degrees 2θ. In some embodiments, the X-ray powder diffraction pattern further includes any one or more of characteristic peaks at about 14.3 degrees 2θ, about 17.2 degrees 2θ, about 20.9 degrees 2θ, and about 23.9 degrees 2θ. In some embodiments, the polymorphic Form I has a melting temperature of about 254° C. to about 256° C. In one variation, polymorphic Form I has an X-ray powder diffraction pattern that includes any one or more characteristic peaks at about 14.3 degrees 2θ, about 17.2 degrees 2θ, about 17.7 degrees 2θ, about 20.9 degrees 2θ, about 23.9 degrees 2θ, and about 24.9 degrees 2θ; and a melting temperature of about 254° C. to about 256° C.

It should be understood that relative intensities can vary depending on a number of factors, including sample preparation, mounting, and the instrument and analytical procedure and settings used to obtain the spectrum. As such, the peak assignments listed herein (including for polymorphic Form I) are intended to encompass variations of plus or minus 0.2 degrees 2θ.

In some embodiments, the polymorphic Form I described herein is obtained by: a) combining (S)-2-(1-(9H-purin-6-ylamino)propyl)-5-fluoro-3-phenylquinazolin-4(3H)-one with a solvent to form a mixture; b) heating the mixture to form a solution; and c) cooling the heated solution to form the polymorphic Form I. In certain embodiments, the heated solution is cooled to a temperature of at least about 30° C. In other embodiments, the heated solution is cooled to a temperature of at least about 35° C., or between about 30° C. and about 40° C., or between about 30° C. and about 35° C., or between about 35° C. and about 40° C. In some embodiments, polymorphic Form I is further obtained by isolating the solids, such as polymorphic Form I solids, from the cooled solution. In yet other embodiments, polymorphic Form I is further obtained by washing the isolated solids; and drying the washed isolated solids. In some embodiments, the solvent used to obtain polymorphic Form I includes water, an organic solvent, or a mixture thereof. In certain embodiments, the solvent includes water, an alcohol (e.g., methanol, ethanol), or a mixture thereof. In some embodiments, the solvent includes a mixture of alcohol and water in a ratio between 2 to 1 and 10 to 1, or between 4 to 1 and 5 to 1. In certain embodiment, the solvent includes a mixture of alcohol and water in a ratio of 2 to 1, or 2.5 to 1, or 3 to 1, or 3.5 to 1, or 4 to 1, or 4.5 to 1, or 5 to 1. In certain embodiments, the solvent includes a mixture of methanol and water in a ratio between 2 to 1 and 10 to 1, or between 4 to 1 and 5 to 1. In one embodiment, the solvent includes a mixture of methanol and water in a ratio of 2 to 1, or 2.5 to 1, or 3 to 1, or 3.5 to 1, or 4 to 1, or 4.5 to 1, or 5 to 1.

It should be understood, however, one or more of the steps described above to obtain polymorphic Form I may be omitted or the order of the steps may be varied. For example, in other embodiments, polymorphic Form I may be obtained by heating (S)-2-(1-(9H-purin-6-ylamino)propyl)-5-fluoro-3-phenylquinazolin-4(3H)-one prior to combining with a solvent to form a mixture. In yet other embodiments, polymorphic Form I may be obtained by combining (S)-2-(1-(9H-purin-6-ylamino)propyl)-5-fluoro-3-phenylquinazolin-4(3H)-one with a solvent to form a mixture, and cooling the mixture to obtain polymorphic Form I.

In other embodiments, the polymorphic Form I described herein is obtained by: a) combining a salt of (S)-2-(1-(9H-purin-6-ylamino)propyl)-5-fluoro-3-phenylquinazolin-4(3H)-one and a solvent to form an acidic mixture or solution; b) neutralizing the acidic mixture or solution, wherein the neutralized mixture or solution includes free (S)-2-(1-(9H-purin-6-ylamino)propyl)-5-fluoro-3-phenylquinazolin-4(3H)-one; c) heating the neutralized mixture or solution; and d) adding water to the heated mixture or solution to convert at least a portion of the free (S)-2-(1-(9H-purin-6-ylamino)propyl)-5-fluoro-3-phenylquinazolin-4(3H)-one into polymorphic Form I. Optionally, one or more seed crystals of polymorphic Form I may be added to the neutralized mixture or solution before heating. In certain embodiments, the salt of (S)-2-(1-(9H-purin-6-ylamino)propyl)-5-fluoro-3-phenylquinazolin-4(3H)-one is a hydrochloride salt of (S)-2-(1-(9H-purin-6-ylamino)propyl)-5-fluoro-3-phenylquinazolin-4(3H)-one. In some embodiments, the solvent includes water, an alcohol, or a mixture thereof. In certain embodiments, the solvent includes water, ethanol, or a mixture thereof. In some embodiments, the acidic mixture or solution is neutralized using an aqueous sodium carbonate solution. In other embodiments, the neutralized mixture or solution is heated to a temperature between 40° C. and 60° C., or to a temperature of about 50° C.

It should be understood, however, one or more of the steps described above to obtain polymorphic Form I from the salt of (S)-2-(1-(9H-purin-6-ylamino)propyl)-5-fluoro-3-phenylquinazolin-4(3H)-one may be omitted or the order of the steps may be varied. For example, in other embodiments, the salt of (S)-2-(1-(9H-purin-6-ylamino)propyl)-5-fluoro-3-phenylquinazolin-4(3H)-one may be combined with a solvent to form an acidic mixture or solution, and the acidic mixture or solution may be heated before neutralization. In yet other embodiments, the salt of (S)-2-(1-(9H-purin-6-ylamino)propyl)-5-fluoro-3-phenylquinazolin-4(3H)-one may be combined with a solvent to form an acidic mixture or solution, the acidic mixture or solution may then be neutralized, and water may be added to the neutralized mixture or solution to convert at least a portion of the free (S)-2-(1-(9H-purin-6-ylamino)propyl)-5-fluoro-3-phenylquinazolin-4(3H)-one into polymorphic Form I.

Provided is also a polymorph of (S)-2-(1-(9H-purin-6-ylamino)propyl)-5-fluoro-3-phenylquinazolin-4(3H)-one which is bioequivalent to the polymorphic Form I described herein.

In some embodiments, the polymorphic Form I described herein is isolated, e.g., from a mixture or solution comprising (S)-2-(1-(9H-purin-6-ylamino)propyl)-5-fluoro-3-phenylquinazolin-4(3H)-one and one or more impurities. In some embodiments, the polymorphic Form I described herein is a substantially pure polymorph.

Provided is also a composition including the polymorphic Form I described herein, wherein the composition is substantially free of polymorphs other than polymorphic Form I of (S)-2-(1-(9H-purin-6-ylamino)propyl)-5-fluoro-3-phenylquinazolin-4(3H)-one.

In other embodiments of the composition, at least about 95% of the (S)-2-(1-(9H-purin-6-ylamino)propyl)-5-fluoro-3-phenylquinazolin-4(3H)-one present in the composition is polymorphic Form I. In yet other embodiments, at least 96%, at least 97%, at least 98%, or at least 99% of the (S)-2-(1-(9H-purin-6-ylamino)propyl)-5-fluoro-3-phenylquinazolin-4(3H)-one present in the composition is the polymorphic Form I described herein.

In other embodiments of the composition, less than about 5% of the (S)-2-(1-(9H-purin-6-ylamino)propyl)-5-fluoro-3-phenylquinazolin-4(3H)-one present in the composition are polymorphs other than polymorphic Form I. In yet other embodiments, less than about 4%, less than about 3%, less than about 2%, or less than about 1% of the (S)-2-(1-(9H-purin-6-ylamino)propyl)-5-fluoro-3-phenylquinazolin-4(3H)-one present in the composition are polymorphs other than polymorphic Form I.

Provided is also a pharmaceutical composition including polymorphic Form I described herein and one or more pharmaceutically acceptable carriers or excipients.

Provided is also a kit including the polymorphic Form I described herein and packaging. Provided is also a kit including the composition of polymorphic Form I described herein and packaging.

Provided is a method of preparing the polymorphic Form I described herein, by: a) combining (S)-2-(1-(9H-purin-6-ylamino)propyl)-5-fluoro-3-phenylquinazolin-4(3H)-one with a solvent to form a mixture; b) heating the mixture to form a solution; and c) cooling the heated solution to form the polymorphic Form I described herein. In some embodiments, the solution is cooled to a temperature of at least about 30° C. In other embodiments, the heated solution is cooled to a temperature of at least about 35° C., or between about 30° C. and about 40° C., or between about 30° C. and about 35° C., or between about 35° C. and about 40° C. In some embodiments, the method further includes isolating the solids, such as polymorphic Form I solids. In yet other embodiments, the method further includes: washing the isolated solids; and drying the washed isolated solids. In some embodiments, the solvent includes water, an organic solvent, or a mixture thereof. In certain embodiments, the organic solvent is selected from solvent groups such as the alcohols (e.g., methanol, ethanol, propanol, etc.), acetates (e.g., isopropyl acetate, ethyl acetate, etc.), ethers (e.g., methyl t-butyl ether, 2-methyl tetrahydrofuran, etc.), ketones (e.g., methyl ethyl ketone, methyl isobutyl ketone, etc.), other polar aprotics (e.g., dimethylsulfoxide, etc.) and nonpolars (e.g., hexane, heptane, etc.) or a mixture thereof.

It should be understood, however, one or more of the steps of the method to prepare polymorphic Form I may be omitted or the order of the steps may be varied. For example, in other embodiments, the method includes heating (S)-2-(1-(9H-purin-6-ylamino)propyl)-5-fluoro-3-phenylquinazolin-4(3H)-one prior to combining with a solvent to form a mixture. In yet other embodiments, the method includes combining (S)-2-(1-(9H-purin-6-ylamino)propyl)-5-fluoro-3-phenylquinazolin-4(3H)-one with a solvent to form a mixture, and cooling the mixture to obtain polymorphic Form I.

Provided is also a method of preparing the polymorphic Form I described herein, by: a) combining a salt of (S)-2-(1-(9H-purin-6-ylamino)propyl)-5-fluoro-3-phenylquinazolin-4(3H)-one and a solvent to form an acidic mixture or solution; b) neutralizing the acidic mixture or solution, wherein the neutralized mixture or solution includes free (S)-2-(1-(9H-purin-6-ylamino)propyl)-5-fluoro-3-phenylquinazolin-4(3H)-one; c) heating the neutralized mixture or solution; and d) adding water to the heated mixture to convert at least a portion of the free (S)-2-(1-(9H-purin-6-ylamino)propyl)-5-fluoro-3-phenylquinazolin-4(3H)-one into polymorphic Form I. Optionally, one or more seed crystals of polymorphic Form I may be added to the neutralized mixture or solution before heating. In some embodiments, the method further includes isolating the polymorphic Form I. In certain embodiments, the salt of (S)-2-(1-(9H-purin-6-ylamino)propyl)-5-fluoro-3-phenylquinazolin-4(3H)-one is a hydrochloride salt of (S)-2-(1-(9H-purin-6-ylamino)propyl)-5-fluoro-3-phenylquinazolin-4(3H)-one. In some embodiments, the solvent includes water, an alcohol, or a mixture thereof. In certain embodiments, the solvent includes water, ethanol, or a mixture thereof. In some embodiments, the acidic mixture or solution is neutralized using an aqueous sodium carbonate solution. In other embodiments, the neutralized mixture or solution is heated to a temperature between 40° C. and 60° C., or about 50° C.

It should be understood, however, one or more of the steps of the method to prepare polymorphic Form I from the salt of (S)-2-(1-(9H-purin-6-ylamino)propyl)-5-fluoro-3-phenylquinazolin-4(3H)-one may be omitted or the order of the steps may be varied. For example, in other embodiments, the method includes combining the salt of (S)-2-(1-(9H-purin-6-ylamino)propyl)-5-fluoro-3-phenylquinazolin-4(3H)-one with a solvent to form an acidic mixture or solution, heating the acidic mixture or solution, neutralizing the heated acidic mixture or solution, and adding water to the heated mixture or solution to convert at least a portion of the free (S)-2-(1-(9H-purin-6-ylamino)propyl)-5-fluoro-3-phenylquinazolin-4(3H)-one into polymorphic Form I. In yet other embodiments, the method includes combining the salt of (S)-2-(1-(9H-purin-6-ylamino)propyl)-5-fluoro-3-phenylquinazolin-4(3H)-one with a solvent to form an acidic mixture or solution, neutralizing the acidic mixture or solution, and adding water to the neutralized mixture or solution to convert at least a portion of the free (S)-2-(1-(9H-purin-6-ylamino)propyl)-5-fluoro-3-phenylquinazolin-4(3H)-one into polymorphic Form I.

Provided is also a method of treating a patient with a cancer, by administering to the patient a composition comprising the polymorphic Form I described herein and a pharmaceutically acceptable excipient. In some embodiments, the cancer is a hematologic malignancy. In other embodiments, the hematologic malignancy is leukemia, wherein leukemia is non-Hodgkin's lymphoma (NHL) or chronic lymphocytic leukemia (CLL). In particular embodiments, the hematologic malignancy is leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL).

Provided is a polymorph of (S)-2-(1-(9H-purin-6-ylamino)propyl)-5-fluoro-3-phenylquinazolin-4(3H)-one, wherein the polymorph is Form II having an X-ray powder diffraction pattern substantially as shown in FIG. 2A.

Provided is also a polymorph of (S)-2-(1-(9H-purin-6-ylamino)propyl)-5-fluoro-3-phenylquinazolin-4(3H)-one, wherein the polymorph is Form II having an X-ray powder diffraction pattern that includes a characteristic peak at about 18.6 degrees 2θ. In some embodiments, the X-ray powder diffraction pattern further includes characteristic peaks at about 24.3 degrees 2θ and about 14.0 degrees 2θ.

It should be understood that relative intensities can vary depending on a number of factors, including sample preparation, mounting, and the instrument and analytical procedure and settings used to obtain the spectrum. As such, the peak assignments listed herein (including for polymorphic Form II described herein) are intended to encompass variations of plus or minus 0.2 degrees 2θ.

In certain embodiments, polymorphic Form II described herein is obtained by: a) providing a polymorphic Form I of (S)-2-(1-(9H-purin-6-ylamino)propyl)-5-fluoro-3-phenylquinazolin-4(3H)-one; b) grinding the polymorphic Form I; and c) stirring the ground polymorphic Form I in a solvent to form the polymorphic Form II described herein. In one variation, polymorphic Form II described herein is obtained by grinding the polymorphic Form I of (S)-2-(1-(9H-purin-6-ylamino)propyl)-5-fluoro-3-phenylquinazolin-4(3H)-one; and stirring the ground polymorphic Form I in a solvent to form the polymorphic Form II described herein. In some embodiments, polymorphic Form II is obtained by further heating the ground polymorphic Form I stirred in the solvent to form the polymorphic Form II described herein. In some embodiments, polymorphic Form I is ground to a particle size of between about 1 microns to about 10 microns. In some embodiments, polymorphic Form II is obtained by further isolating the polymorphic Form II. In certain embodiments, the stirred mixture is heated at a temperature of less than about 30° C. In one embodiment, the stirred mixture is heated at a temperature of between about 25° C. and about 30° C. In another embodiment, the ground polymorphic Form I is stirred in the solvent at a temperature of between about 10° C. and about 25° C. In some embodiments, the grinding may be performed using any suitable methods or techniques known to one of skill in the art, including for example using a mortar and pestle, a high shear wet mill, a high shear dry mixer, a jet mill, a ball mill, or a combination of methods or techniques. In one embodiment, the grinding is performed using a ball mill. In some embodiments, the solvent includes an organic solvent. In one embodiment, the solvent includes acetone.

It should be understood, however, one or more of the steps described above to obtain polymorphic Form II from polymorphic Form I may be omitted or the order of the steps may be varied. For example, in other embodiments, polymorphic Form I may be combined with a solvent before grinding to obtain the polymorphic Form II.

In some embodiments, the polymorphic Form II described herein is obtained by: a) providing a polymorphic Form I of (S)-2-(1-(9H-purin-6-ylamino)propyl)-5-fluoro-3-phenylquinazolin-4(3H)-one; and b) compressing the polymorphic Form I at a pressure of between about 500 psi and about 5000 psi to convert at least a portion of the polymorphic Form I to the polymorphic Form II described herein. In one embodiment, the polymorphic Form II described herein is obtained by compressing polymorphic Form I at a pressure of between about 500 psi and about 5000 psi to convert at least a portion of the polymorphic Form I of (S)-2-(1-(9H-purin-6-ylamino)propyl)-5-fluoro-3-phenylquinazolin-4(3H)-one to the polymorphic Form II described herein.

In some embodiments, the compressing is performed using a tablet press or a rotary press. In some embodiments, the polymorphic Form I is compressed at a pressure of between 500 psi and 2000 psi, between 1000 psi and 4500 psi, or between 3000 psi and 4500 psi.

Provided is also a polymorph of (S)-2-(1-(9H-purin-6-ylamino)propyl)-5-fluoro-3-phenylquinazolin-4(3H)-one which is bioequivalent to the polymorphic Form II described herein.

In some embodiments, the polymorphic Form II described herein is isolated. In some embodiments, the polymorphic Form II described herein is a substantially pure polymorph.

Provided is also composition comprising the polymorphic Form II described herein, wherein the composition is substantially free of polymorphs other than polymorphic Form II of (S)-2-(1-(9H-purin-6-ylamino)propyl)-5-fluoro-3-phenylquinazolin-4(3H)-one.

In other embodiments, at least about 95% of the (S)-2-(1-(9H-purin-6-ylamino)propyl)-5-fluoro-3-phenylquinazolin-4(3H)-one present in the composition is polymorphic Form II. In yet other embodiments, at least 96%, at least 97%, at least 98%, or at least 99% of the (S)-2-(1-(9H-purin-6-ylamino)propyl)-5-fluoro-3-phenylquinazolin-4(3H)-one present in the composition is the polymorphic Form II described herein.

In other embodiments, less than about 5% of the (S)-2-(1-(9H-purin-6-ylamino)propyl)-5-fluoro-3-phenylquinazolin-4(3H)-one present in the composition are polymorphs other than polymorphic Form II. In yet other embodiments, less than about 4%, less than about 3%, less than about 2%, less than about 1% of the (S)-2-(1-(9H-purin-6-ylamino) propyl)-5-fluoro-3-phenylquinazolin-4(3H)-one present in the composition are polymorphs other than polymorphic Form II.

Provided is also a pharmaceutical composition including the polymorphic Form II described herein and one or more pharmaceutically acceptable carriers or excipients.

Provided is also a kit including the polymorphic Form II and packaging. Provided is also a kit including the composition of polymorphic Form II and packaging.

Provided is a method of preparing the polymorphic Form II described herein, by: a) providing a polymorphic Form I of (S)-2-(1-(9H-purin-6-ylamino)propyl)-5-fluoro-3-phenylquinazolin-4(3H)-one; b) grinding the polymorphic Form I; and c) stirring the ground polymorphic Form I in a solvent to form the polymorphic Form II described herein. In one embodiment, provided is a method for preparing the polymorphic Form II described herein, by grinding the polymorphic Form I of (S)-2-(1-(9H-purin-6-ylamino)propyl)-5-fluoro-3-phenylquinazolin-4(3H)-one; and stirring the ground polymorphic Form I in a solvent to form the polymorphic Form II described herein. In certain embodiments, the polymorphic Form I is ground to a particle size of between about 1 microns to about 10 microns. In some embodiments, the method further includes heating the ground polymorphic Form I stirred in the solvent to form the polymorphic Form II described herein. In some embodiments, the method further includes isolating the polymorphic Form II. In certain embodiments, the stirred mixture is heated at a temperature of less than about 30° C. In one embodiment, the stirred mixture is heated at a temperature of between about 25° C. and about 30° C. In other embodiments, the ground polymorphic Form I is stirred in the solvent at a temperature of between about 10° C. and about 25° C. In some embodiments, the grinding may be performed using any suitable methods or techniques known to one of skill in the art, including for example using a mortar and pestle, a high shear wet mill, a high shear dry mixer, a jet mill, a ball mill, or a combination of methods or techniques. In one embodiment, the grinding is performed using a ball mill. In some embodiments, the solvent includes an organic solvent. In one embodiment, the solvent includes acetone.

It should be understood, however, one or more of the steps of the method to prepare polymorphic Form II from polymorphic Form I may be omitted or the order of the steps may be varied. For example, in other embodiments, polymorphic Form I may be combined with a solvent before grinding to obtain the polymorphic Form II.

Provided is also a method of preparing the polymorphic Form II described herein, by: a) providing a polymorphic Form I of (S)-2-(1-(9H-purin-6-ylamino)propyl)-5-fluoro-3-phenylquinazolin-4(3H)-one; and b) compressing the polymorphic Form I at a pressure of between about 500 psi and 5000 psi to form the polymorphic Form II described herein. In one embodiment, provided is a method of preparing the polymorphic Form II described herein, by compressing the polymorphic Form I of (S)-2-(1-(9H-purin-6-ylamino)propyl)-5-fluoro-3-phenylquinazolin-4(3H)-one at a pressure of between about 500 psi and 5000 psi to form the polymorphic Form II described herein. In some embodiments, the compressing is performed using a tablet press or a rotary press. In some embodiments, the polymorphic Form I is compressed at a pressure of between 500 psi and 2000 psi, between 1000 psi and 4500 psi, or between 3000 psi and 4500 psi.

Provided is also a method of treating a patient with a cancer, by administering to the patient a composition including the polymorphic Form II described herein and a pharmaceutically acceptable carrier or excipient. In some embodiments, the cancer is a hematologic malignancy. In other embodiments, the hematologic malignancy is leukemia, wherein leukemia is non-Hodgkin's lymphoma (NHL) or chronic lymphocytic leukemia (CLL). In particular embodiments, the hematologic malignancy is leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL).

Provided is also a composition comprising a mixture of polymorphic Form I and Form II of (S)-2-(1-(9H-purin-6-ylamino)propyl)-5-fluoro-3-phenylquinazolin-4(3H)-one. In some embodiments, the polymorphic Form I has an X-ray powder diffraction pattern comprising characteristic peaks at about 17.7 degrees 2θ and about 24.9 degrees 2θ; and the polymorphic Form II has an X-ray powder diffraction pattern comprising a characteristic peak at about 18.6 degrees 2θ.

In certain embodiments of the composition, the X-ray powder diffraction pattern for the polymorphic Form I further comprises one or more characteristic peaks at about 14.3 degrees 2θ, about 17.2 degrees 2θ, about 20.9 degrees 2θ, and about 23.9 degrees 2θ. In one embodiment of the composition, the X-ray powder diffraction pattern for the polymorphic Form I has one or more characteristic peaks at about 14.3 degrees 2θ, about 17.2 degrees 2θ, about 17.7 degrees 2θ, about 20.9 degrees 2θ, about 23.9 degrees 2θ, and about 24.9 degrees 2θ.

In some embodiments of the composition, the X-ray powder diffraction pattern for the polymorphic Form II further comprises characteristic peaks at about 24.3 degrees 2θ and about 14.0 degrees 2θ. In one embodiment of the composition, the X-ray powder diffraction pattern for the polymorphic Form I has one or more characteristic peaks at about 14.0 degrees 2θ, about 18.6 degrees 2θ, and about 24.3 degrees 2θ. In certain embodiments of the composition, the polymorphic Form I is present in excess of the polymorphic Form II. In one embodiment of the composition, the polymorphic Form I and polymorphic Form II are present in a ratio of between 99 to 1 and 55 to 45, or a ratio of 99 to 1, 90 to 10, 85 to 15, 80 to 20, 75 to 25, 70 to 30, 65 to 35, 60 to 40, or 55 to 45. In one embodiment, the weight ratio of polymorphic Form I to polymorphic Form II is between 90:1 and 99:1.

Provided is also a composition including a mixture of polymorphic Form I and polymorphic Form II of (S)-2-(1-(9H-purin-6-ylamino)propyl)-5-fluoro-3-phenylquinazolin-4(3H)-one, wherein the polymorphic Form I has an X-ray powder diffraction pattern substantially as shown in FIG. 1A, and wherein the polymorphic Form II has an X-ray powder diffraction pattern substantially as shown in FIG. 2A. In certain embodiments, the composition is substantially free of polymorphs other than polymorphic Form I and polymorphic Form II of (S)-2-(1-(9H-purin-6-ylamino)propyl)-5-fluoro-3-phenylquinazolin-4(3H)-one.

Provided is also a pharmaceutical composition including the composition of a mixture of polymorphic Form I and polymorphic Form II and one or more pharmaceutical acceptable carriers or excipients. In one embodiment, the pharmaceutical composition is for oral administration. For example, the pharmaceutical composition may be in the form a tablet.

In some of the foregoing embodiments, the polymorph (e.g. polymorphic Form I, polymorphic Form II, or both) is not hygroscopic. In some of the foregoing embodiments, the polymorph (e.g. polymorphic Form I, polymorphic Form II, or both) is anhydrous or non-crystalline.

Provided is a polymorph of (S)-2-(1-(9H-purin-6-ylamino)propyl)-5-fluoro-3-phenylquinazolin-4(3H)-one, wherein the polymorph is Form III having an X-ray powder diffraction pattern substantially as shown in FIG. 10A.

Provided is a polymorph of (S)-2-(1-(9H-purin-6-ylamino)propyl)-5-fluoro-3-phenylquinazolin-4(3H)-one, wherein the polymorph is Form IV having an X-ray powder diffraction pattern substantially as shown in FIG. 11.

Provided is a polymorph of (S)-2-(1-(9H-purin-6-ylamino)propyl)-5-fluoro-3-phenylquinazolin-4(3H)-one, wherein the polymorph is Form V having an X-ray powder diffraction pattern substantially as shown in FIG. 12.

Provided is a polymorph of (S)-2-(1-(9H-purin-6-ylamino)propyl)-5-fluoro-3-phenylquinazolin-4(3H)-one, wherein the polymorph is Form VI having an X-ray powder diffraction pattern substantially as shown in FIG. 13.

Provided is a polymorph of (S)-2-(1-(9H-purin-6-ylamino)propyl)-5-fluoro-3-phenylquinazolin-4(3H)-one, wherein the polymorph is Form VII having an X-ray powder diffraction pattern substantially as shown in FIG. 14A.

Provided is a polymorphic Form I of (S)-2-(1-(9H-purin-6-ylamino)propyl)-5-fluoro-3-phenylquinazolin-4(3H)-one having a unit cell, as determined by crystal X-ray crystallography, of the following dimensions: a=12.6971(7) Å; b=11.3577(8) Å; c=15.2065 (10) Å; α=90.00°; β=104.112°; and γ=90.00°.

Provided is a polymorphic Form II of (S)-2-(1-(9H-purin-6-ylamino)propyl)-5-fluoro-3-phenylquinazolin-4(3H)-one having a unit cell, as determined by crystal X-ray crystallography, of the following dimensions: a=9.1183(3) Å; b=11.3299(3) Å; c=20.7936(5) Å; α=90.00°; β=98.498°; and γ=90.00°.

Provided is a polymorphic Form III of (S)-2-(1-(9H-purin-6-ylamino)propyl)-5-fluoro-3-phenylquinazolin-4(3H)-one having a unit cell, as determined by crystal X-ray crystallography, of the following dimensions: a=8.6133(4) Å; b=11.0763(5) Å; c=14.3996(7) Å; α=99.457°; β=93.897°; and γ=107.275°.

Provided is a polymorphic Form IV of (S)-2-(1-(9H-purin-6-ylamino)propyl)-5-fluoro-3-phenylquinazolin-4(3H)-one having a unit cell, as determined by crystal X-ray crystallography, of the following dimensions: a=7.9394(5) Å; b=16.9606(11) Å; c=17.4405(13) Å; α=90.00°; β=90.00°; and γ=90.00°.

Provided is a polymorphic Form V of (S)-2-(1-(9H-purin-6-ylamino)propyl)-5-fluoro-3-phenylquinazolin-4(3H)-one having a unit cell, as determined by crystal X-ray crystallography, of the following dimensions: a=9.2354(3) Å; b=9.7692 (4) Å; c=35.4252 (12) Å; α=90.00°; β=90.00°; and γ=90.00°.

DETAILED DESCRIPTION

Figure 1A:
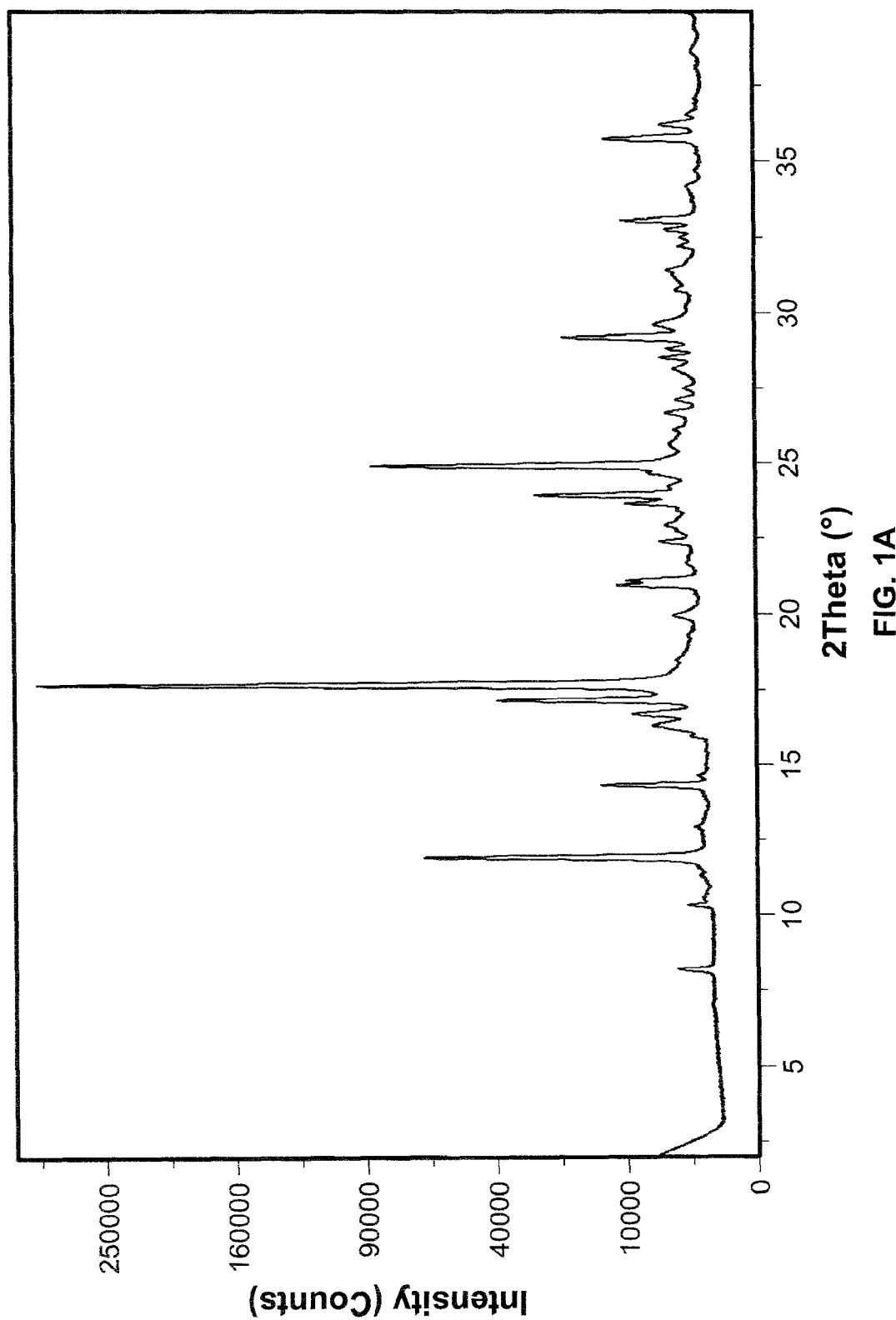
FIG. 1A shows an X-ray powder diffraction pattern (XRPD) pattern of polymorph Form I of (S)-2-(1-(9H-purin-6-ylamino)propyl)-5-fluoro-3-phenylquinazolin-4(3H)-one.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but are to be accorded the scope consistent with the claims.

Terms used in the singular will also include the plural and vice versa.

The use of the term "about" includes and describes the value or parameter per se. For example, "about x" includes and describes "x" per se. In some embodiments, the term "about" when used in association with a measurement, or used to modify a value, a unit, a constant, or a range of values, refers to variations of +/−5%.

Polymorphs of (S)-2-(1-(9H-purin-6-ylamino)propyl)-5-fluoro-3-phenylquinazolin-4(3H)-one and Compositions Thereof In some embodiments, the therapeutic use and commercialization of (S)-2-(1-(9H-purin-6-ylamino)propyl)-5-fluoro-3-phenylquinazolin-4(3H)-one involves the development of a crystalline form of (S)-2-(1-(9H-purin-6-ylamino)propyl)-5-fluoro-3-phenylquinazolin-4(3H)-one that is bioavailable and stable. Development dosage forms, including suitable oral unit dosage forms (such as tablets and capsules), is vital for commercialization of (S)-2-(1-(9H-purin-6-ylamino)propyl)-5-fluoro-3-phenylquinazolin-4(3H)-one dosage forms. As one of skill in the art would appreciate, variations in the crystal structure of a pharmaceutical drug substance may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product, particularly when formulated in a solid oral dosage form.

During the formulation process and the development of a commercial scale manufacturing process for (S)-2-(1-(9H-purin-6-ylamino)propyl)-5-fluoro-3-phenylquinazolin-4(3H)-one, two distinct crystalline forms, termed polymorph Form I and polymorph Form II, were observed. In particular, it was unpredictably observed that Form I partially converts to Form II upon compression, such as in the tableting process.

Specific processes were developed to consistently produce polymorphic Form I and Form II, and allowed the characterization of these polymorphic forms. The processes for the preparation of the polymorphs described herein, and characterization of these polymorphs are described in greater detail below.

Accordingly, in one aspect, the application discloses particular polymorphic forms of (S)-2-(1-(9H-purin-6-ylamino)propyl)-5-fluoro-3-phenylquinazolin-4(3H)-one, a compound having the molecular structure shown below:

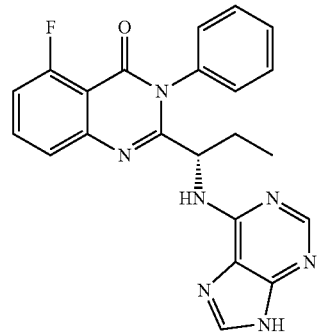

The compound name provided above is named using ChemBioDraw Ultra 12.0 and one skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including but not limited to Chemical Abstract Service (CAS) and International Union of Pure and Applied Chemistry (IUPAC). Accordingly, the compound structure provided above may also be named or identified as 5-fluoro-3-phenyl-2-[(1S)-1-(9H-purin-6-ylamino)propyl]quinazolin-4(3H)-one under IUPAC and 5-fluoro-3-phenyl-2-[(1S)-1-(9H-purin-6-ylamino)propyl]-4(3H)-quinazolinone under CAS.

Figure 1B:
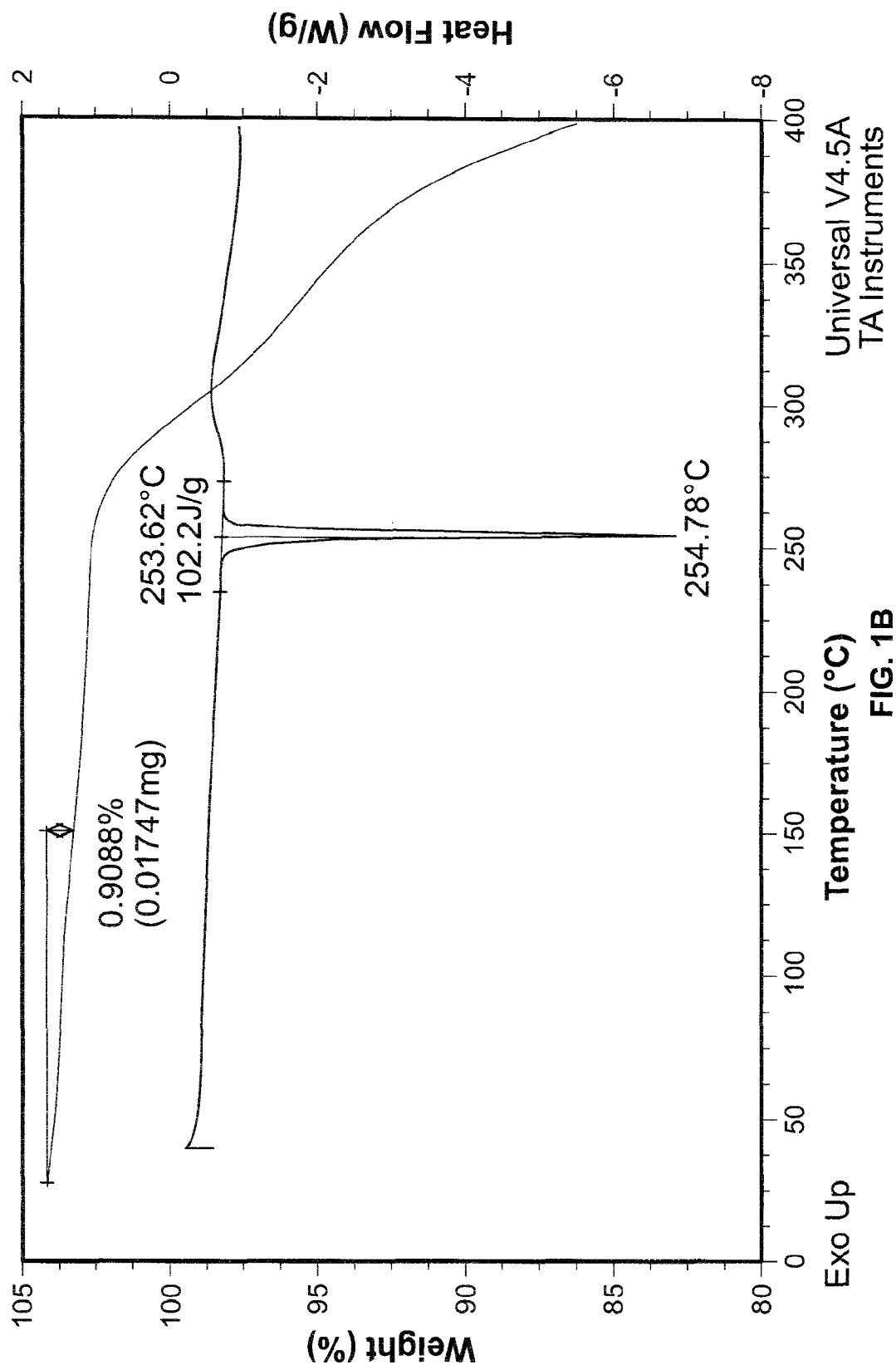
FIG. 1B shows a differential scanning calorimetry (DSC) and thermographic analysis (TGA) graph of polymorph Form I of (S)-2-(1-(9H-purin-6-ylamino)propyl)-5-fluoro-3-phenylquinazolin-4(3H)-one.

In one aspect is provided polymorphic Form I of (S)-2-(1-(9H-purin-6-ylamino)propyl)-5-fluoro-3-phenylquinazolin-4(3H)-one, wherein the polymorph exhibits an X-ray powder diffraction pattern substantially as shown in FIG. 1A. In other embodiments, polymorphic Form I exhibits a differential scanning calorimetry pattern substantially as shown in FIG. 1B.

In some embodiments, the term "substantially as shown in" when referring to an X-ray powder diffraction pattern or a differential scanning calorimetry pattern means that a pattern that is not necessarily identical to those depicted herein, but that falls within the limits of experimental error or deviations, when considered by one of ordinary skill in the art.

In other embodiments, polymorphic Form I is characterized as having a melting temperature onset as determined by differential scanning calorimetry at about 254° C. In yet other embodiments, polymorphic Form I is characterized as an anhydrous, crystalline solid. In yet other embodiments, polymorph Form I is substantially free of water, substantially free of solvent, or a combination thereof.

In some embodiments of polymorphic Form I, at least one, at least two, at least three, at least four, or all of the following (a)-(f) apply: (a) polymorphic Form I is anhydrous; (b) polymorphic Form I is crystalline; (c) polymorphic Form I has an X-ray powder diffraction pattern substantially as shown in FIG. 1A; (d) polymorphic Form I has a differential scanning calorimetry thermogram substantially as shown in FIG. 1B; (e) a melting temperature onset as determined by differential scanning calorimetry at about 254° C.; and (f) polymorph Form I absorbs less than 1 wt % moisture at 90% relative humidity at 25° C.

In some embodiments, polymorphic Form I comprises at least one, at least two, or all of the following properties:

(a) having an X-ray powder diffraction pattern substantially as shown in FIG. 1A;

(b) having a differential scanning calorimetry thermogram substantially as shown in FIG. 1B; and (c) a melting temperature onset as determined by differential scanning calorimetry at about 254° C.

In some embodiments, the polymorphic Form I has an X-ray powder diffraction pattern displaying at least two of the largest peaks as the X-ray powder diffraction pattern substantially as shown in FIG. 1A. In some embodiments, the polymorphic Form I has an X-ray powder diffraction pattern displaying at least three of the largest peaks as the X-ray powder diffraction pattern substantially as shown in FIG. 1A. In some embodiments, the polymorphic Form I has an X-ray powder diffraction pattern displaying at least four of the largest peaks as the X-ray powder diffraction pattern substantially as shown in FIG. 1A. In some embodiments, the polymorphic Form I has an X-ray powder diffraction pattern displaying at least five of the largest peaks as the X-ray powder diffraction pattern substantially as shown in FIG. 1A. In some embodiments, the polymorphic Form I has an X-ray powder diffraction pattern displaying at least six of the largest peaks as the X-ray powder diffraction pattern substantially as shown in FIG. 1A.

In certain embodiments, the polymorphic Form I has an X-ray powder diffraction pattern having characteristic peaks at diffraction angles expressed in degrees 2θ of about 14.3, about 17.2, about 17.7, about 20.9, about 23.9 and about 24.9. In one embodiment, the polymorphic Form I has an X-ray powder diffraction pattern having a characteristic peak at a diffraction angle expressed in degrees 2θ of about 17.7 degrees 2θ. In another embodiment, the polymorphic Form I has an X-ray powder diffraction pattern having a characteristic peak at a diffraction angle expressed in degrees 2θ of about 17.7 and about 24.9. In yet another embodiment, the polymorphic Form I has an X-ray powder diffraction pattern having characteristic peaks at diffraction angles expressed in degrees 2θ of 14.3, 17.2, 17.7, 20.9, 23.9 and 24.9. It should be understood that relative intensities can vary depending on a number of factors, including sample preparation, mounting, and the instrument and analytical procedure and settings used to obtain the spectrum. As such, the peak assignments listed herein are intended to encompass variations of plus or minus 0.2 degrees 2θ.

Figure 2A:
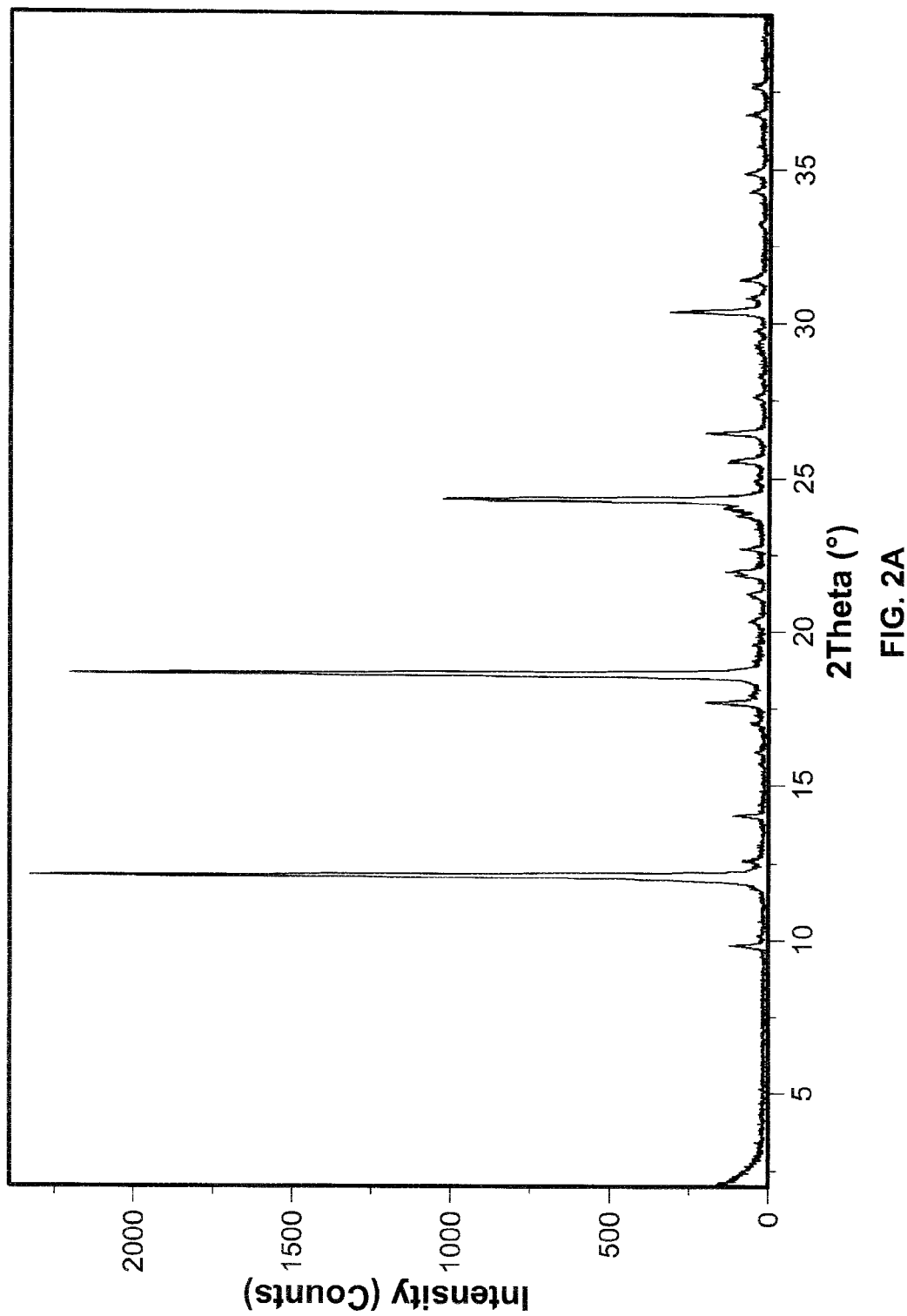
FIG. 2A shows an XRPD pattern of polymorph Form II of (S)-2-(1-(9H-purin-6-ylamino)propyl)-5-fluoro-3-phenylquinazolin-4(3H)-one.
Figure 2B:
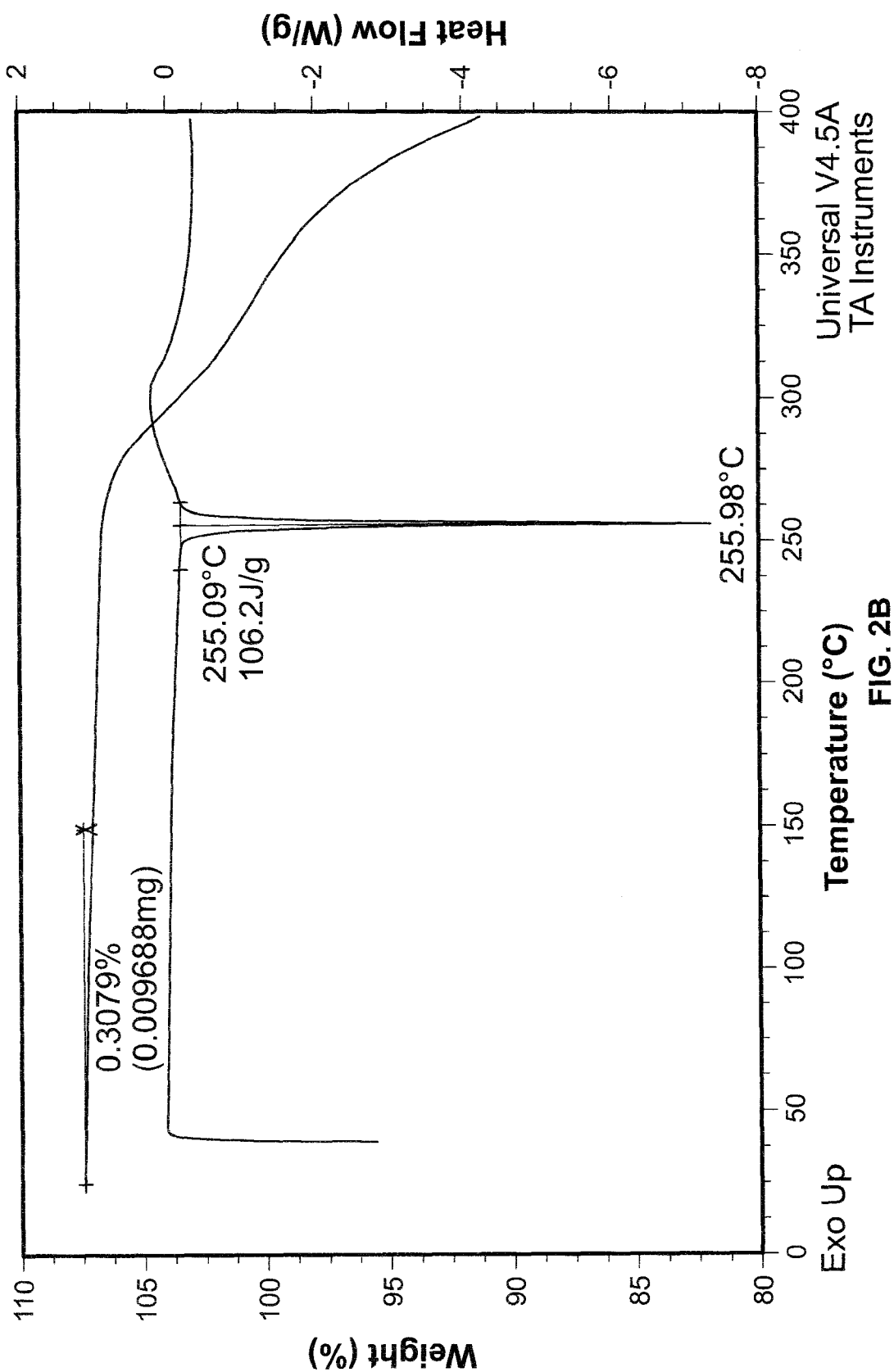
FIG. 2B shows a DSC and TGA graph of polymorph Form II of (S)-2-(1-(9H-purin-6-ylamino)propyl)-5-fluoro-3-phenylquinazolin-4(3H)-one.

In another aspect is provided polymorphic Form II of (S)-2-(1-(9H-purin-6-ylamino)propyl)-5-fluoro-3-phenylquinazolin-4(3H)-one, wherein the polymorph exhibits an X-ray powder diffraction pattern substantially as shown in FIG. 2A. In other embodiments, polymorphic Form II exhibits a differential scanning calorimetry pattern substantially as shown in FIG. 2B. In yet other embodiments, polymorphic Form II is characterized as an anhydrous, crystalline solid. In yet other embodiments, polymorph Form II is substantially free of water, substantially free of solvent, or a combination thereof.

In some embodiments of polymorphic Form II, at least one, at least two, at least three, or all of the following (a)-(e) apply: (a) polymorphic Form II is anhydrous; (b) polymorphic Form II is crystalline; (c) polymorphic Form II has an X-ray powder diffraction pattern substantially as shown in FIG. 2A; (d) polymorphic Form II has a differential scanning calorimetry thermogram substantially as shown in FIG. 2B; and (e) polymorphic Form II absorbs less than 1 wt % moisture at 90% relative humidity at 25° C.

In some embodiments, polymorphic Form II comprises at least one or both of the following properties:

(a) having an X-ray powder diffraction pattern substantially as shown in FIG. 2A; and (b) having a differential scanning calorimetry thermogram substantially as shown in FIG. 2B.

In some embodiments, polymorphic Form II has a melting temperature that may be different from the melting temperature of polymorphic Form I.

In some embodiments, the polymorphic Form II has an X-ray powder diffraction pattern displaying at least two of the largest peaks as the X-ray powder diffraction pattern substantially as shown in FIG. 2A. In some embodiments, the polymorphic Form II has an X-ray powder diffraction pattern displaying at least three of the largest peaks as the X-ray powder diffraction pattern substantially as shown in FIG. 2A. In some embodiments, the polymorphic Form II has an X-ray powder diffraction pattern displaying at least four of the largest peaks as the X-ray powder diffraction pattern substantially as shown in FIG. 2A.

In certain embodiments, the polymorphic Form II has an X-ray powder diffraction pattern having one or more characteristic peaks at diffraction angles expressed in degrees 2θ of about 14.0, about 18.6 and about 24.3. In one embodiment of polymorphic Form II, the X-ray powder diffraction pattern has a characteristic peak at about 18.6 degrees 2θ. In another embodiment of polymorphic Form II, the pattern has characteristic peaks at about 18.6 degrees 2θ and 14.0 degrees 2θ. In yet another embodiment of polymorphic Form II, the pattern has characteristic peaks at about 18.6 degrees 2θ and 24.3 degrees 2θ. In yet another embodiment of polymorphic Form II, the pattern has characteristic peaks at about 14.0 degrees 2θ and 24.3 degrees 2θ. In one embodiment, the polymorphic Form II has an X-ray powder diffraction pattern having one or more characteristic peaks at diffraction angles expressed in degrees 2θ of 14.0, 18.6 and 24.3.

In another aspect, provided are compositions comprising the polymorphs (e.g., polymorphic Form I, polymorphic Form II, or both) as described herein. In some embodiments, the composition comprises polymorphic Form I, polymorphic Form II, or a combination thereof. In some embodiments, the composition incorporates polymorphic Form I. In other embodiments, the composition incorporates polymorphic Form II.

In some embodiments are provided compositions incorporating the polymorphic Form I as described herein, wherein the (S)-2-(1-(9H-purin-6-ylamino)propyl)-5-fluoro-3-phenylquinazolin-4(3H)-one within the composition is a substantially pure polymorphic Form I. In particular embodiments of compositions incorporating the polymorphic Form I, at least about 95%, at least about 96%, at least about 97%, at least about 98%, or at least about 99% of the (S)-2-(1-(9H-purin-6-ylamino)propyl)-5-fluoro-3-phenylquinazolin-4(3H)-one present in the composition is polymorphic Form I.

In other embodiments of compositions incorporating the polymorphic Form I, the composition is substantially free of polymorphic Form II. In certain embodiments of compositions incorporating the polymorphic Form I, less than about 5%, less than about 4%, less than about 3%, less than about 2% or less than about 1% of the (S)-2-(1-(9H-purin-6-ylamino)propyl)-5-fluoro-3-phenylquinazolin-4(3H)-one present in the composition is polymorphic Form II.

In some embodiments of the compositions comprising polymorphic Form I, the composition is substantially free of amorphous or non-crystalline (S)-2-(1-(9H-purin-6-ylamino)propyl)-5-fluoro-3-phenylquinazolin-4(3H)-one. For example, in certain embodiments, the composition comprising the polymorphic Form I has less than about 5%, less than about 4%, less than about 3%, less than about 2%, or less than about 1% by weight of amorphous or non-crystalline (S)-2-(1-(9H-purin-6-ylamino)propyl)-5-fluoro-3-phenylquinazolin-4(3H)-one.

In other embodiments of the compositions comprising polymorphic Form I, the composition is substantially free of salts of (S)-2-(1-(9H-purin-6-ylamino)propyl)-5-fluoro-3-phenylquinazolin-4(3H)-one. In one embodiment of the compositions comprising polymorphic Form I, the composition is substantially free of an HCl salt of (S)-2-(1-(9H-purin-6-ylamino)propyl)-5-fluoro-3-phenylquinazolin-4(3H)-one. For example, in certain embodiments, the composition comprising the polymorphic Form I has less than about 5%, less than about 4%, less than about 3%, less than about 2%, or less than about 1% by weight of a salt of (S)-2-(1-(9H-purin-6-ylamino)propyl)-5-fluoro-3-phenylquinazolin-4(3H)-one. In one embodiment, the composition comprising the polymorphic Form I has less than about 5%, less than about 4%, less than about 3%, less than about 2%, or less than about 1% by weight of an HCl salt of (S)-2-(1-(9H-purin-6-ylamino)propyl)-5-fluoro-3-phenylquinazolin-4(3H)-one.

In some embodiments, the term "substantially pure" or "substantially free" with respect to a particular polymorphic form of a compound means that the polymorphic form contains about less than 30%, about less than 20%, about less than 15%, about less than 10%, about less than 5%, or about less than 1% by weight of impurities. In other embodiments, "substantially pure" or "substantially free of" refers to a substance free of impurities. Impurities may, for example, include by-products or left over reagents from chemical reactions, contaminants, degradation products, other polymorphic forms, water, and solvents.

In some embodiments of compositions incorporating the polymorphic Form I, the composition is substantially free of polymorphs other than polymorphic Form I. In other embodiments, less than about 5%, less than about 4%, less than about 3%, less than about 2% or less than about 1% of the (S)-2-(1-(9H-purin-6-ylamino)propyl)-5-fluoro-3-phenylquinazolin-4(3H)-one present in the composition are polymorphs other than polymorphic Form I. In yet other embodiments of compositions incorporating the polymorphic Form I, impurities make up less than about 5%, less than about 4%, less than about 3%, less than about 2% or less than about 1% of the total mass relative to the mass of the polymorphic Form I present. Impurities may, for example, include by-products from synthesizing (S)-2-(1-(9H-purin-6-ylamino)propyl)-5-fluoro-3-phenylquinazolin-4(3H)-one, contaminants, degradation products, other polymorphic forms, water, and solvents.

In some embodiments are provided compositions incorporating the polymorphic Form II as described herein, wherein (S)-2-(1-(9H-purin-6-ylamino)propyl)-5-fluoro-3-phenylquinazolin-4(3H)-one within the composition is a substantially pure polymorphic Form II. In certain embodiments of compositions incorporating the polymorphic Form II, at least about 95%, at least about 96%, at least about 97%, at least about 98%, or at least about 99% of the (S)-2-(1-(9H-purin-6-ylamino)propyl)-5-fluoro-3-phenylquinazolin-4(3H)-one present in the composition is polymorphic Form II.

In other embodiments of compositions incorporating the polymorphic Form II, the composition is substantially free of polymorphic Form I. In certain embodiments of compositions incorporating the polymorphic Form II, less than about 5%, less than about 4%, less than about 3%, less than about 2% or less than about 1% of the (S)-2-(1-(9H-purin-6-ylamino)propyl)-5-fluoro-3-phenylquinazolin-4(3H)-one present in the composition is polymorphic Form I.

In some embodiments of compositions incorporating the polymorphic Form II, the composition is substantially free of polymorphs other than polymorphic Form II. In other embodiments, less than about 5%, less than about 4%, less than about 3%, less than about 2% or less than about 1% of the (S)-2-(1-(9H-purin-6-ylamino)propyl)-5-fluoro-3-phenylquinazolin-4(3H)-one present in the composition are polymorphs other than polymorphic Form II.

In some embodiments of the compositions comprising polymorphic Form II, the composition is substantially free of amorphous or non-crystalline (S)-2-(1-(9H-purin-6-ylamino)propyl)-5-fluoro-3-phenylquinazolin-4(3H)-one. For example, in certain embodiments, the composition comprising the polymorphic Form II has less than about 5%, less than about 4%, less than about 3%, less than about 2%, or less than about 1% by weight of amorphous or non-crystalline (S)-2-(1-(9H-purin-6-ylamino)propyl)-5-fluoro-3-phenylquinazolin-4(3H)-one.

In other embodiments of the compositions comprising polymorphic Form II, the composition is substantially free of salts of (S)-2-(1-(9H-purin-6-ylamino)propyl)-5-fluoro-3-phenylquinazolin-4(3H)-one. In one embodiment of the compositions comprising polymorphic Form II, the composition is substantially free of an HCl salt of (S)-2-(1-(9H-purin-6-ylamino)propyl)-5-fluoro-3-phenylquinazolin-4(3H)-one. For example, in certain embodiments, the composition comprising the polymorphic Form II has less than about 5%, less than about 4%, less than about 3%, less than about 2%, or less than about 1% by weight of a salt of (S)-2-(1-(9H-purin-6-ylamino)propyl)-5-fluoro-3-phenylquinazolin-4(3H)-one. In one embodiment, the composition comprising the polymorphic Form II has less than about 5%, less than about 4%, less than about 3%, less than about 2%, or less than about 1% by weight of an HCl salt of (S)-2-(1-(9H-purin-6-ylamino)propyl)-5-fluoro-3-phenylquinazolin-4(3H)-one.

In yet other embodiments of compositions incorporating the polymorphic Form II, impurities make up less than about 5%, less than about 4%, less than about 3%, less than about 2% or less than about 1% of the total mass relative to the mass of the polymorphic Form II present. Impurities may, for example, include by-products from synthesizing (S)-2-(1-(9H-purin-6-ylamino)propyl)-5-fluoro-3-phenylquinazolin-4(3H)-one, contaminants, degradation products, other polymorphic forms, water, and solvents.

In another aspect, provided are compositions comprising a mixture of two or more of the polymorphic forms described herein. In certain embodiments, provided is a composition comprising a mixture of polymorphic Form I and Form II as described herein. In some embodiments, the composition consists essentially of polymorphic Form I and 5%, 4%, 3%, 2%, 1%, or less than 1% of Form II. In other embodiments, the composition consists essentially of polymorphic Form II and 5%, 4%, 3%, 2%, 1%, or less than 1% of Form I.

In some embodiments of the compositions comprising a mixture of polymorphic Form I and polymorphic Form II, the composition is substantially free of amorphous or non-crystalline (S)-2-(1-(9H-purin-6-ylamino)propyl)-5-fluoro-3-phenylquinazolin-4(3H)-one. For example, in certain embodiments, the composition comprising a mixture of polymorphic Form I and polymorphic Form II has less than about 5%, less than about 4%, less than about 3%, less than about 2%, or less than about 1% by weight of amorphous or non-crystalline (S)-2-(1-(9H-purin-6-ylamino)propyl)-5-fluoro-3-phenylquinazolin-4(3H)-one.

In other embodiments of the compositions comprising a mixture of polymorphic Form I and polymorphic Form II, the composition is substantially free of salts of (S)-2-(1-(9H-purin-6-ylamino)propyl)-5-fluoro-3-phenylquinazolin-4(3H)-one. In one embodiment of the compositions comprising a mixture of polymorphic Form I and polymorphic Form II, the composition is substantially free of an HCl salt of (S)-2-(1-(9H-purin-6-ylamino)propyl)-5-fluoro-3-phenylquinazolin-4(3H)-one. For example, in certain embodiments, the composition comprising a mixture of polymorphic Form I and polymorphic Form II has less than about 5%, less than about 4%, less than about 3%, less than about 2%, or less than about 1% by weight of a salt of (S)-2-(1-(9H-purin-6-ylamino)propyl)-5-fluoro-3-phenylquinazolin-4(3H)-one. In one embodiment, the composition comprising a mixture of polymorphic Form I and polymorphic Form II has less than about 5%, less than about 4%, less than about 3%, less than about 2%, or less than about 1% by weight of an HCl salt of (S)-2-(1-(9H-purin-6-ylamino)propyl)-5-fluoro-3-phenylquinazolin-4(3H)-one.

In another embodiment of the composition comprising a mixture of polymorphic Form I and polymorphic Form II, the polymorphic Form I in the composition is present in excess of polymorphic Form II. For example, in one embodiment of the composition comprising a mixture of polymorphic Form I and polymorphic Form II, the weight ratio of polymorphic Form I to polymorphic Form II in the composition is between 99 to 1 and 55 to 45, or about 60 to 40, about 70 to 30, about 75 to 25, about 80 to 20, about 85 to 15, about 90 to 10, about 95 to 5, or about 99 to 1. In one embodiment, the weight ratio of polymorphic Form I to polymorphic Form II is between 90:1 and 99:1. In yet another embodiment, the polymorphic Form II in the composition is present in excess of polymorphic Form I. For example, the weight ratio of polymorphic Form II to polymorphic Form I in the composition is between 99 to 1 and 55 to 45, or about 60 to 40, about 70 to 30, about 75 to 25, about 80 to 20, about 85 to 15, about 90 to 10, about 95 to 5, or about 99 to 1. In yet another embodiment, polymorphic Form I and polymorphic Form II are present in approximately the same amounts in the composition.

Figure 10A:
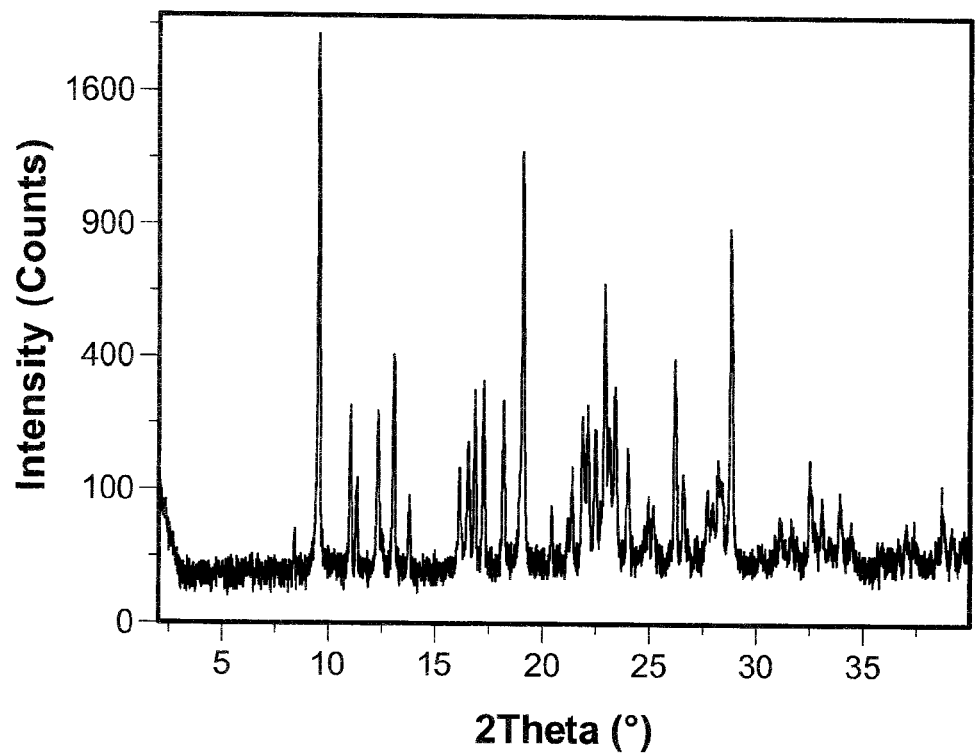
FIGS. 10A and 10B show an XRPD pattern and a TGA graph, respectively, of polymorph Form III of (S)-2-(1-(9H-purin-6-ylamino)propyl)-5-fluoro-3-phenylquinazolin-4(3H)-one.
Figure 10B:
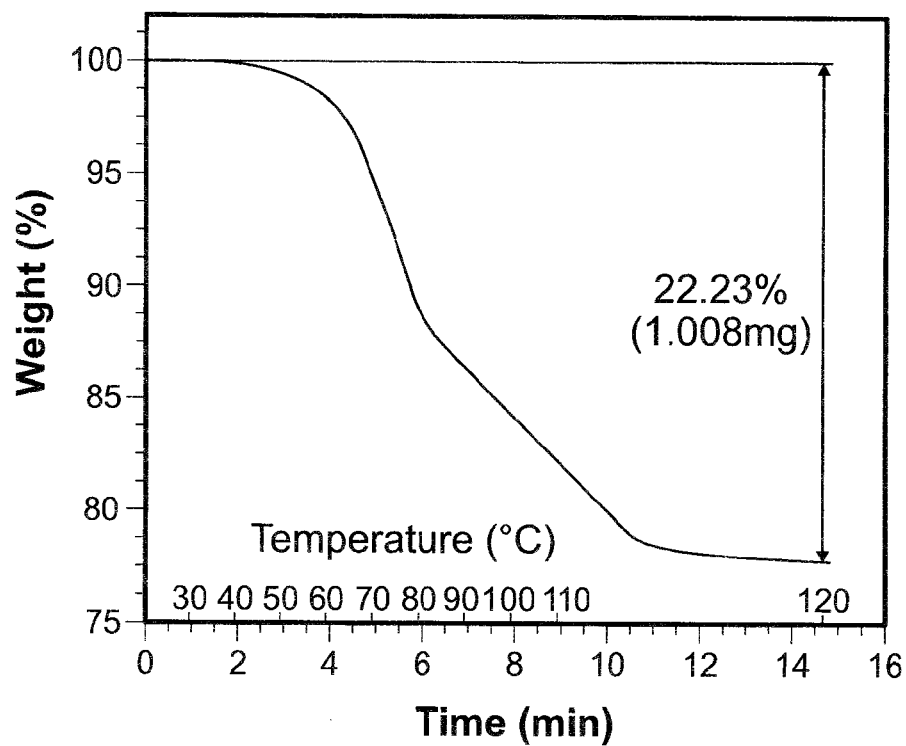
Figure 11:
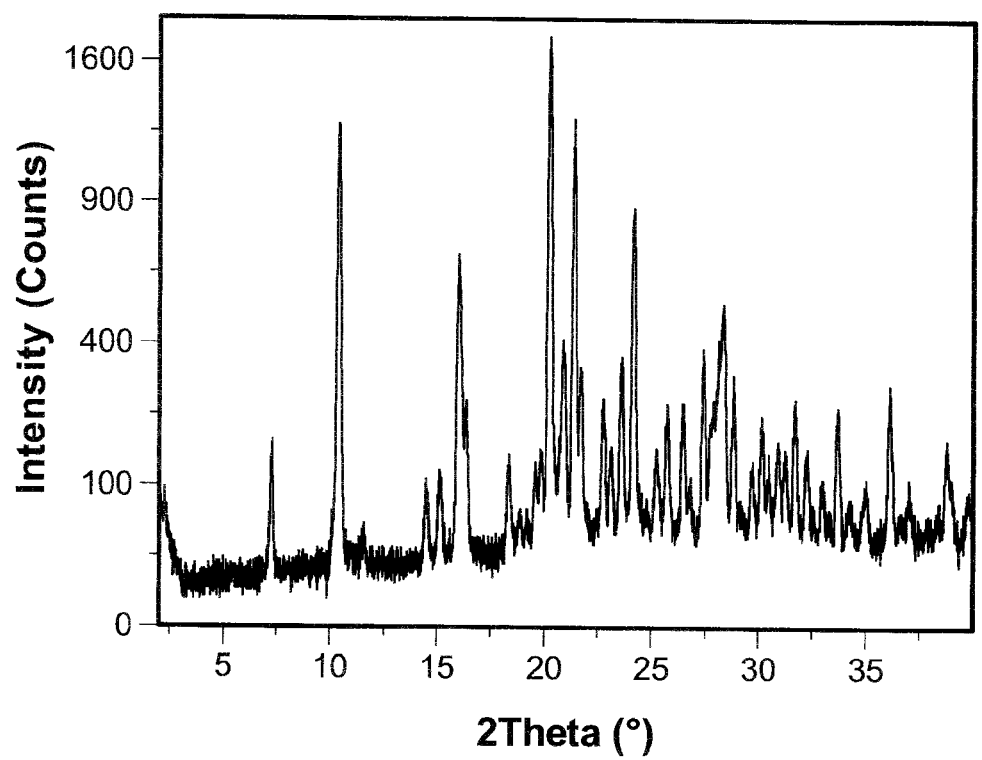
FIG. 11 shows an XRPD pattern of polymorph Form IV of (S)-2-(1-(9H-purin-6-ylamino)propyl)-5-fluoro-3-phenylquinazolin-4(3H)-one.
Figure 12:
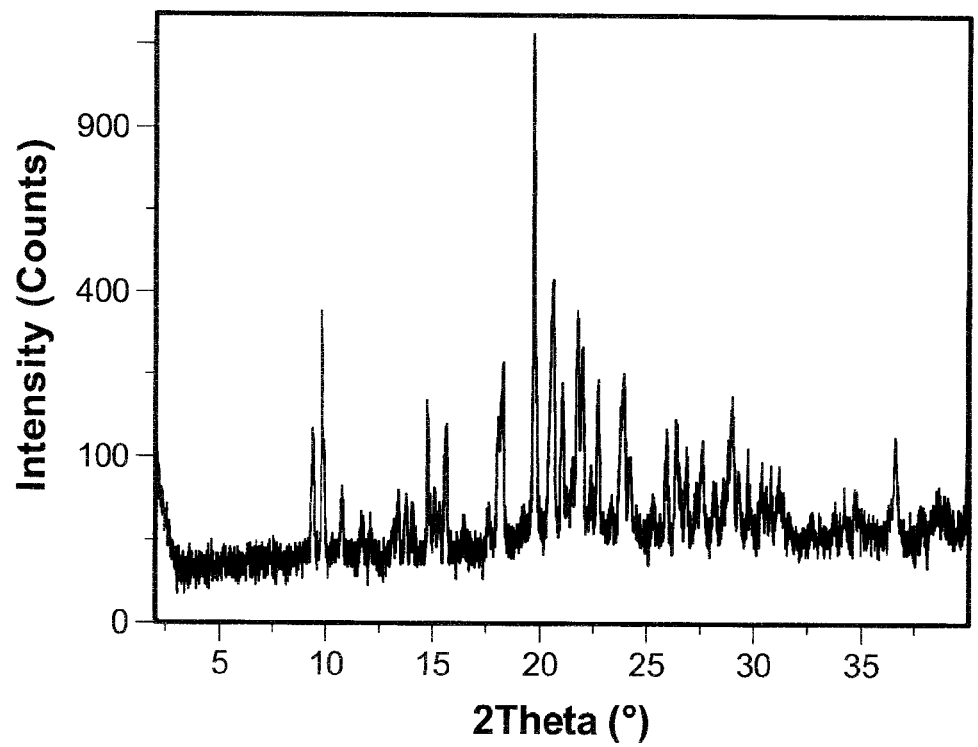
FIG. 12 shows an XRPD pattern of polymorph Form V of (S)-2-(1-(9H-purin-6-ylamino)propyl)-5-fluoro-3-phenylquinazolin-4(3H)-one.
Figure 13:
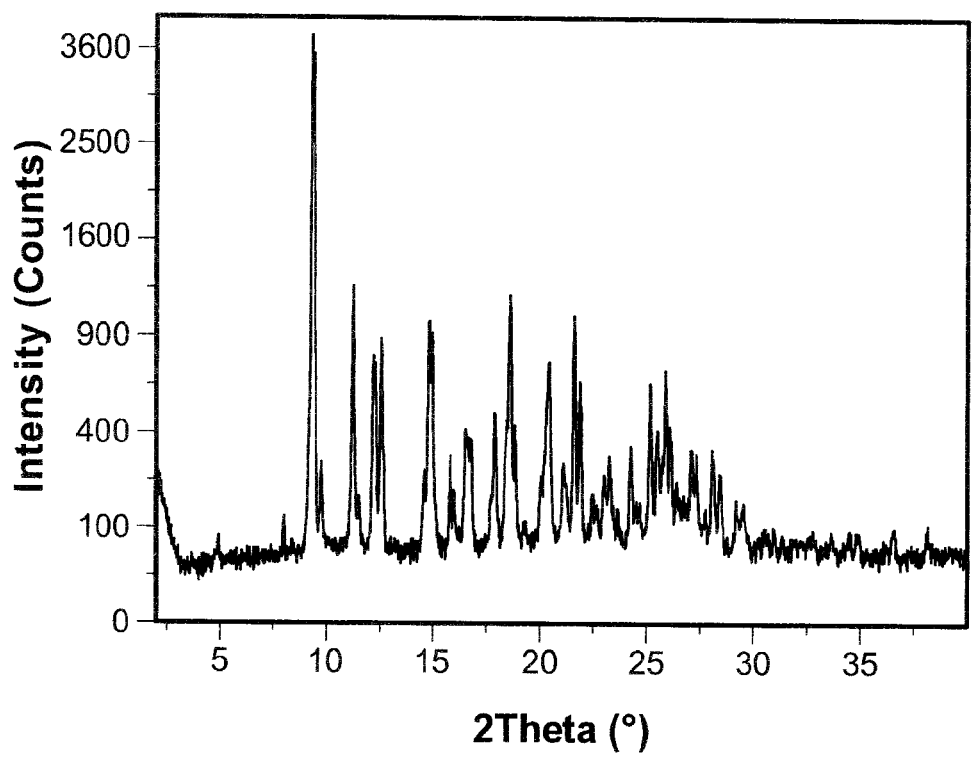
FIG. 13 shows an XRPD pattern of polymorph Form VI of (S)-2-(1-(9H-purin-6-ylamino)propyl)-5-fluoro-3-phenylquinazolin-4(3H)-one.
Figure 14A:
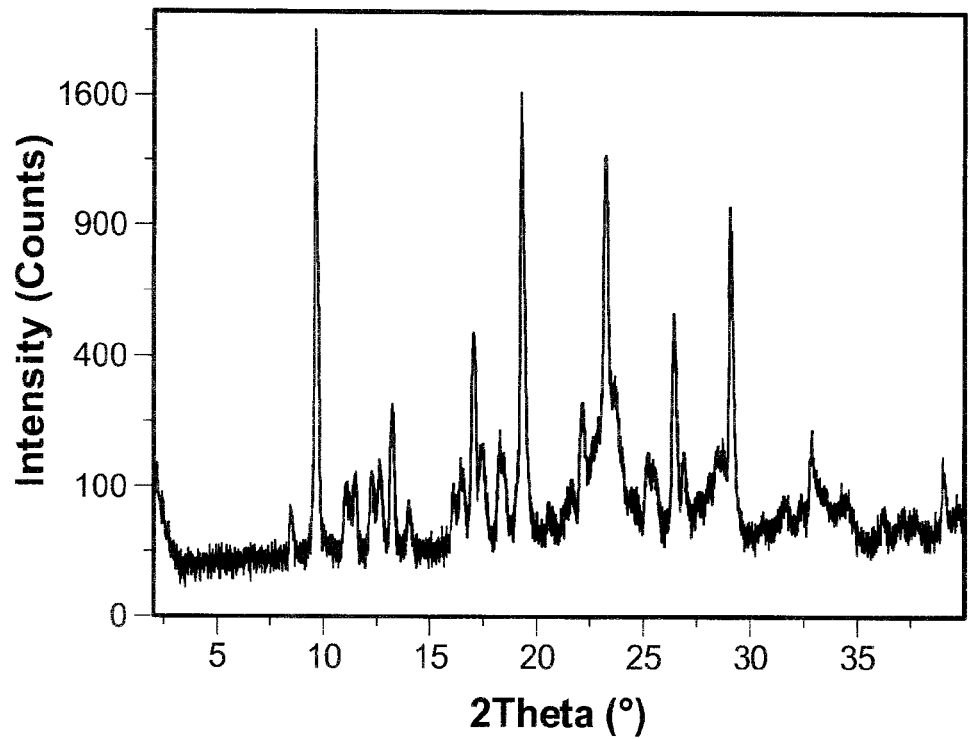
FIGS. 14A and 14B show an XRPD pattern and a TGA graph, respectively, of polymorph Form VII of (S)-2-(1-(9H-purin-6-ylamino)propyl)-5-fluoro-3-phenylquinazolin-4(3H)-one.
Figure 14B:
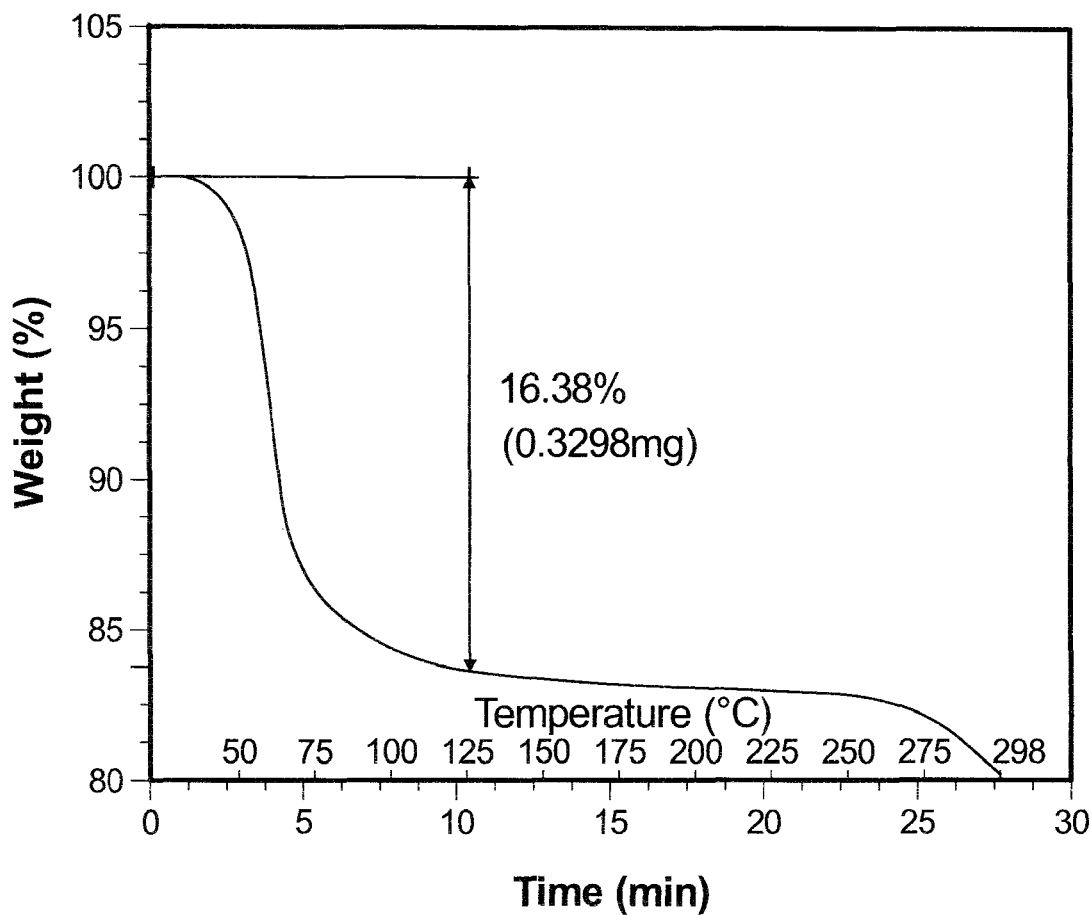

In another embodiment, provided is a polymorph of (S)-2-(1-(9H-purin-6-ylamino)propyl)-5-fluoro-3-phenylquinazolin-4(3H)-one, wherein the polymorph is Form III having an X-ray powder diffraction pattern substantially as shown in FIG. 10. In yet another embodiment, provided is a polymorph of (S)-2-(1-(9H-purin-6-ylamino)propyl)-5-fluoro-3-phenylquinazolin-4(3H)-one, wherein the polymorph is Form IV having an X-ray powder diffraction pattern substantially as shown in FIG. 11. In yet another embodiment, provided is a polymorph of (S)-2-(1-(9H-purin-6-ylamino)propyl)-5-fluoro-3-phenylquinazolin-4(3H)-one, wherein the polymorph is Form V having an X-ray powder diffraction pattern substantially as shown in FIG. 12. In yet another embodiment, provided is a polymorph of (S)-2-(1-(9H-purin-6-ylamino)propyl)-5-fluoro-3-phenylquinazolin-4(3H)-one, wherein the polymorph is Form VI having an X-ray powder diffraction pattern substantially as shown in FIG. 13. In yet another embodiment, provided is a polymorph of (S)-2-(1-(9H-purin-6-ylamino)propyl)-5-fluoro-3-phenylquinazolin-4(3H)-one, wherein the polymorph is Form VII having an X-ray powder diffraction pattern substantially as shown in FIG. 14. Provided are also compositions that include any of polymorphic Form III, IV, V, VI or VII as described herein.

Preparation of the Polymorphs

One method of synthesizing (S)-2-(1-(9H-purin-6-ylamino)propyl)-5-fluoro-3-phenylquinazolin-4(3H)-one has been previously described in U.S. Pat. No. 7,932,260. This reference is hereby incorporated herein by reference in its entirety, and specifically with respect to the synthesis of (S)-2-(1-(9H-purin-6-ylamino)propyl)-5-fluoro-3-phenylquinazolin-4(3H)-one. The methods for preparing the polymorphs (including polymorphic Form I and Form II) may yield quantity and quality differences compared to the methods for preparing (S)-2-(1-(9H-purin-6-ylamino)propyl)-5-fluoro-3-phenylquinazolin-4(3H)-one produced on laboratory scale.

Polymorphic forms of (S)-2-(1-(9H-purin-6-ylamino)propyl)-5-fluoro-3-phenylquinazolin-4(3H)-one have been discovered. The choice of a particular temperature may affect the formation favoring one polymorphic form of (S)-2-(1-(9H-purin-6-ylamino)propyl)-5-fluoro-3-phenylquinazolin-4(3H)-one over another. In one aspect, polymorphic Form I described herein may be prepared by dissolving crude (S)-2-(1-(9H-purin-6-ylamino)propyl)-5-fluoro-3-phenylquinazolin-4(3H)-one in a solvent or solvent combination (e.g., by heating under reflux), followed by cooling the solution to a temperature of at least about 30° C. In certain embodiments, cooling the solution to a temperature between about 30° C. and about 40° C., or more specifically between about 30° C. and about 35° C. or between about 35° C. and about 40° C., may favor producing the polymorphic Form I over the polymorphic Form II. Suitable solvents may include, for example, water or an organic solvent (e.g., methanol, ethanol, propanol, isopropyl acetate, methyl t-butyl ether, dimethylsulfoxide, ethyl acetate, 2-methyl tetrahydrofuran, methyl ethyl ketone, and methyl isobutyl ketone, hexane, heptane), or a mixture thereof. In yet other embodiments, the method further includes isolating the solids, such as polymorphic Form I solids; washing the isolated solids; and drying the washed isolated solids to obtain substantially pure polymorphic Form I.

In other embodiments, polymorphic Form I may be obtained from a salt of (S)-2-(1-(9H-purin-6-ylamino)propyl)-5-fluoro-3-phenylquinazolin-4(3H)-one, such as, for example, a hydrochloride salt of (S)-2-(1-(9H-purin-6-ylamino)propyl)-5-fluoro-3-phenylquinazolin-4(3H)-one. In one embodiment, the hydrochloride salt of (S)-2-(1-(9H-purin-6-ylamino)propyl)-5-fluoro-3-phenylquinazolin-4(3H)-one may be combined with a solvent or solvent combination to form an acidic mixture or solution. The solvent or solvent combination may be, for example, water and/or an organic solvent. In one embodiment, the solvent includes water, ethanol, or a mixture thereof. The acidic mixture or solution is then neutralized to form free (S)-2-(1-(9H-purin-6-ylamino)propyl)-5-fluoro-3-phenylquinazolin-4(3H)-one, and heated to convert at least a portion of the free (S)-2-(1-(9H-purin-6-ylamino)propyl)-5-fluoro-3-phenylquinazolin-4(3H)-one to polymorphic Form I. In certain embodiments, polymorphic Form I crystals may be added to the neutralized mixture or solution before heating. The neutralized mixture or solution may be heated at a temperature of at least about 30° C., and more specifically between 40° C. and 60° C., or about 50° C.

In another aspect, polymorphic Form II described herein can be prepared by converting a polymorphic Form I of (S)-2-(1-(9H-purin-6-ylamino)propyl)-5-fluoro-3-phenylquinazolin-4(3H)-one to polymorphic Form II. Polymorphic Form I can be converted into polymorphic Form II by grinding or compression.

In some embodiments, the method to prepare polymorphic Form II includes grinding the polymorphic Form I to a micron particle size (e.g., between about 1 micron to about 10 microns); and stirring the ground polymorphic Form I in a solvent at a temperature of less than about 30° C. to form the polymorphic Form II. In certain embodiments, the ground polymorphic Form I is stirred at a temperature of between about 25° C. and about 30° C. to form the polymorphic Form II.

Certain solvents or solvent combinations used in the grinding method described above to prepare polymorphic Form II may favor the rate of formation of polymorphic Form II over the rate of formation of polymorphic Form I. For example, in certain embodiments, the use of acetone may increase rate of formation of polymorphic Form II over polymorphic Form I. In one variation of the methods to prepare polymorphic Form II, polymorphic Form I of (S)-2-(1-(9H-purin-6-ylamino)propyl)-5-fluoro-3-phenylquinazolin-4(3H)-one is suspended in an acetone at a temperature less than about 30° C., or between about 25° C. and about 30° C.

The grinding in the method described above to prepare polymorphic Form II may be performed using any suitable methods or techniques known to one of skill in the art, including for example, a mortar and pestle, a high shear wet mill, a high shear dry mixer, a jet mill, a ball mill, or a combination thereof. In certain embodiments, the grinding is performed using a ball mill. Furthermore, as discussed above, stirring the suspension of polymorphic Form I in the solvent or solvent combinations described above at a temperature of between about 25° C. and about 30° C. may unexpectedly favor the production of the polymorphic Form II over polymorphic Form I.

In other embodiments, polymorphic Form II described herein can be prepared by compressing polymorphic Form I at a pressure of between about 500 psi and about 5000 psi to convert at least a portion of polymorphic Form I to polymorphic Form II. In certain embodiments, the polymorphic Form I is compressed at a pressure of between 1000 psi and about 4500 psi. Any suitable methods known in the art may be used to compress polymorphic Form I, including for example a tablet press or a rotary press. It should be understood that the compression duration may vary depending on the type of press used. For example, in some embodiments where a tablet press is used, the polymorphic Form I may be compressed for about 30 seconds, about 1 minute, or up to about 5 minutes to produce polymorphic Form II. In other embodiments where a rotary press is used, the polymorphic Form I may be compressed in less than about 1 second, or between about 1 second to about 30 seconds to produce polymorphic Form II.

Compressing polymorphic Form I of (S)-2-(1-(9H-purin-6-ylamino)propyl)-5-fluoro-3-phenylquinazolin-4(3H)-one unexpectedly converts at least a portion of polymorphic Form I into polymorphic Form II.

The other polymorphic forms described herein that are solvates (e.g., Forms III, IV, V, VI and VII) can be prepared by converting polymorphic Form I into the other forms in the presence of one or more solvents. In some embodiments, polymorphic Form III can be prepared by mixing polymorphic Form I with water and isopropyl alcohol (IPA). In other embodiments, polymorphic Form IV can be prepared by mixing polymorphic Form I with dimethylformamide (DMF). In yet other embodiments, polymorphic Form V can be prepared by mixing polymorphic Form I with dimethylformamide (DMF). In yet other embodiments, polymorphic Form VI can be prepared by mixing polymorphic Form I with dichloromethane (DCM). In yet other embodiments, polymorphic Form V can be prepared by mixing polymorphic Form I with dimethylsulfoxide (DMSO). In yet other embodiments, polymorphic Form VII can be prepared by mixing polymorphic Form I with water and ethanol. In some of the foregoing embodiments to convert polymorphic Form I into one of polymorphic Forms III, IV, V, VI and VII, polymorphic Form I can be mixed with the one or more solvents at room temperature.

Pharmaceutical Compositions

The polymorphic forms described herein can be administered as the neat chemical, but it is typical, and preferable, to administer the compound in the form of a pharmaceutical composition or formulation. Accordingly, provided are pharmaceutical compositions that include the polymorphic forms described herein (e.g., Form I and/or Form II) and a biocompatible pharmaceutical carrier, excipient, adjuvant, or vehicle. The composition can include the polymorphic forms described herein either as the sole active agent or in combination with other agents, such as oligo- or polynucleotides, oligo- or polypeptides, drugs, or hormones mixed with one or more pharmaceutically acceptable carriers or excipients. Carriers, excipients, and other ingredients can be deemed pharmaceutically acceptable insofar as they are compatible with other ingredients of the formulation and not deleterious to the recipient thereof.

For example, in some embodiments, provided herein is a pharmaceutical composition comprising polymorphic Form I of (S)-2-(1-(9H-purin-6-ylamino)propyl)-5-fluoro-3-phenylquinazolin-4(3H)-one, and a pharmaceutical acceptable carrier or excipient. In other embodiments, provided herein is a pharmaceutical composition comprising polymorphic Form II of (S)-2-(1-(9H-purin-6-ylamino)propyl)-5-fluoro-3-phenylquinazolin-4(3H)-one, and a pharmaceutical acceptable carrier or excipient. In yet other embodiments, provided herein is a pharmaceutical composition comprising a mixture of polymorphic Form I and polymorphic Form II of (S)-2-(1-(9H-purin-6-ylamino)propyl)-5-fluoro-3-phenylquinazolin-4(3H)-one, and a pharmaceutical acceptable carrier or excipient.

In one embodiment of the pharmaceutical composition, the polymorphic Form I in the composition is present in excess of polymorphic Form II. For example, the weight ratio of polymorphic Form I to polymorphic Form II in the pharmaceutical composition may be between 99 to 1 and 55 to 45, or may be 60 to 40, 70 to 30, 75 to 25, 80 to 20, 85 to 15, 90 to 10, 95 to 5, or 99 to 1. In one embodiment, the weight ratio of polymorphic Form I to polymorphic Form II is between 90:1 and 99:1. In yet another embodiment, the polymorphic Form II in the pharmaceutical composition is present in excess of polymorphic Form I. For example, the weight ratio of polymorphic Form II to polymorphic Form I in the pharmaceutical composition may be between 99 to 1 and 55 to 45, or may be 60 to 40, 70 to 30, 75 to 25, 80 to 20, 85 to 15, 90 to 10, 95 to 5, or 99 to 1. In yet another embodiment, polymorphic Form I and polymorphic Form II are present in approximately the same amounts in the pharmaceutical composition.

Techniques for formulation and administration of pharmaceutical compositions can be found in *Remington's Pharmaceutical Sciences,* 18th Ed., Mack Publishing Co, Easton, Pa., 1990. The pharmaceutical compositions described herein can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The pharmaceutical compositions can be formulated to contain suitable pharmaceutically acceptable carriers, and optionally can comprise excipients and auxiliaries that facilitate processing of the polymorphic forms described herein into preparations that can be used pharmaceutically. The mode of administration generally determines the nature of the carrier. For example, formulations for parenteral administration can include aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art. For preparations including proteins, the formulation can include stabilizing materials, such as polyols (e.g., sucrose) and/or surfactants (e.g., nonionic surfactants), and the like.

Alternatively, formulations for parenteral use can include dispersions or suspensions of polymorphic forms described herein prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, dextran, and mixtures thereof. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT™ series available from Rohm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethlyene sorbitol and sorbitan esters, microcrystalline cellulose, aluminum metahydroxide, bentonite, agar-agar, gum tragacanth, and mixtures thereof.

Liposomes containing the polymorphic forms described herein also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See, e.g., Prescott (Ed.), Methods in Cell Biology, Vol. XIV, p. 33, Academic Press, New York (1976).

In some embodiments, the polymorph or composition thereof disclosed herein is formulated for oral administration using pharmaceutically acceptable carriers well known in the art. Preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or more excipients, which include, without limitation:

a) diluents, such as microcrystalline cellulose and sugars, including lactose, dextrose, sucrose, mannitol, or sorbitol;

b) binders, such as sodium starch glycolate, croscarmellose sodium, magnesium aluminum silicate, starch from corn, wheat, rice, potato, etc.;

c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;

d) disintegrating or solubilizing agents such as cross-linked polyvinyl pyrrolidone, starches, agar, alginic acid or a salt thereof, such as sodium alginate, or effervescent compositions;

e) lubricants, such as silica, talc, stearic acid or its magnesium or calcium salt, and polyethylene glycol;

f) flavorants and sweeteners;

g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

For example, provided is a tablet comprising one or more of the polymorphic forms described herein (e.g., Form I and/or Form II), and one or more pharmaceutically acceptable carriers or excipients. In one embodiment, the tablet comprises substantially pure polymorphic Form I of (S)-2-(1-(9H-purin-6-ylamino)propyl)-5-fluoro-3-phenylquinazolin-4(3H)-one, and one or more pharmaceutically acceptable carriers or excipients. In other embodiments, the tablet comprises substantially pure polymorphic Form II of (S)-2-(1-(9H-purin-6-ylamino)propyl)-5-fluoro-3-phenylquinazolin-4(3H)-one, and one or more pharmaceutically acceptable carriers or excipients. In yet other embodiments, the tablet comprises a mixture of polymorphic Form I and polymorphic Form II of (S)-2-(1-(9H-purin-6-ylamino)propyl)-5-fluoro-3-phenylquinazolin-4(3H)-one, and one or more pharmaceutically acceptable carriers or excipients.

In one embodiment of the tablet, the polymorphic Form I in the composition is present in excess of polymorphic Form II. For example, the weight ratio of polymorphic Form I to polymorphic Form II in the tablet is between 99 to 1 and 55 to 45, or may be 60 to 40, 70 to 30, 75 to 25, 80 to 20, 85 to 15, 90 to 10, 95 to 5, or 99 to 1. In one embodiment, the weight ratio of polymorphic Form I to polymorphic Form II is between 90:1 and 99:1. In yet another embodiment, the polymorphic Form II in the tablet is present in excess of polymorphic Form I. For example, the weight ratio of polymorphic Form II to polymorphic Form I in the tablet is between 99 to 1 and 55 to 45, or may be 60 to 40, 70 to 30, 75 to 25, 80 to 20, 85 to 15, 90 to 10, 95 to 5, or 99 to 1. In yet another embodiment, polymorphic Form I and polymorphic Form II are present in approximately the same amounts in the tablet.

In any of the foregoing tablets, in one variation, the tablet is substantially free of amorphous or non-crystalline (S)-2-(1-(9H-purin-6-ylamino)propyl)-5-fluoro-3-phenylquinazolin-4(3H)-one. In any of the foregoing tablets, in one variation, the unit dosage form is substantially free of a salt of (S)-2-(1-(9H-purin-6-ylamino)propyl)-5-fluoro-3-phenylquinazolin-4(3H)-one (e.g., an HCl salt of (S)-2-(1-(9H-purin-6-ylamino)propyl)-5-fluoro-3-phenylquinazolin-4(3H)-one).

Provided herein are also methods of preparing a tablet comprising polymorphic Form I and polymorphic Form II of (S)-2-(1-(9H-purin-6-ylamino)propyl)-5-fluoro-3-phenylquinazolin-4(3H)-one, wherein the method comprises compressing polymorphic Form I of (S)-2-(1-(9H-purin-6-ylamino)propyl)-5-fluoro-3-phenylquinazolin-4(3H)-one under conditions suitable to produce polymorphic Form II of (S)-2-(1-(9H-purin-6-ylamino)propyl)-5-fluoro-3-phenylquinazolin-4(3H)-one. Suitable conditions may include, for example, applying a force of between about 500 psi and about 5000 psi, or between 1000 psi and about 4500 psi, during the tableting process.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers.

Dragee cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The polymorphs described herein are effective over a wide dosage range and are generally administered in a pharmaceutically effective amount. It will be understood, however, that the amount of the polymorph actually administered will be determined by a physician, in the light of the relevant circumstances, including the condition to be treated, the chosen route of administration, the age, weight, and response of the individual patient, the severity of the patient's symptoms, and the like.

The tablets or pills described herein may be coated or otherwise compounded to provide a dosage form affording the advantage of prolonged action, or to protect from the acid conditions of the stomach. For example, the tablet or pill can comprise an inner dosage and an outer dosage element, the latter being in the form of an envelope over the former. The two elements can be separated by an enteric layer that serves to resist disintegration in the stomach and permit the inner element to pass intact into the duodenum or to be delayed in release. A variety of materials can be used for such enteric layers or coatings, such materials including a number of polymorphic acids and mixtures of polymorphic acids with such materials as shellac, cetyl alcohol, and cellulose acetate.

For example, provided is a unit dosage comprising one or more of the polymorphic forms described herein (e.g., Form I and/or Form II). In one embodiment, the unit dosage comprises substantially pure polymorphic Form I of (S)-2-(1-(9H-purin-6-ylamino)propyl)-5-fluoro-3-phenylquinazolin-4(3H)-one. In other embodiments, the unit dosage comprises substantially pure polymorphic Form II of (S)-2-(1-(9H-purin-6-ylamino)propyl)-5-fluoro-3-phenylquinazolin-4(3H)-one. In yet other embodiments, the unit dosage comprises a mixture of polymorphic Form I and polymorphic Form II of (S)-2-(1-(9H-purin-6-ylamino)propyl)-5-fluoro-3-phenylquinazolin-4(3H)-one.

In one embodiment of the unit dosage, the polymorphic Form I in the composition is present in excess of polymorphic Form II. For example, the weight ratio of polymorphic Form I to polymorphic Form II in the unit dosage is between 99 to 1 and 55 to 45, or may be 60 to 40, 70 to 30, 75 to 25, 80 to 20, 85 to 15, 90 to 10, 95 to 5, or 99 to 1. In one embodiment, the weight ratio of polymorphic Form I to polymorphic Form II is between 90:1 and 99:1. In yet another embodiment, the polymorphic Form II in the unit dosage is present in excess of polymorphic Form I. For example, the weight ratio of polymorphic Form II to polymorphic Form I in the unit dosage is between 99 to 1 and 55 to 45, or may be 60 to 40, 70 to 30, 75 to 25, 80 to 20, 85 to 15, 90 to 10, 95 to 5, or 99 to 1. In yet another embodiment, polymorphic Form I and polymorphic Form II are present in approximately the same amounts in the unit dosage.

In any of the foregoing unit dosage forms, in one variation, the unit dosage form is substantially free of amorphous or non-crystalline (S)-2-(1-(9H-purin-6-ylamino)propyl)-5-fluoro-3-phenylquinazolin-4(3H)-one. In any of the foregoing unit dosage forms, in one variation, the unit dosage form is substantially free of a salt of (S)-2-(1-(9H-purin-6-ylamino)propyl)-5-fluoro-3-phenylquinazolin-4(3H)-one (e.g., an HCl salt of (S)-2-(1-(9H-purin-6-ylamino)propyl)-5-fluoro-3-phenylquinazolin-4(3H)-one). In one embodiment, unit dosage form is a tablet comprising polymorphic Form I and polymorphic Form II of (S)-2-(1-(9H-purin-6-ylamino)propyl)-5-fluoro-3-phenylquinazolin-4(3H)-one, wherein the polymorphic Form II is produced upon applying a force to polymorphic Form I during the tableting process.

Provided herein are also methods of preparing a unit dosage comprising polymorphic Form I and polymorphic Form II of (S)-2-(1-(9H-purin-6-ylamino)propyl)-5-fluoro-3-phenylquinazolin-4(3H)-one, wherein the method comprises compressing polymorphic Form I of (S)-2-(1-(9H-purin-6-ylamino)propyl)-5-fluoro-3-phenylquinazolin-4 (3H)-one under conditions suitable to produce polymorphic Form II of (S)-2-(1-(9H-purin-6-ylamino)propyl)-5-fluoro-3-phenylquinazolin-4(3H)-one. Suitable conditions may include, for example, applying a force of between about 500 psi and about 5000 psi, or between 1000 psi and about 4500 psi, during the tableting process.

Modes of Administration and Dosages

Pharmaceutical compositions including the polymorphic forms described herein can be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral, buccal, sublingual, and rectal administration. Transepithelial administration modalities include, for example, transmucosal administration and transdermal administration. Transmucosal administration includes, for example, enteral administration as well as nasal, inhalation, and deep lung administration; vaginal administration; and buccal and sublingual administration. Transdermal administration includes passive or active transdermal or transcutaneous modalities, including, for example, patches and iontophoresis devices, as well as topical application of pastes, salves, or ointments. Parenteral administration also can be accomplished using a high-pressure technique, e.g., POWDERJECT™.

Moreover, the therapeutic index of the compound having the polymorphic forms described herein can be enhanced by modifying or derivatizing the compound for targeted delivery to cancer cells expressing a marker that identifies the cells as such. For example, the compound can be linked to an antibody that recognizes a marker that is selective or specific for cancer cells, so that the compounds are brought into the vicinity of the cells to exert their effects locally, as previously described. See e.g., Pietersz et al., Immunol. Rev., 129:57 (1992); Trail et al., Science, 261:212 (1993); and Rowlinson-Busza et al., Curr. Opin. Oncol., 4:1142 (1992). Tumor-directed delivery of the compound can enhance the therapeutic benefit by, inter alia, minimizing potential nonspecific toxicities that can result from radiation treatment or chemotherapy. In some embodiments, the compound having a polymorphic form described herein, and radioisotopes or chemotherapeutic agents can be conjugated to the same anti-tumor antibody.

Pharmacokinetic and pharmacodynamic information about the polymorphic forms described herein and the formulation of the compound having a polymorphic form described herein can be collected through preclinical in vitro and in vivo studies, later confirmed in humans during the course of clinical trials. Thus, for the compound having a polymorphic form described herein used in the methods described herein, a therapeutically effective dose can be estimated initially from biochemical and/or cell-based assays. Then, dosage can be formulated in animal models to achieve a desirable circulating concentration range that modulates PI3Kδ expression or activity. As human studies are conducted further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The dosage of such compounds lies preferably within a range of circulating concentrations that include the ED.sub.50 with little or no toxicity.

It should be understood that any effective administration regimen regulating the timing and sequence of doses can be used. A compound having a polymorphic form described herein and pharmaceutical compositions thereof may include those wherein the active ingredient is administered in an effective amount to achieve its intended purpose.

In some embodiments, a "therapeutically effective amount" means an amount sufficient to modulate PI3Kδ expression or activity, and thereby treat an individual suffering an indication, or to alleviate the existing symptoms of the indication. Determination of a therapeutically effective amount is well within the capability of those skilled in the art, especially in light of the detailed disclosure provided herein.

Exemplary dosage levels for a human subject are of the order of from about 0.001 milligram of active agent per kilogram body weight (mg/kg) to about 1000 mg/kg. Typically, dosage units of the active agent comprise from about 0.01 mg to about 1000 mg, preferably from about 0.1 mg to about 100 mg, depending upon the indication, route of administration, and severity of the condition, for example. Depending on the route of administration, a suitable dose can be calculated according to body weight, body surface area, or organ size. The final dosage regimen is determined by the attending physician in view of good medical practice, considering various factors that modify the action of drugs, e.g., the specific activity of the compound, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing depends on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks.

Bioequivalents of the Polymorphs

Also provided herein are polymorphs that are bioequivalent to the polymorphic Form I and the polymorphic Form II described herein.

In certain embodiments, bioequivalence between two polymorphs refers to polymorphs having substantially similar bioavailability, substantially similar efficacy, substantially similar safety profiles, or a combination thereof.

In yet other embodiments, bioequivalence refers to polymorphs that exhibit substantially similar pharmacokinetic profiles or therapeutic effects. Bioequivalence may be demonstrated through several in vivo and in vitro methods. These methods may include, for example, pharmacokinetic, pharmacodynamic, clinical and in vitro studies. In some embodiments, bioequivalence can be demonstrated using any suitable pharmacokinetic measures or combination of pharmacokinetic measures known in the art, including loading dose, steady-state dose, initial or steady-state concentration of drug, biological half-life, elimination rate, area under the curve (AUC), clearance, the peak blood or plasma concentration ($C_{max}$), time to peak concentration ($T_{max}$), bioavailability and potency. In some embodiments, bioequivalence is achieved with similar dosing amounts. In alternative embodiments, bioequivalence is achieved with different dosing amounts.

Therapeutic Use of the Polymorphs and Compositions Thereof

Provided are also a use of the polymorphs or compositions thereof described herein to selectively or specifically inhibiting PI3Kδ activity therapeutically or prophylactically. The method comprises administering the polymorphs or compositions thereof to an individual in need thereof in an amount sufficient to inhibit PI3Kδ activity. The method can be employed to treat humans or animals suffering from, or subject to, a condition whose symptoms or pathology is mediated by PI3Kδ expression or activity.

In some embodiments, "treating" refers to preventing a disorder from occurring in an animal that can be predisposed to the disorder, but has not yet been diagnosed as having it; inhibiting the disorder, i.e., arresting its development; relieving the disorder, i.e., causing its regression; or ameliorating the disorder, i.e., reducing the severity of symptoms associated with the disorder. In some embodiments, "disorder" is intended to encompass medical disorders, diseases, conditions, syndromes, and the like, without limitation.

The methods disclosed in the application embrace various modes of treating an animal subject, preferably a mammal, more preferably a primate, and still more preferably a human. Among the mammalian animals that can be treated are, for example, humans; companion animals (pets), including dogs and cats; farm animals, including cattle, horses, sheep, pigs, and goats; laboratory animals, including rats, mice, rabbits, guinea pigs, and nonhuman primates; and zoo specimens. Among the non-mammalian animals that can be treated include, for example, birds, fish, reptiles, and amphibians.

In one aspect, the polymorphs and compositions thereof described herein can be employed in methods of inhibiting the growth or proliferation of cancer cells of hematopoietic origin, such as cancer cells. In some embodiments, the cancer cells are of lymphoid origin, and in specific embodiments, the cancer cells are related to or derived from B lymphocytes or B lymphocyte progenitors. Cancers amenable to treatment using the method disclosed in the application include, without limitation, lymphomas (e.g., malignant neoplasms of lymphoid and reticuloendothelial tissues, such as Burkitt's lymphoma, Hodgkins' lymphoma, non-Hodgkins' lymphomas, lymphocytic lymphomas); multiple myelomas; leukemias (e.g., lymphocytic leukemias, chronic myeloid (myelogenous) leukemias). Other cancer cells, of hematopoietic origin or otherwise, that express p110δ also can be treated by administration of the polymorphs and compositions thereof described herein.

In particular embodiments, the cancer is leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL).

In another aspect, the polymorphs and compositions thereof described herein can be employed in methods of treating a patient with a cancer. In some embodiments, the cancer is a hematologic malignancy. In specific embodiments, the hematologic malignancy is leukemia (e.g., chronic lymphocytic leukemia) or lymphoma (e.g., non-Hodgkin's lymphoma).

In yet another aspect, provided are methods of treating an individual having a PI3K-mediated disorder by administering polymorphic Form I, polymorphic Form II, or a mixture of polymorphic Form I and polymorphic Form II of (S)-2-(1-(9H-purin-6-ylamino)propyl)-5-fluoro-3-phenylquinazolin-4(3H)-one to the individual. Provided are also methods of modulating PI3K an individual by administering polymorphic Form I, polymorphic Form II, or a mixture of polymorphic Form I and polymorphic Form II of (S)-2-(1-(9H-purin-6-ylamino)propyl)-5-fluoro-3-phenylquinazolin-4(3H)-one to the individual. In one variation, the polymorphic Form I, polymorphic Form II, or a mixture of polymorphic Form I and polymorphic Form II of (S)-2-(1-(9H-purin-6-ylamino)propyl)-5-fluoro-3-phenylquinazolin-4(3H)-one is substantially free of other polymorphic forms. In another variation, the polymorphic Form I, polymorphic Form II, or a mixture of polymorphic Form I and polymorphic Form II of (S)-2-(1-(9H-purin-6-ylamino)propyl)-5-fluoro-3-phenylquinazolin-4(3H)-one is substantially free of amorphous or non-crystalline (S)-2-(1-(9H-purin-6-ylamino)propyl)-5-fluoro-3-phenylquinazolin-4(3H)-one. In another variation, the polymorphic Form I, polymorphic Form II, or a mixture of polymorphic Form I and polymorphic Form II of (S)-2-(1-(9H-purin-6-ylamino)propyl)-5-fluoro-3-phenylquinazolin-4(3H)-one is substantially free of amorphous or non-crystalline (S)-2-(1-(9H-purin-6-ylamino)propyl)-5-fluoro-3-phenylquinazolin-4(3H)-one substantially free of a salt of (S)-2-(1-(9H-purin-6-ylamino)propyl)-5-fluoro-3-phenylquinazolin-4(3H)-one (e.g., a HCl salt of (S)-2-(1-(9H-purin-6-ylamino)propyl)-5-fluoro-3-phenylquinazolin-4(3H)-one).

In any of the foregoing methods, the polymorphic form may be administered to the individual as unit dosage, for example in the form of a tablet. Variations in which polymorphic Form II are administered in the form a tablet, the polymorphic Form II is produced upon compression of polymorphic Form I in the tableting process. For example, a force of between about 500 psi and about 5000 psi, between about 500 psi and about 5000 psi, or between 1000 psi and about 4500 psi, may be applied during the tableting process.

Articles of Manufacture and Kits

Compositions comprising the polymorphs disclosed herein and formulated in a pharmaceutically acceptable carrier can be prepared, placed in an appropriate container, and labeled for treatment of an indicated condition. Accordingly, there also is contemplated an article of manufacture, such as a container comprising a dosage form of one or more polymorphic forms of (S)-2-(1-(9H-purin-6-ylamino)propyl)-5-fluoro-3-phenylquinazolin-4(3H)-one, and a label containing instructions for use of the compound.

In some embodiments, the article of manufacture is a container comprising a dosage form of polymorphic Form I of (S)-2-(1-(9H-purin-6-ylamino)propyl)-5-fluoro-3-phenylquinazolin-4(3H)-one, and one or more pharmaceutically acceptable carriers or excipients. In other embodiments, the article of manufacture is a container comprising a dosage form of polymorphic Form II of (S)-2-(1-(9H-purin-6-ylamino)propyl)-5-fluoro-3-phenylquinazolin-4(3H)-one, and one or more pharmaceutically acceptable carriers or excipients. In yet other embodiments, the article of manufacture is a container comprising a dosage form of a mixture of polymorphic Form I and polymorphic Form II of (S)-2-(1-(9H-purin-6-ylamino)propyl)-5-fluoro-3-phenylquinazolin-4(3H)-one, and one or more pharmaceutically acceptable carriers or excipients. In one embodiment of the articles of manufacture described herein, the dosage form is a tablet.

Kits also are contemplated. For example, a kit can comprise a dosage form of a pharmaceutical composition and a package insert containing instructions for use of the composition in treatment of a medical condition. The instructions for use in the kit may be for treating a PI3K-mediated disorder, including, for example, a hematologic malignancy.

In certain embodiments, the instructions for use in the kit may be for treating leukemia. In one embodiment, the instructions for use in the kit may be for treating non-Hodgkin's lymphoma (NHL) or chronic lymphocytic leukemia (CLL).]. In certain embodiments, conditions indicated on the label can include, for example, treatment of cancer.

EXAMPLES

The following examples are provided to further aid in understanding the embodiments disclosed in the application, and presuppose an understanding of conventional methods well known to those persons having ordinary skill in the art to which the examples pertain. The particular materials and conditions described hereunder are intended to exemplify particular aspects of embodiments disclosed herein and should not be construed to limit the reasonable scope thereof.

The polymorphic forms of (S)-2-(1-(9H-purin-6-ylamino)propyl)-5-fluoro-3-phenylquinazolin-4(3H)-one were characterized by various analytical techniques, including X-ray powder diffraction pattern (XPPD), differential scanning calorimetry (DSC), and thermographic analysis (TGA) using the procedures described below.

X-Ray Powder Diffraction:

XRPD patterns were collected using a PANalytical X'Pert MPD Pro Powder X-Ray Diffractometer configured with reflectance stage with spinning, data acquisition range: 2-40 degrees 2θ, Copper (Cu) anode; Kα1/Kα2 radiation; tube current 40 mA; tube tension 45 kV; automatic divergence and anti-scatter slits. Samples were prepared for analysis by distributing solid material as a thin layer on a silicon holder. Each holder was mounted on a reflectance/transmittance stage and rotated during data acquisition.

Differential Scanning Calorimetry:

DSC was performed using a TA Instruments Q2000 DSC instrument. The sample was placed into an aluminum DSC pan, and the weight accurately recorded. The pan was covered with a lid, and then either crimped or hermetically sealed. The same cell was equilibrated at 25° C. and heated under a nitrogen purge at a rate of 10° C./min, up to a final temperature of 300° C. Indium was used as the calibration standard.

Thermogravimetric Analysis:

TGA was performed using a TA Instruments Q5000 TGA instrument. Each sample was placed in an aluminum sample pan and inserted into the TG furnace. The furnace was first equilibrated at 25° C., and then heated under nitrogen at a rate of 10° C./min, up to a final temperature of 300° C. The TGA furnace was calibrated using the magnetic Curie point method.

Example 1

Preparation of Form I 20.6 g of (S)-2-(1-(9H-purin-6-ylamino)propyl)-5-fluoro-3-phenylquinazolin-4(3H)-one was suspended in a mixture of 164 mL methanol and 36 mL water. Under stirring, the mixture was heated to reflux (about 66° C.) for about 1.5 hours. Upon complete dissolution water was slowly added. The solution temperature was allowed to reach about 75° C. When about 100 mL water was added solids were formed and the solution was then slowly cooled to about 30-35° C. Form I was isolated by vacuum filtration at about 35° C., and dried under vacuum at about 40° C. The dried solids were analyzed by XRPD and DSC. FIGS. 1A and 1B and depict the XRPD and DSC patterns of polymorphic Form I.

Example 2

Preparation of Form II from Form I by Grinding

Form I was prepared as described in Example 1. Form I solids were ball milled in batches for 10 minutes at 30 Hz. Samples were analyzed by XRPD. Table 1 below summarizes the amount of polymorphic Form II observed from conversion of polymorphic Form I.

TABLE 1

Ball Milling Experiments

| Scale (g) | Solvents | Temp (° C.) | Stirring mode | Time (days) | Form II Product (g) |
|---|---|---|---|---|---|
| 10 | 20 vol acetone | 28 | magnetic | 6 | 6.9 |
| 10 | 20 vol acetone | 28 | magnetic | 5 | 5 |
| 10 | 20 vol acetone + 20 vol MTBE | 28 | magnetic | 7 | 6.5 |
| 10 | acetone | 10/28 | magnetic | 5 | 6 |
| 37 | 14 vol acetone + 14 vol MTBE | 10/28 | Half moon blade + magnetic | 7 | 31.3 |

Results in Table 1 showed that Form I was successfully converted into Form II using the ball milling technique.

Figure 3:
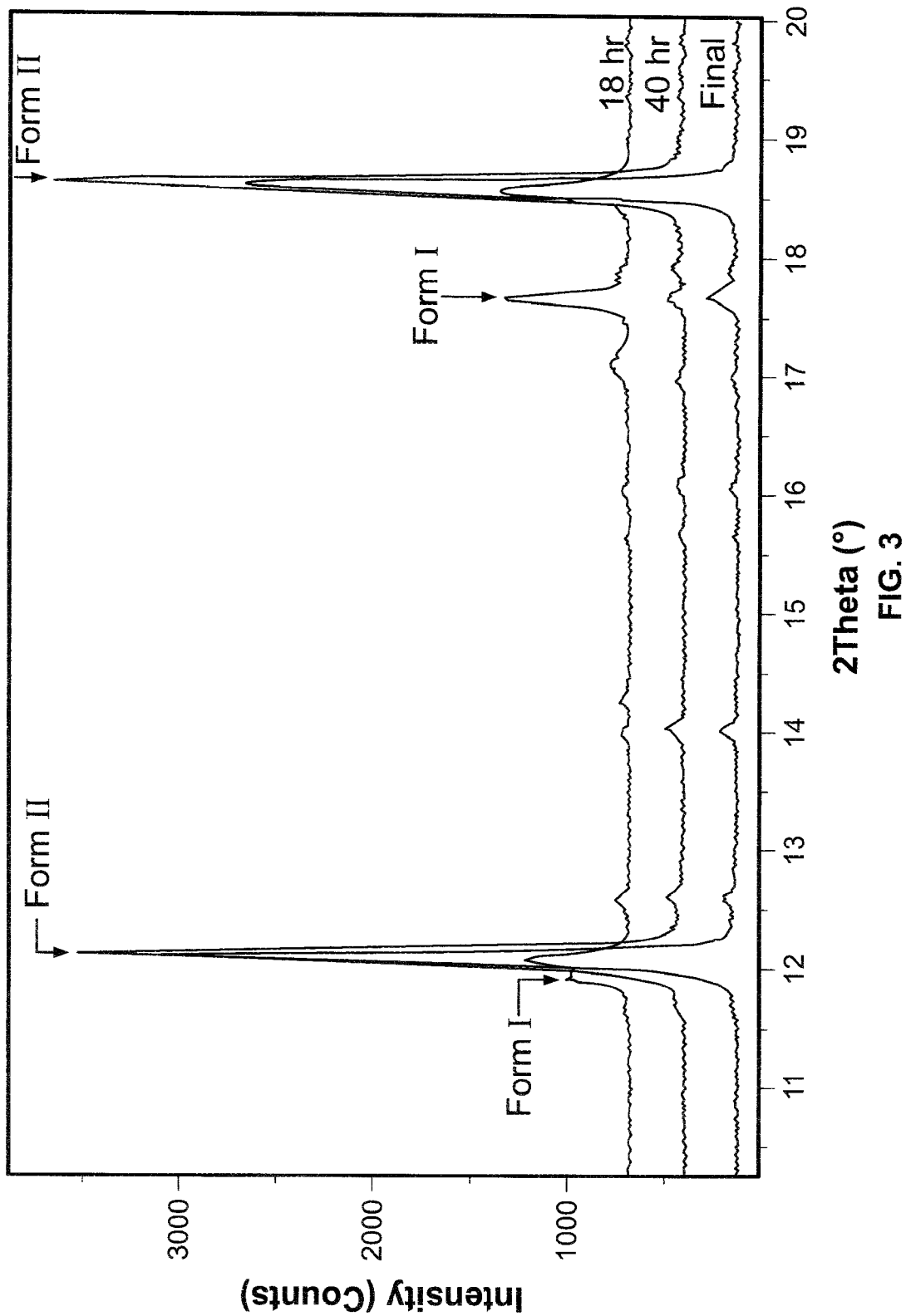
FIG. 3 shows XRPD patterns of Form I and Form II after 18 hours and 40 hours, where the Form I solids were ball milled and stirred in acetone at 28° C.

Additionally, 10 g of Form I was ball milled at 30 Hz for 10 minutes and stirred in 300 mL of acetone at 28° C. As seen in FIG. 3, about 50% conversion of Form I into Form II was observed after 18 hours, and about 90% conversion was observed after 40 hours.

Example 3

Comparison of Dry and Wet Grinding in Conversion of Form I into Form II

Form I of (S)-2-(1-(9H-purin-6-ylamino)propyl)-5-fluoro-3-phenylquinazolin-4(3H)-one was pre-processed using various grinding methods before forming a slurry in either acetone or THF and stirring at either room temperature, 22° C. or 30° C. Table 2 below summarizes the conditions and the result of the experiment. As used in this Example, "enriched" describes a sample that contains substantially more Form II than Form I.

Figure 4:
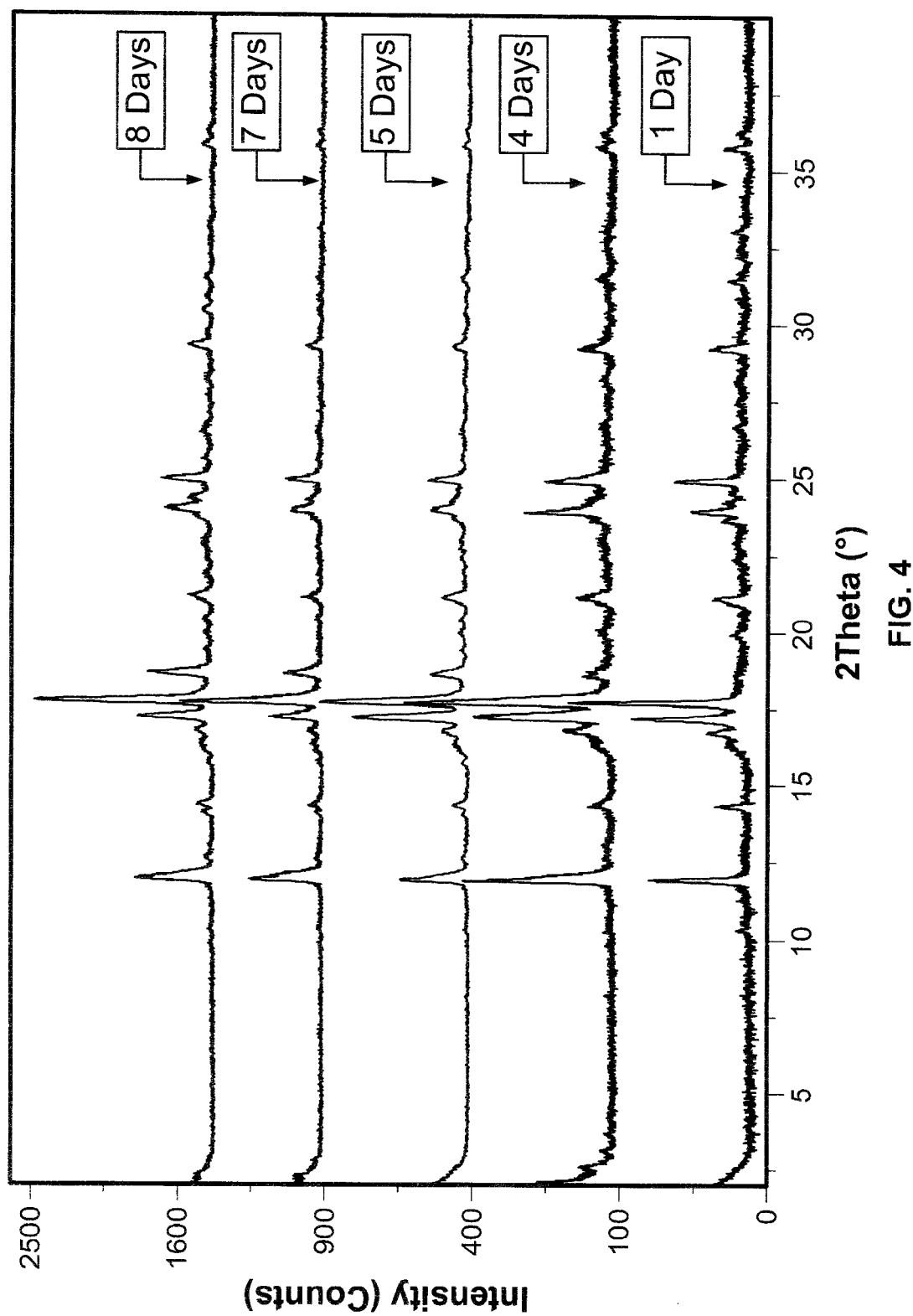
FIG. 4 shows XRPD patterns of polymorphic forms after wet grinding of Form I in acetone over a period of 1-8 days.

The results in Table 2 above show that some Form I was converted into Form II at small scale using dry grinding with mortar and pestle. In addition, Form I was converted into Form II using jet milling after several days. Additionally, FIG. 4 shows an XRPD comparison of polymorphic forms over a period of 8 days, where Form I solids were suspended in acetone after wet grinding.

Example 4

Preparation of Form II from Form I by Compression

Form I of (S)-2-(1-(9H-purin-6-ylamino)propyl)-5-fluoro-3-phenylquinazolin-4(3H)-one was subjected to high pressure in a hydraulic tablet press (ENERPAC Model P142 hydraulic press; #9166 0.275 inch punch) as shown in Table 3 below. The relaxation time is the time between compressions. A sample of the compressed solids was analyzed by XRPD and DSC. FIGS. 2A and 2B depict the XRPD and DSC patterns of polymorphic Form II.

TABLE 3

Compression conditions and observations

| (S)-2-(1-(9H-purin-6-ylamino)propyl)-5-fluoro-3-phenylquinazolin-4(3H)-one (mg) | Pressure (psi) | Duration (min) | Relaxation Time (hours) | XRPD |
|---|---|---|---|---|
| NA | atm | — | — | Form I & minor II |
| ~150 | atm | — | — | Form I and II (excess of I) |
| ~160 | 4500 | <0.5 | — | Form I and II (excess of I) |
| ~150 | 1000 | <0.5 | 24 | Form I and II (excess of I) |
| 163 | 2000 | 5 | 72 | I & II (~1:1) |
| 167 | 2000 | 10 | 72 | I & II (~1:1) |
| 164 | 3000 | 5 | 2 | I & II (~1:1) |
| 168 | 3000 | 10 | 2 | I & II (~1:1) |
| 171 | 3000 | 60 | 72 | I & II (excess of II) |

Figure 5A:
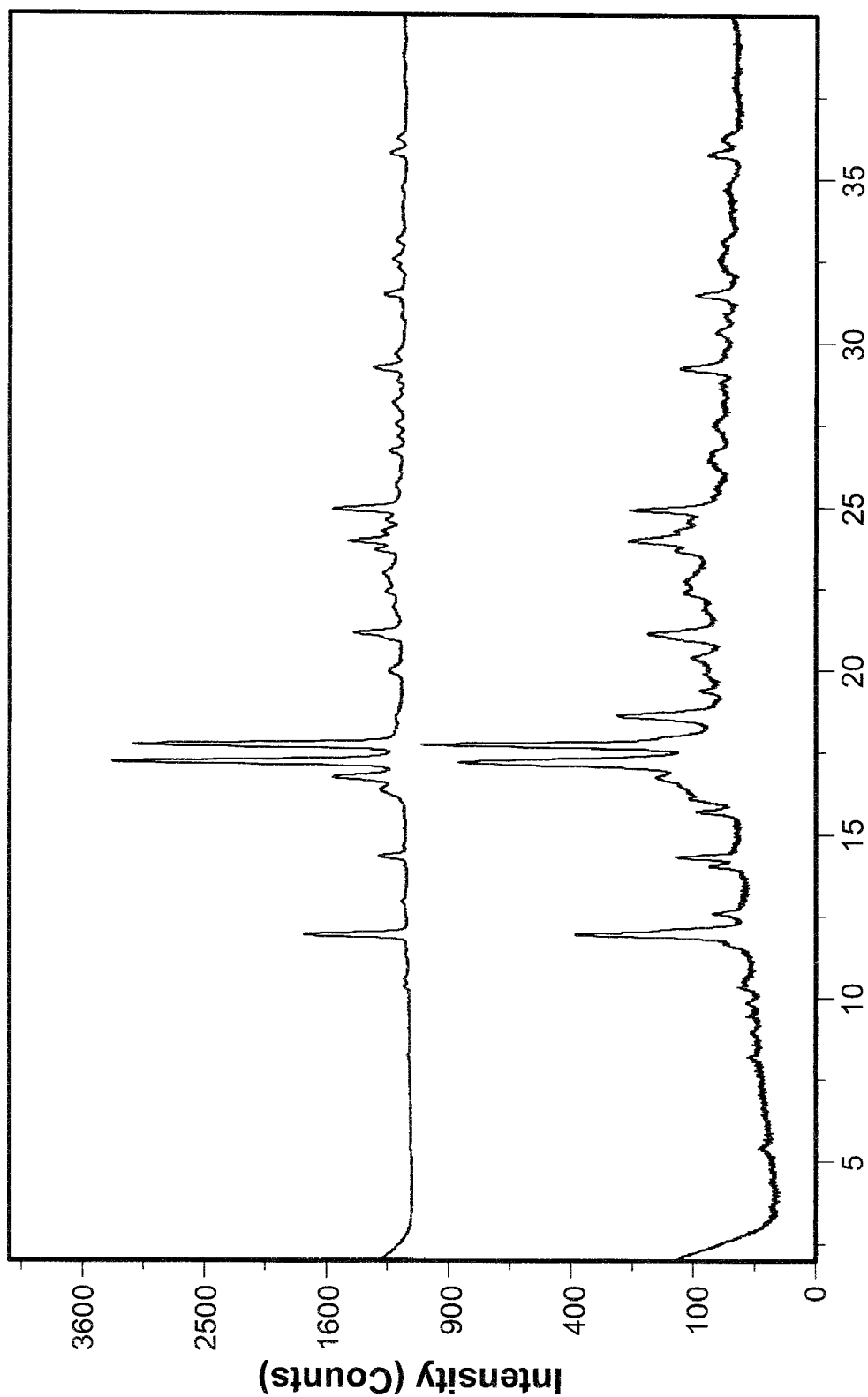
FIG. 5A shows an XRPD pattern of Form I solids before compression (top) and after compression (bottom).
Figure 5B:
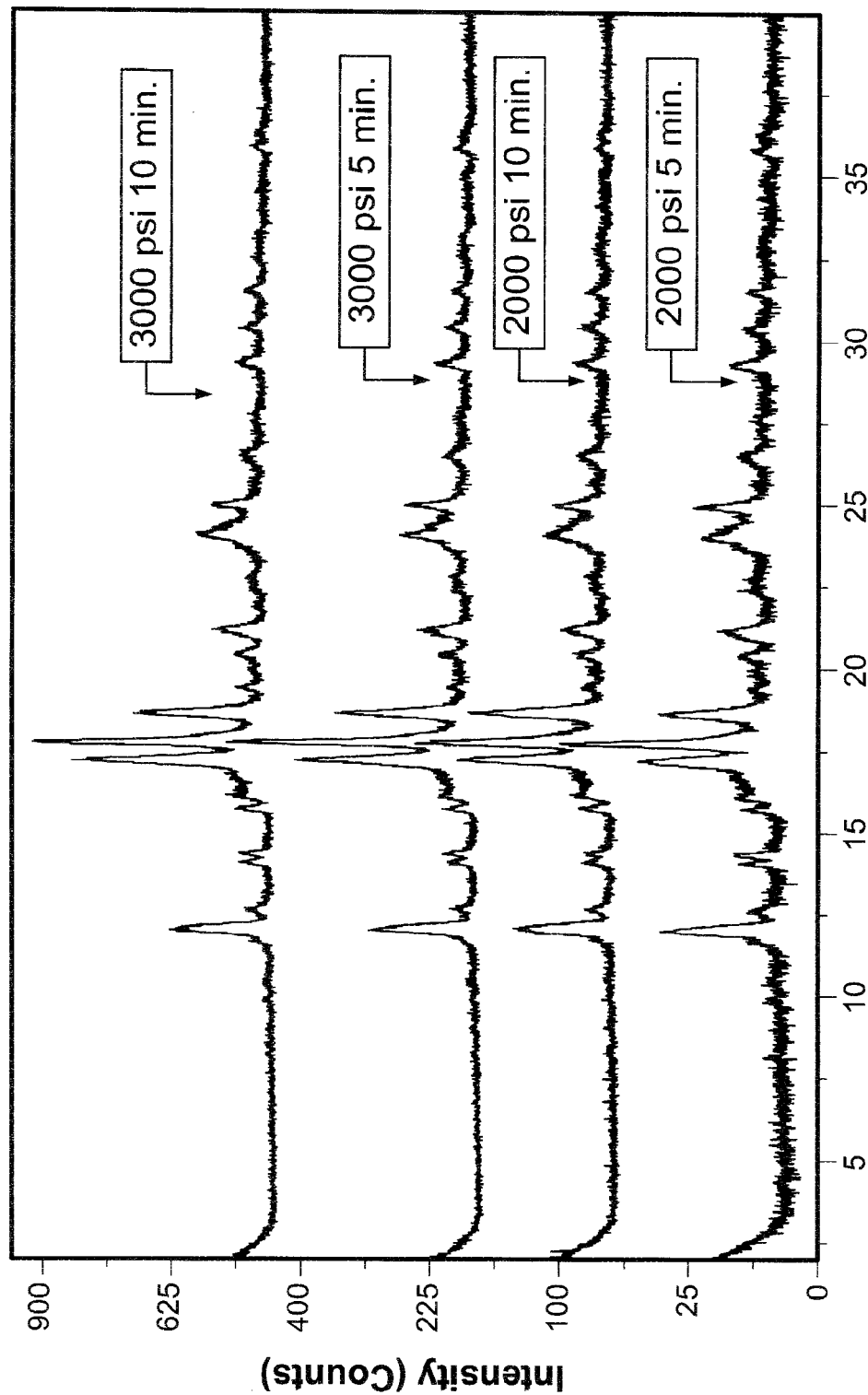
FIG. 5B shows XRPD patterns of compressed Form I solids at various pressures and duration, where from top to bottom the patterns are for the pressures and duration as indicated.

Results of Table 3 indicated that Form I was partially converted to Form II during compression at the 100-200 mg scale. FIGS. 5A and 5B show XRPD patterns for two lots of Form I solids before and after compression at various

TABLE 2

Dry and Wet Grinding Experiments

Figure 5C:
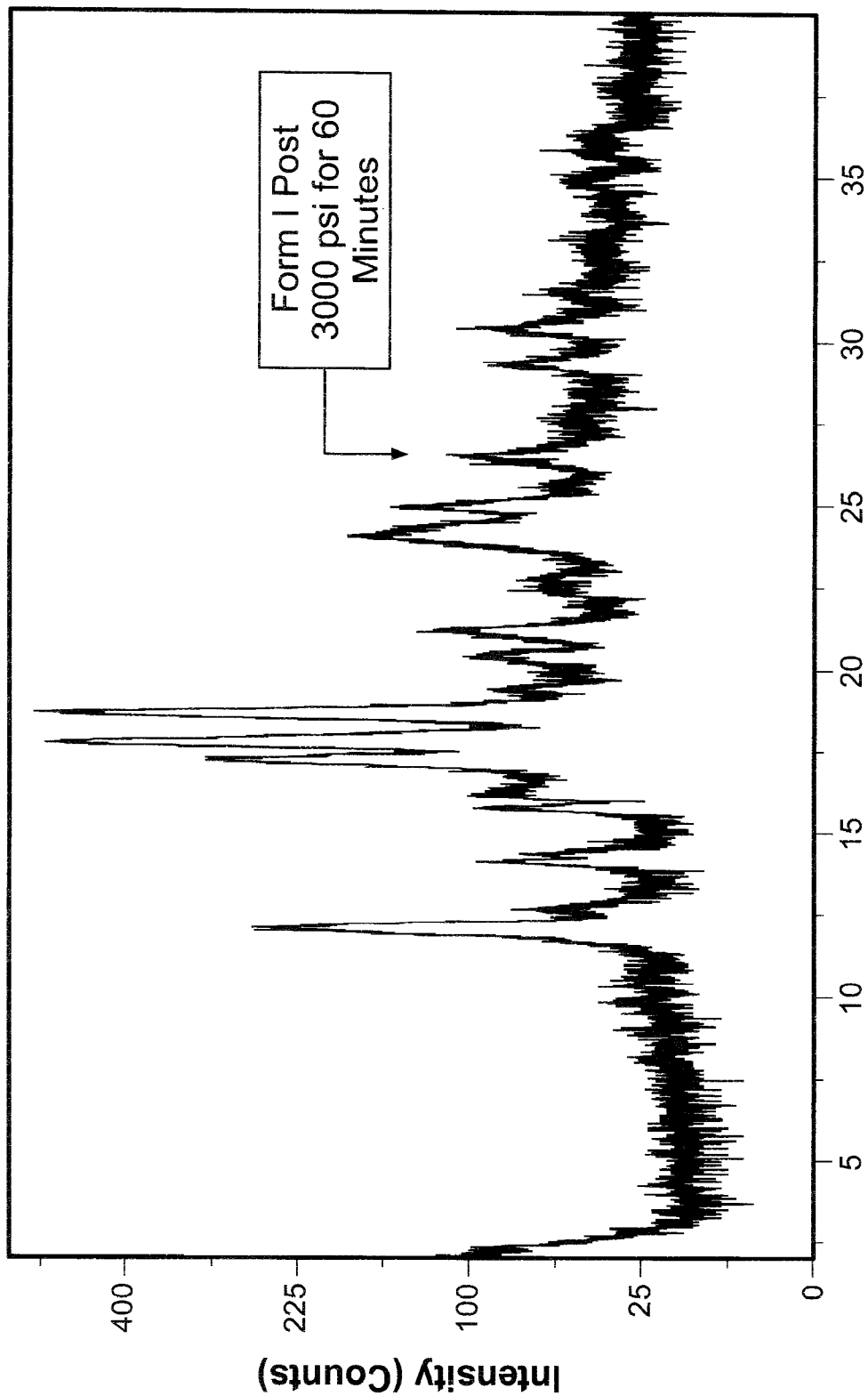
FIG. 5C shows an XRPD of Form I compressed at 3000 psi for 60 minutes.

| Scale (g) | Pre-processing | Slurry Solvent | Temp (° C.) | Stirring condition | Form II content |
|---|---|---|---|---|---|
| 0.2 | Dry/wet grinding | acetone | r.t. | magnetic | Enriched after 1 day<br>Highly enriched after 2 days |
| 1 | Dry/wet grinding | acetone | r.t. | magnetic | Trace amount after 1 week |
| 20 | Dry grinding | acetone | 30 | overhead | Undetectable after 3 days |
| 5 | High shear wet mill | acetone | 30 | overhead | Undetectable after 3 days |
| 1 | High shear mixer (dry) | acetone | r.t. | magnetic | Trace amount after 1 day |
| 1 | High shear mixer (dry) | THF | r.t. | magnetic | Trace amount after 1 day |
| 1 | Jet milled | acetone | 22 | magnetic | Small amount after 1 day<br>Enriched after 4 days | r.t. = room temperature pressures, respectively. FIG. 5C shows an XRPD pattern of compressed Form I solids using 3000 psi for 60 minutes. With reference to this figure, conversion of over 50% of Form I to Form II was observed under this condition.

Example 5

Effect of Temperature on Form Conversion in Acetone Suspension

Form I of (S)-2-(1-(9H-purin-6-ylamino)propyl)-5-fluoro-3-phenylquinazolin-4(3H)-one was suspended in acetone at a concentration of 50 mg/mL, and stirred magnetically over a period of 5-6 days. Four experiments at different temperature were conducted.

Table 4 summarizes the reaction conditions and the amount of polymorphic forms observed for each of the four experiments. As used in this Example, "Enriched II" described a sample that contains substantially more Form II than Form I.

TABLE 4

| Form I Suspensions in Acetone at temperature between 27° C. and 37° C. | | | |
|---|---|---|---|
| (S)-2-(1-(9H-purin-6-ylamino)propyl)-5-fluoro-3-phenylquinazolin-4(3H)-one (mg/mL) | Temp (° C.) | Suspension Time (Days) | |
| | | 5 | 6 |
| 52 | 37 | — | Form I |
| 52 | 33 | — | Form I |
| 50 | 30 | Enriched II | — |
| 51 | 27 | Enriched II | — |

From the results in Table 4 above, it was unexpectedly observed that the rate of conversion from Form I to Form II at 27° C. and 30° C. was higher than the rate of conversion at 33° C. and 37° C.

Example 6

Effect of Temperature on Form Conversion of Solids

Figure 6:
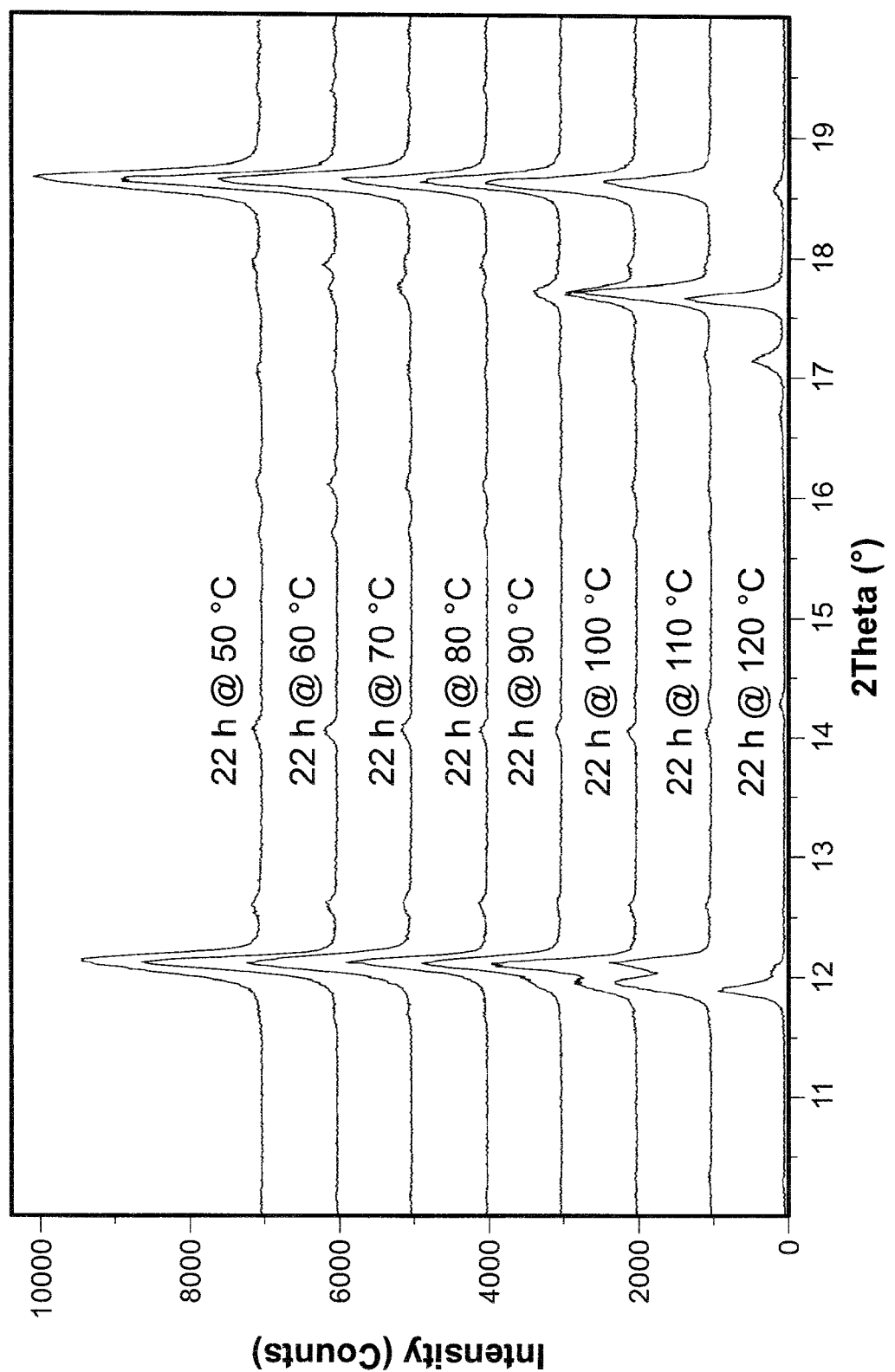
FIG. 6 shows XRPD patterns of Form I versus Form II at different temperatures, where from top to bottom the patterns are for the temperature as indicated.

DSC indicated close melting points for each polymorph and a solid-solid transition in Form II at about 115° C. to produce Form I. To confirm this finding, 200-500 g of Form I of (S)-2-(1-(9H-purin-6-ylamino)propyl)-5-fluoro-3-phenylquinazolin-4(3H)-one was heated at 50° C., 60° C., 70° C., 80° C., 90° C., 100° C., 110° C. and 120° C. jacket temperature using Destiny for 22 hours. Samples were analyzed by X-ray powder diffraction pattern, which are shown in FIG. 6. With reference to this figure, conversion from Form I to Form II was observed at around 90° C.

Example 7

Hydrate Screen

About 50 mg of Form I of (S)-2-(1-(9H-purin-6-ylamino)propyl)-5-fluoro-3-phenylquinazolin-4(3H)-one was slurried in either (A) a 1-mL mixture of a isopropyl alcohol (IPA) and water, or (B) a 1-mL mixture of ethanol and water, for several days at room temperature. The results of the IPA/water and ethanol/water hydrate screens are summarized in Tables 5 and 6, respectively. As used herein, water activity ($a_w$) in liquid phase corresponds to relative humidity in the atmosphere. For example, 0.5 $a_w$ is equivalent to 50% relative humidity.

TABLE 5

| Hydrate screen results in IPA/water system | | | | | | | |
|---|---|---|---|---|---|---|---|
| (S)-2-(1-(9H-purin-6-ylamino)propyl)-5-fluoro-3-phenylquinazolin-4(3H)-one (mg) | IPA/water $a_w$ (1 mL) | IPA (mL) | Water (mL) | 48 Hour Solubility | 48 Hour XRPD | 15-16 Day Solubility | 15-16 Day XRPD |
| 86 | 0.2 | 0.16 | 9.84 | 24 | Form I & II | 20 | Form I & II |
| 93 | 0.3 | 0.27 | 9.73 | 19 | Form I & II | 19 | Form I & II |
| 85 | 0.4 | 0.4 | 9.60 | 18 | Form I & II | 20 | Form I & II |
| 113 | 0.5 | 0.56 | 9.44 | 23 | Form I & II | 20 | Form I & II |
| 88 | 0.6 | 0.76 | 9.24 | 23 | Form I & II | 24 | Form I & II |
| 125 | 0.7 | 1.05 | 8.95 | 9.8 | Form III | 8.7 | Form III |
| 138 | 0.8 | 1.59 | 8.41 | 11 | Form III | 9.5 | Form III |
| 121 | 0.9 | 6.62 | 3.38 | 1 | Form III | 1 | Form III |

TABLE 6

| Hydrate screen results in ethanol/water system | | | | | | | |
|---|---|---|---|---|---|---|---|
| (S)-2-(1-(9H-purin-6-ylamino)propyl)-5-fluoro-3-phenylquinazolin-4(3H)-one (mg) | Ethanol/Water ($a_w$) | Form | TGA mass loss by 125° C. | % water (KF) | % ethanol (GC) | % ethanol (NMR) | % ethanol (SCXC) |
| 246 | 0.7 | VII | 16.41 | 14.2 | TBD | 4.9 | TBD |
| 281 | 0.8 | VII | 16.45 | 17.8 | TBD | 4.0 | NA |
| 295 | 0.9 | I & VII | NA | NA | NA | NA | NA |

Results in Table 5 show that, when water activity in an IPA/water system was below 0.7, Form I was observed to slowly convert to Form II. Also, when water activity in IPA/water system was 0.7 to 0.9, a new crystalline Form III was observed. Form III of (S)-2-(1-(9H-purin-6-ylamino) propyl)-5-fluoro-3-phenylquinazolin-4(3H)-one is a mixed solvate/hydrate.

In an ethanol/water system, when water activity was from 0.2 to 0.4, Form I was slowly converted to Form II (data not shown in Table 6 above). Additionally, when water activity was 0.5 and 0.6, no conversion was observed (data not shown in Table 6 above). Table 6 shows that, when water activity was 0.7 and 0.8, a new crystalline Form VII was observed. Form VII of (S)-2-(1-(9H-purin-6-ylamino)propyl)-5-fluoro-3-phenylquinazolin-4(3H)-one was a mixed water/ethanol solvate.

Example 8

Crystal Structure Analysis

Polymorphic Forms I, III, IV and V of (S)-2-(1-(9H-purin-6-ylamino)propyl)-5-fluoro-3-phenylquinazolin-4(3H)-one were analyzed by single crystal X-ray crystallography. Polymorphic Form II was analyzed by capillary XRPD. Table 7 summarizes crystal structure data for these five polymorphs of (S)-2-(1-(9H-purin-6-ylamino)propyl)-5-fluoro-3-phenylquinazolin-4(3H)-one.

TABLE 7

Crystal unit cell parameters

| | | Unit Cell Dimensions | | | | | |
|---|---|---|---|---|---|---|---|
| | | axis length (Å) | | | axis angle (°) | | |
| Form | Density g/cm$^3$ | a | b | c | α | β | γ |
| I anhydrous | 1.297 | 12.6971 (7) | 11.3577 (8) | 15.2065 (10) | 90.00 | 104.112 | 90.00 |
| II anhydrous | 1.299 | 9.1183 (3) | 11.3299 (3) | 20.7936 (5) | 90.00 | 98.498 | 90.00 |
| III IPA/water | 1.323 | 8.6133 (4) | 11.0763 (5) | 14.3996 (7) | 99.457 | 93.897 | 107.275 |
| IV DMF | 1.382 | 7.9394 (5) | 16.9606 (11) | 17.4405 (13) | 90.00 | 90.00 | 90.00 |
| V DMSO | 1.350 | 9.2354 (3) | 9.7692 (4) | 35.4252 (12) | 90.00 | 90.00 | 90.00 |

Example 9

Monitoring of Form Conversion

Conversion of Form I into Form II of (S)-2-(1-(9H-purin-6-ylamino)propyl)-5-fluoro-3-phenylquinazolin-4(3H)-one was monitored using three techniques: (1) a Lasentec Focused Beam Reflectance Measurement (FBRM) probe, (2) microscopy, and (3) XRPD. Form I solids (1 g and 10 g) were first ball milled for 10 minutes, and then slurried in 20 volumes of acetone at 28° C.

Figure 7:
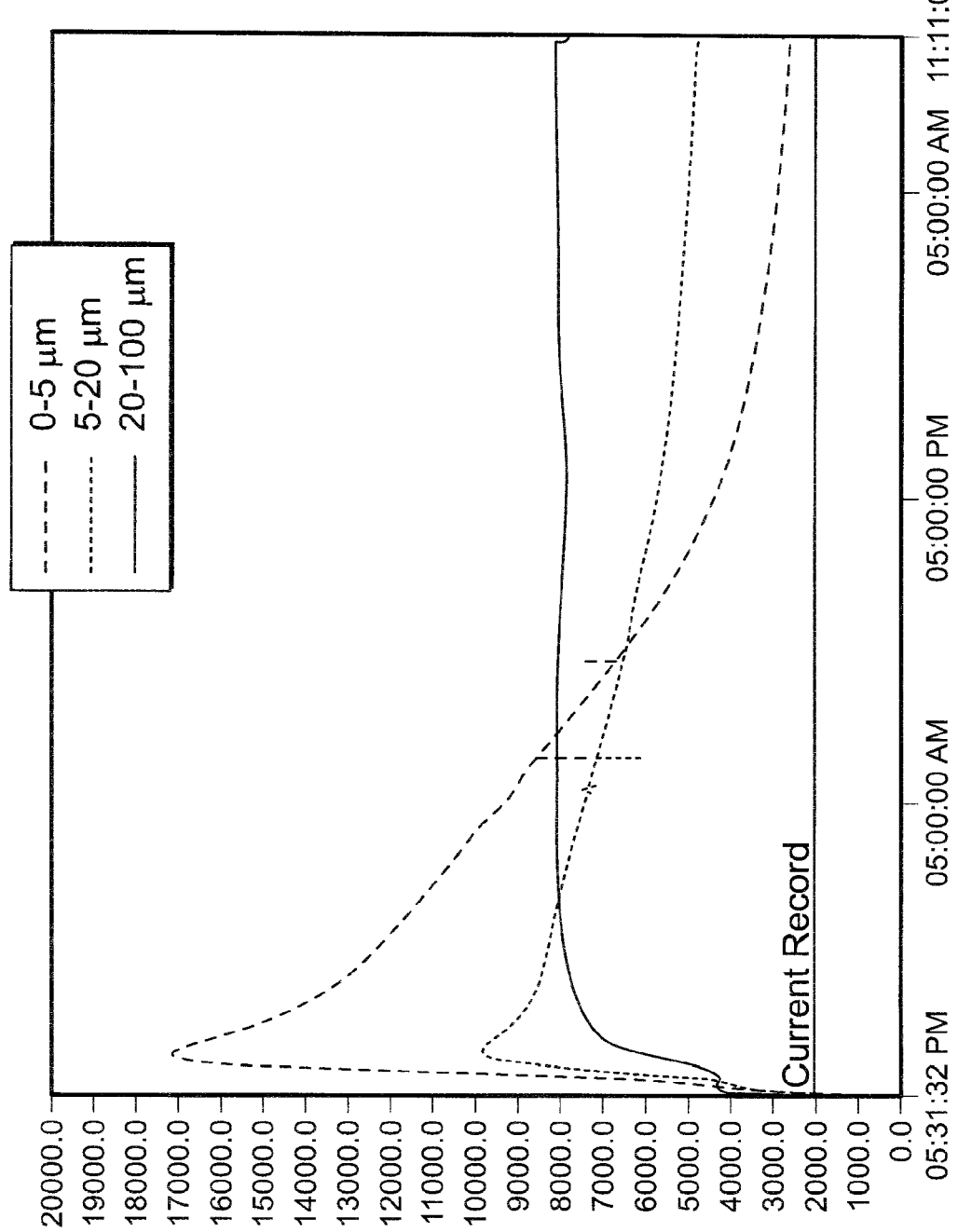
FIG. 7 is a graph showing the trend of chord length (related to particle size) distribution during the conversion of ball milled Form I to Form II.

FBRM Probe:

The conversion of Form I into Form II was monitored using a Lasentec FBRM probe. FBRM monitors the particle counts and size during the run. FIG. 7 shows three distinct regions as represented by the three arrows.

Region 1: the solids after ball milling broken up and partially dissolved

Region 2: Nucleation of form I (potentially also form II)

Region 3: Conversion of form I to form II

FIG. 7 shows the trend of chord length (related to particle size) distribution during the conversion of ball milled form I to form II.

Microscopy:

After ball milling, the solids were observed to contain a significant amount of amorphous material, in addition to Form I and possibly Form II seed. When slurried in acetone, the amorphous material dissolved and precipitated as Form I (majority) and Form II. At the last stage, Form I converts to Form II although some Form I crystals remain.

Figure 8:
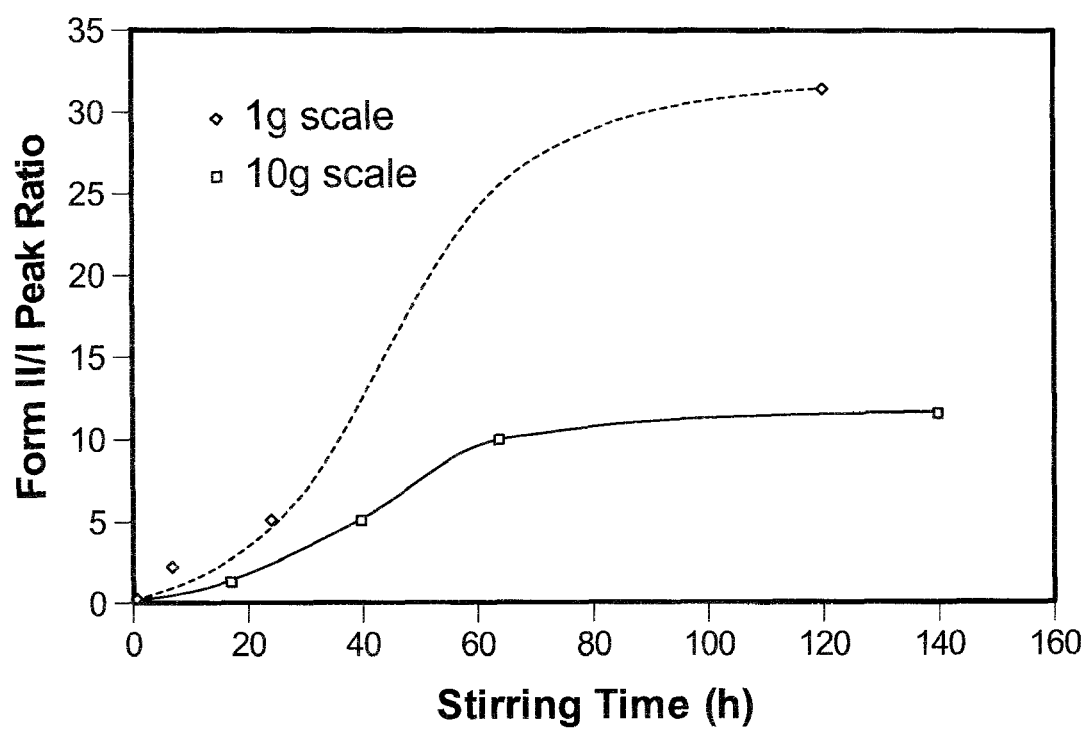
FIG. 8 is a graph showing Form II and Form I peak ratio (the peaks at 17.8 and 18.6 degrees) during the conversion of ball milled Form I to Form II at 1 g and 10 g scales.

XRPD:

The conversion of Form I into Form II was also monitored by XRPD. The XRPD analysis of the slurry in acetone showed that conversion was fast at first and then subsequently slowed down. FIG. 8 shows qualitative changes of solid form versus time, which is in contrast with typical systems where conversion starts slowly and accelerate all the way to the end.

Example 10

Anhydrous Forms and Solid-Solid Transitions of Polymorphs

The TGA traces shown in FIGS. 1B and 2B for polymorphic Form I and polymorphic Form II, respectively, support the characterization of anhydrous solids. These figures show minor mass loss below about 125° C.

Example 11

Hygroscopicity of Form I and Form II

Figure 9A:
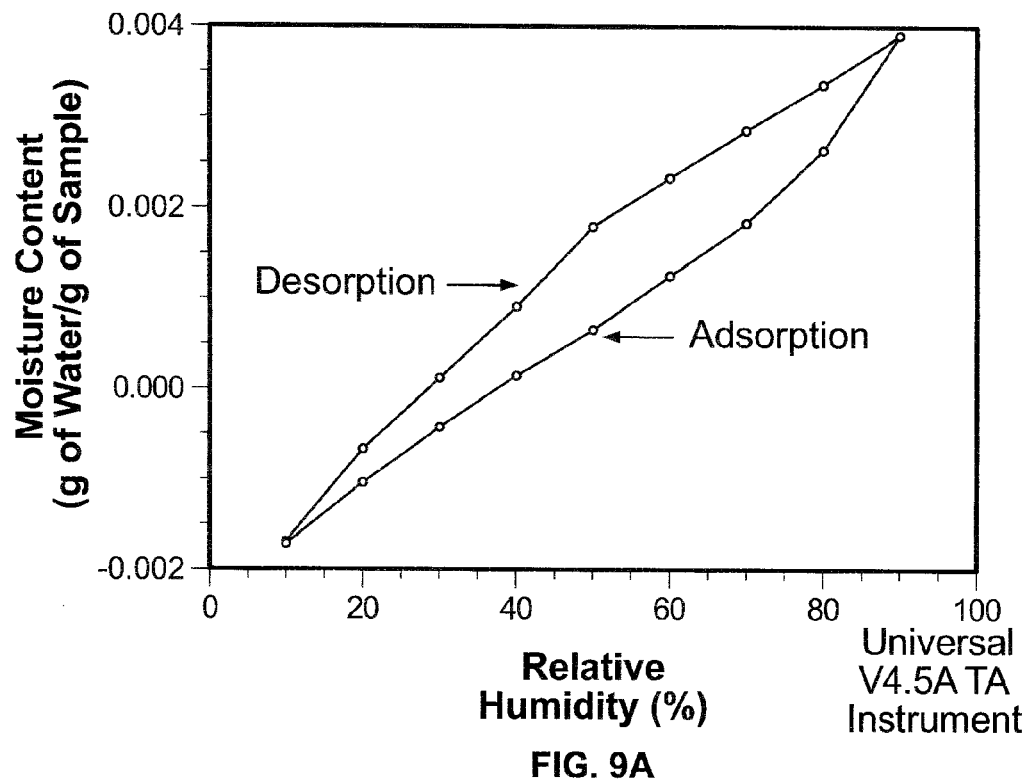
FIGS. 9A and 9B show the moisture content in Form I and II, respectively, over a range of relative humidities.
Figure 9B:
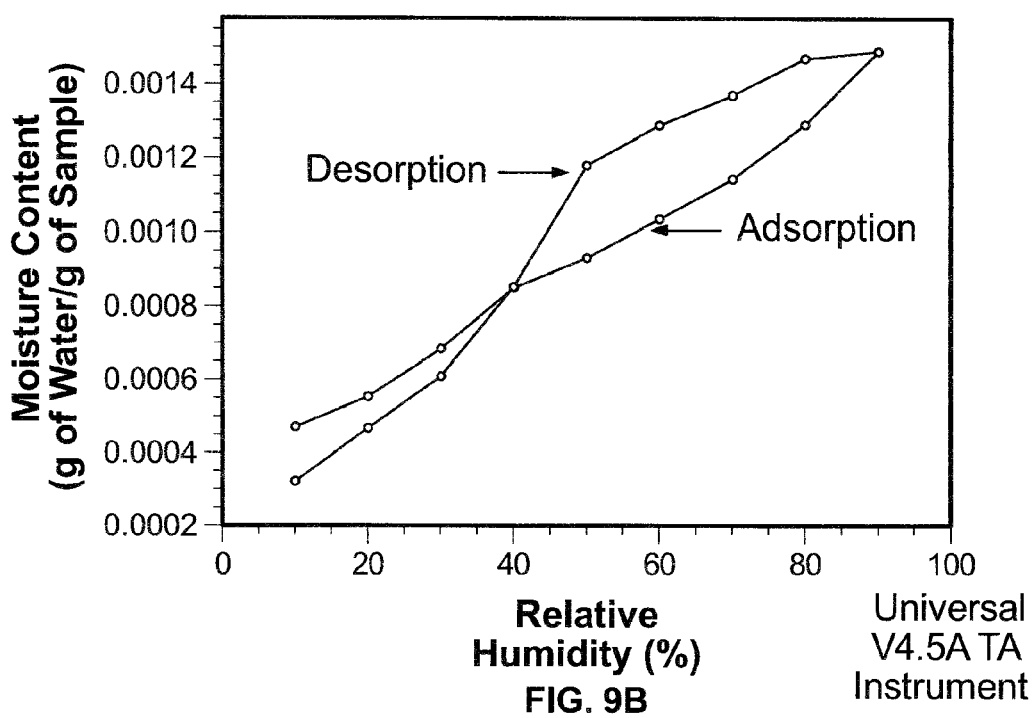

FIGS. 9A and 9B show adsorption and desorption traces for polymorphic Form I and polymorphic II, respectively, at constant temperature over a range of humidities. Both graphs show that the polymorphs absorb less than 1 wt % moisture at 90% relative humidity at 25° C. This Example supports the non-hygroscopic nature of polymorphic Form I and polymorphic Form II.

Example 12

Isolation of Form I from Reaction Mixture

A reaction vessel was charged with 5-fluoro-3-phenyl-2-((1S)-1-((9-(tetrahydro-2H-pyran-2-yl)-9H-purin-6-yl) amino)propyl)quinazolin-4(3H)-one (35.1 grams), absolute ethanol (48 mL), water (24 mL), and 12N hydrochloric acid (HCl) (5 mL). The mixture was agitated at about 21° C. and additional 12N HCl was added in small portions to produce a solution. As the reaction progressed, a hydrochloride salt of (S)-2-(1-(9H-purin-6-ylamino)propyl)-5-fluoro-3-phenylquinazolin-4(3H)-one crystallized from solution, forming a suspension. After approximately two hours, the acidic reaction suspension was combined with 50 mL ethanol. The suspension was neutralized with aqueous sodium carbonate solution (5.5 grams in 50 mL water) via slow addition until the pH reached about 7.5. The volume of base used was about 35-40 mL. Form I seeds of (S)-2-(1-(9H-purin-6-ylamino)propyl)-5-fluoro-3-phenylquinazolin-4(3H)-one (187 mg) were added to the reaction mixture. The mixture was agitated, and heated to about 50° C. Water (300 mL) was then added slowly until the ethanol fraction reached about 21% (v/v). Form I solids of (S)-2-(1-(9H-purin-6-ylamino)propyl)-5-fluoro-3-phenylquinazolin-4(3H)-one were isolated by filtration without cooling, washed with water, and dried under reduced pressure at about 40° C. The yield of dried Form I solids was 16.4 grams.

What is claimed is:

1. A polymorph of (S)-2-(1-(9H-purin-6-ylamino)propyl)-5-fluoro-3-phenylquinazolin-4(3H)-one, wherein the polymorph is Form II having an X-ray powder diffraction pattern comprising characteristic peaks, plus or minus 0.2 degrees 2θ, at 14.0 degrees 2θ, 18.6 degrees 2θ, and 24.3 degrees 2θ.

2. The polymorph of claim 1, wherein the polymorph has an X-ray powder diffraction pattern substantially as shown in FIG. 2A.

3. A polymorph of claim 1 obtained by:
   a) grinding polymorphic Form I of (S)-2-(1-(9H-purin-6-ylamino)propyl)-5-fluoro-3-phenylquinazolin-4(3H)-one; and
   b) stirring the ground polymorphic Form I in a solvent to form the polymorph of claim 1.

4. The polymorph of claim 3, wherein the ground polymorphic Form I is stirred in the solvent at a temperature of between about 10° C. and 25° C.

5. The polymorph of claim 3, wherein the grinding is performed using a mortar and pestle, a high shear wet mill, a high shear dry mixer, a jet mill, a ball mill, or a combination thereof.

6. A polymorph of claim 1 obtained by compressing polymorphic Form I of (S)-2-(1-(9H-purin-6-ylamino)propyl)-5-fluoro-3-phenylquinazolin-4(3H)-one at a pressure of between about 500 psi and 5000 psi to convert at least a portion of the polymorphic Form I to a polymorph of claim 1.

* * * * *